US012459945B2

(12) United States Patent
Iwanowicz

(10) Patent No.: US 12,459,945 B2
(45) **Date of Patent: *Nov. 4, 2025**

(54) USE OF CASEINOLYTIC PROTEASE P FUNCTION AS A BIOMARKER OF DRUG RESPONSE TO IMIPRIDONE-LIKE AGENTS

(71) Applicant: Madera Therapeutics, LLC, Cary, NC (US)

(72) Inventor: Edwin Iwanowicz, Cary, NC (US)

(73) Assignee: Madera Therapeutics, LLC, Cary, NC (US)

( * ) Notice: Subject to any disclaimer, the term of this patent is extended or adjusted under 35 U.S.C. 154(b) by 1105 days.

This patent is subject to a terminal disclaimer.

(21) Appl. No.: 17/459,960

(22) Filed: Aug. 27, 2021

(65) Prior Publication Data

US 2022/0089596 A1 Mar. 24, 2022

Related U.S. Application Data

(63) Continuation-in-part of application No. PCT/US2020/019944, filed on Feb. 26, 2020.

(60) Provisional application No. 62/975,088, filed on Feb. 11, 2020, provisional application No. 62/931,043, filed on Nov. 5, 2019, provisional application No. 62/901,142, filed on Sep. 16, 2019, provisional application No. 62/885,055, filed on Aug. 9, 2019, provisional application No. 62/871,694, filed on Jul. 8, 2019, provisional application No. 62/840,254, filed on Apr. 29, 2019, provisional application No. 62/825,667, filed on Mar. 28, 2019, provisional application No. 62/819,204, filed on Mar. 15, 2019, provisional application No. 62/811,432, filed on Feb. 27, 2019.

(51) Int. Cl.

| | |
|---|---|
| ***C07D 471/14*** | (2006.01) |
| ***A61P 35/00*** | (2006.01) |
| ***C07D 471/04*** | (2006.01) |

(52) U.S. Cl.
CPC ............ *C07D 471/14* (2013.01); *A61P 35/00* (2018.01); *C07D 471/04* (2013.01)

(58) Field of Classification Search
CPC .................................................... C07D 471/14
See application file for complete search history.

(56) References Cited

U.S. PATENT DOCUMENTS

| | | | |
|---|---|---|---|
| 10,239,877 B2 | 3/2019 | Janda et al. | |
| 10,526,332 B2 | 1/2020 | Xu et al. | |
| 2010/0113487 A1 | 5/2010 | Boyle et al. | |
| 2023/0339947 A1* | 10/2023 | Iwanowicz | .......... C07D 271/06 |

FOREIGN PATENT DOCUMENTS

| | | |
|---|---|---|
| WO | 2008130584 | 10/2008 |
| WO | 2012079164 | 6/2012 |
| WO | 2018031987 | 2/2018 |
| WO | 2018031990 | 2/2018 |

OTHER PUBLICATIONS

American Chemical Society. Chemical Abstract Service. RN 1073723-18-8. Entered into STN: Nov. 21, 2008. (Year: 2008).*
Pubchem, Substance Record for SID 90314507, Available Date: Feb. 22, 2010 [retrieved May 13, 2020]. Retrieved from the Internet: <URL: https://pubchem.ncbi.nlm.nih.gov/substance/90314507/version/1>. entire document.
Examination Report dated Aug. 12, 2022 for corresponding UK application No. GB2113038.0.
Extended European Search Report dated Sep. 22, 2022 for corresponding European application No. 20762147.5.

* cited by examiner

*Primary Examiner* — John S Kenyon
(74) *Attorney, Agent, or Firm* — Lewis Kohn & Walker LLP; David M. Kohn

(57) ABSTRACT

Use of caseinolytic protease P (ClpP) function and/or concentration as a biomarker for predicting the response of a neoplastic disease, preferably cancer or another disease where enhancing ClpP activity may provide a therapeutic benefit, to a compound of Formula I. In other aspects it relates to methods and kits, as well as methods of treatment involving the use of the biomarker.

9 Claims, 14 Drawing Sheets

Specification includes a Sequence Listing.

ClpP activity with 0-1 µM TR57
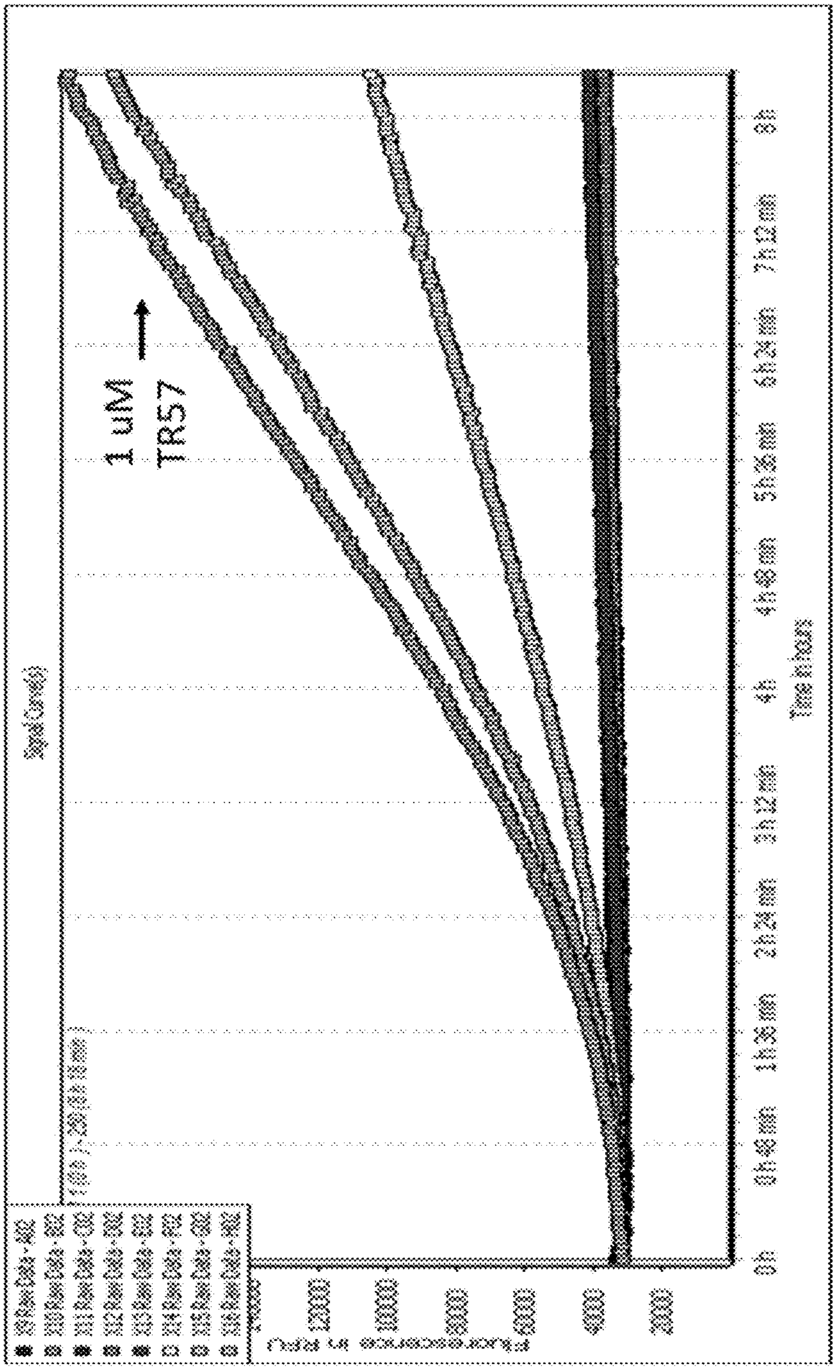
Fig. 1 con't.

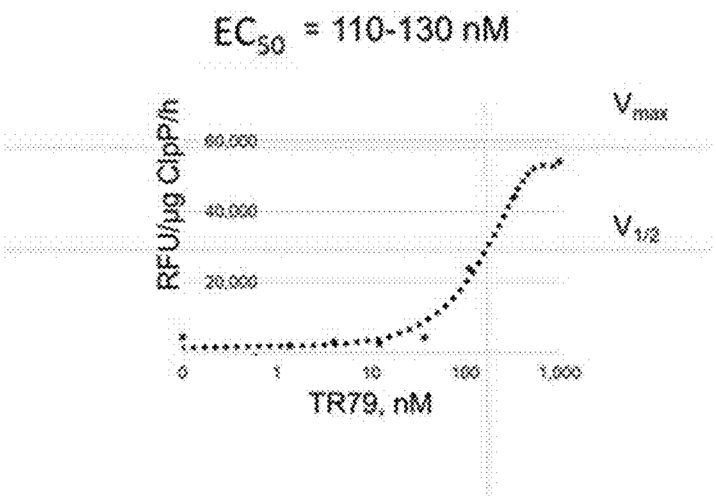
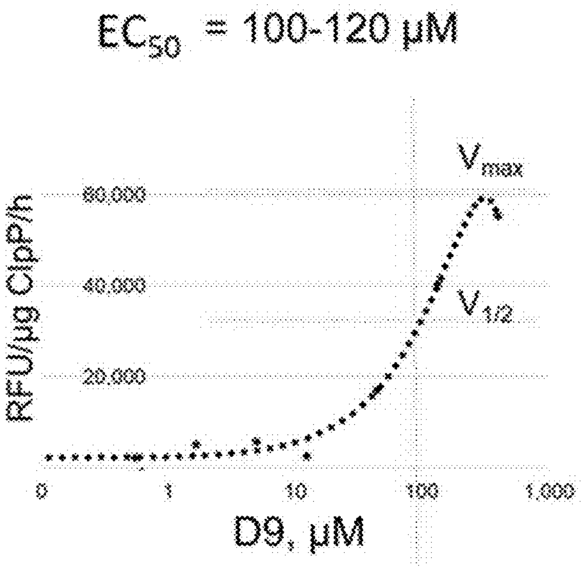
Fig. 3 con't.

In vitro drug competition

Minimum [drug] to compete ClpP in vitro:

[Onc201] = 1 - 10 μM

[TR-31] = 0.1 - 1 μM

Competition ability:

10 μM Onc201 = 1 μM TR-31 (TR-31 is 10 X more effective)

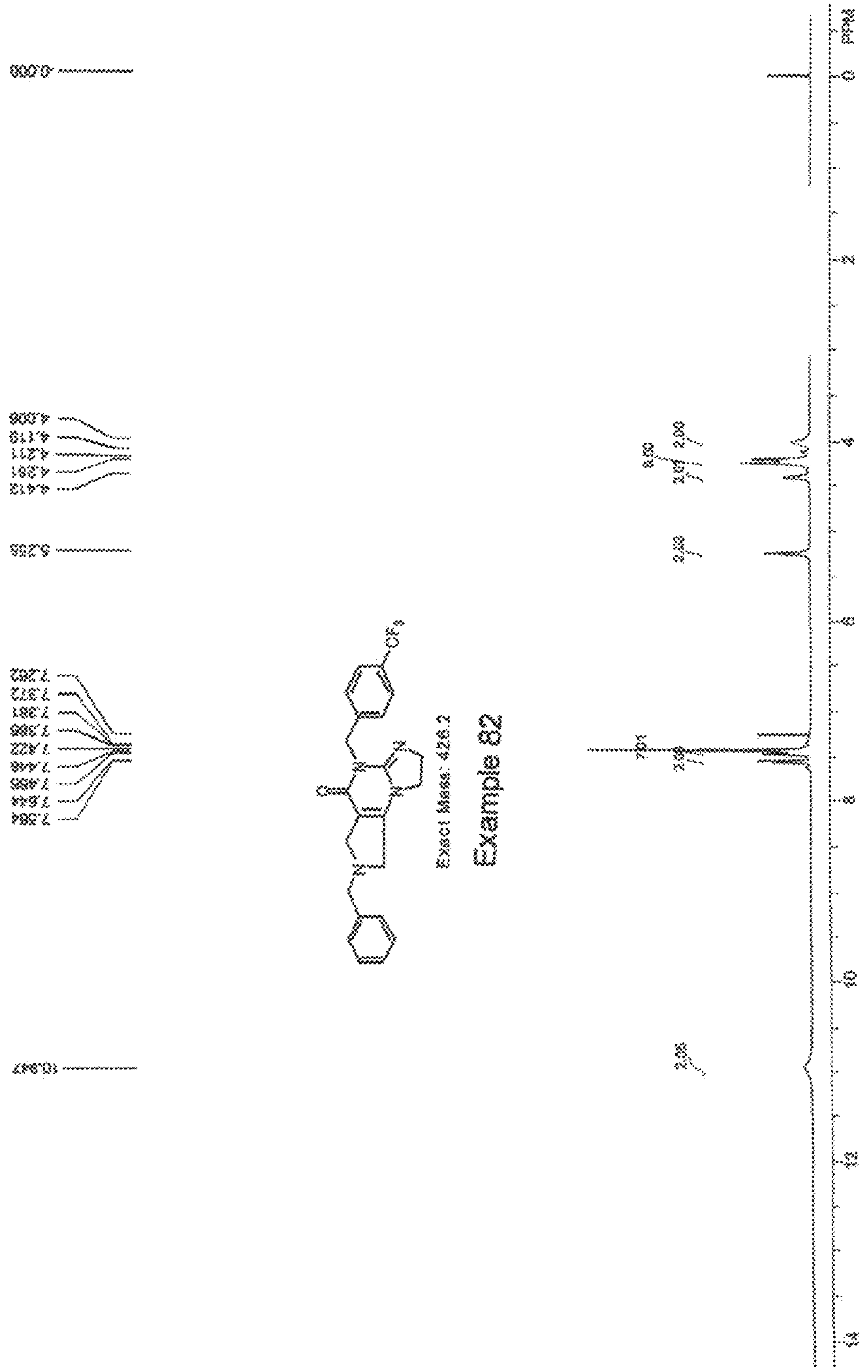
Fig. 7 con't

Example 80

Integration Results

Signal 1: DAD1 A, Sig=220,4 Ref=off

| # | R.T. | Type | Height | Height% | Width | Area | Area % |
|---|---|---|---|---|---|---|---|
| 1 | 1.546 | BB | 1899.081 | 100.000 | 0.057 | 6928.201 | 100.000 |

Fig. 8 con't
Signal 2: DAD1 B, Sig=254,4 Ref=off
| # | R.T. | Type | Height | Height% | Width | Area | Area % |
|---|---|---|---|---|---|---|---|
| 1 | 1.546 | BB | 526.161 | 100.000 | 0.050 | 1633.410 | 100.000 |
Signal 3: MSD1 TIC, MS File
| # | R.T. | Type | Height | Height% | Width | Area | Area % |
|---|---|---|---|---|---|---|---|
| 1 | 1.554 | BB | 1.086e+006 | 100.000 | 0.077 | 5.645e+006 | 100.000 |
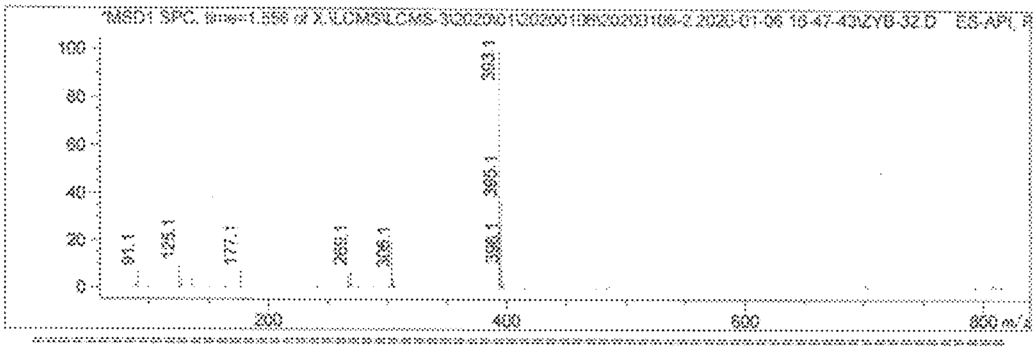
* End of Report *

EC50: 91 nM

EC50 = 539 nM

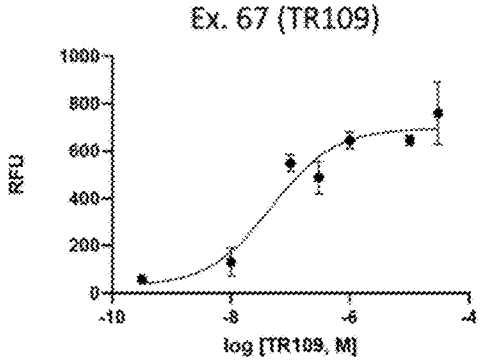
EC50: 48 nM
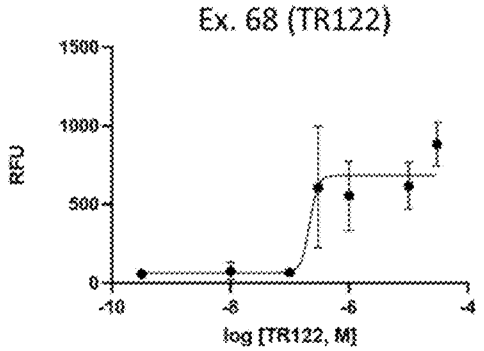
EC50 217 nM
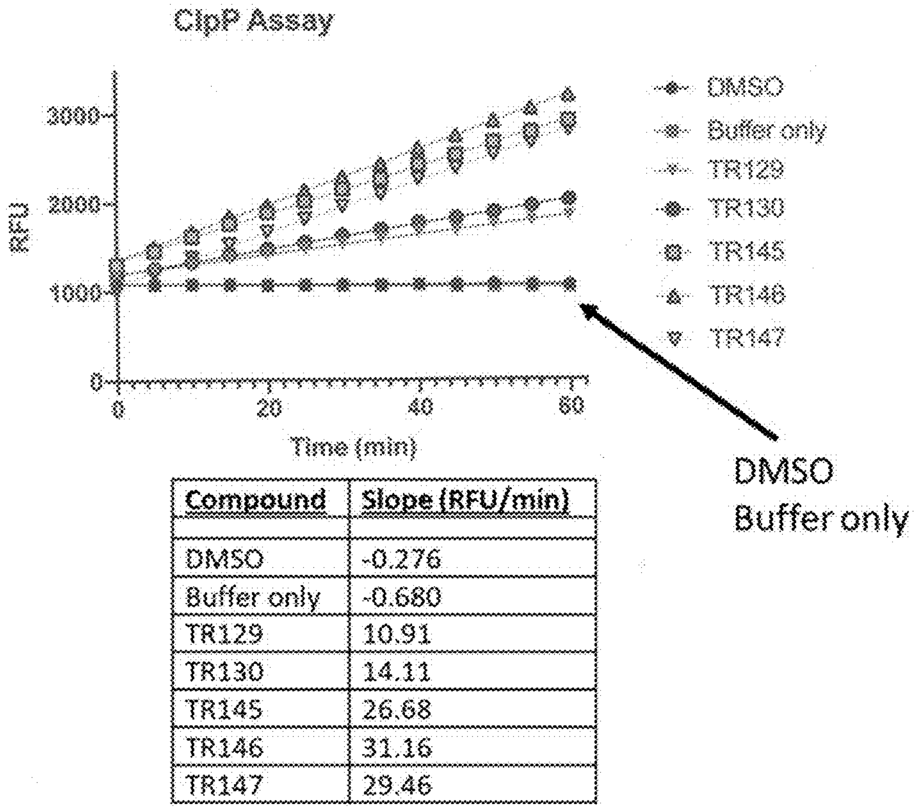
| Compound | Slope (RFU/min) |
|---|---|
| | |
| DMSO | -0.276 |
| Buffer only | -0.680 |
| TR129 | 10.91 |
| TR130 | 14.11 |
| TR145 | 26.68 |
| TR146 | 31.16 |
| TR147 | 29.46 |
Fig. 10 con't.

SEQUENCE LISTING

<160> NUMBER OF SEQ ID NOS: 1

<210> SEQ ID NO 1
<211> LENGTH: 277
<212> TYPE: PRT
<213> ORGANISM: Homo sapiens

<400> SEQUENCE: 1

Met Trp Pro Gly Ile Leu Val Gly Gly Ala Arg Val Ala Ser Cys Arg
1               5                   10                  15

Tyr Pro Ala Leu Gly Pro Arg Leu Ala Ala His Phe Pro Ala Gln Arg
            20                  25                  30

Pro Pro Gln Arg Thr Leu Gln Asn Gly Leu Ala Leu Gln Arg Cys Leu
        35                  40                  45

His Ala Thr Ala Thr Arg Ala Leu Pro Leu Ile Pro Ile Val Val Glu
    50                  55                  60

Gln Thr Gly Arg Gly Glu Arg Ala Tyr Asp Ile Tyr Ser Arg Leu Leu
65                  70                  75                  80

Arg Glu Arg Ile Val Cys Val Met Gly Pro Ile Asp Asp Ser Val Ala
                85                  90                  95

-continued

```
Ser Leu Val Ile Ala Gln Leu Leu Phe Leu Gln Ser Glu Ser Asn Lys
            100                 105                 110

Lys Pro Ile His Met Tyr Ile Asn Ser Pro Gly Gly Val Val Thr Ala
        115                 120                 125

Gly Leu Ala Ile Tyr Asp Thr Met Gln Tyr Ile Leu Asn Pro Ile Cys
    130                 135                 140

Thr Trp Cys Val Gly Gln Ala Ala Ser Met Gly Ser Leu Leu Leu Ala
145                 150                 155                 160

Ala Gly Thr Pro Gly Met Arg His Ser Leu Pro Asn Ser Arg Ile Met
                165                 170                 175

Ile His Gln Pro Ser Gly Gly Ala Arg Gly Gln Ala Thr Asp Ile Ala
            180                 185                 190

Ile Gln Ala Glu Glu Ile Met Lys Leu Lys Lys Gln Leu Tyr Asn Ile
        195                 200                 205

Tyr Ala Lys His Thr Lys Gln Ser Leu Gln Val Ile Glu Ser Ala Met
    210                 215                 220

Glu Arg Asp Arg Tyr Met Ser Pro Met Glu Ala Gln Glu Phe Gly Ile
225                 230                 235                 240

Leu Asp Lys Val Leu Val His Pro Pro Gln Asp Gly Glu Asp Glu Pro
                245                 250                 255

Thr Leu Val Gln Lys Glu Pro Val Glu Ala Ala Pro Ala Ala Glu Pro
            260                 265                 270

Val Pro Ala Ser Thr
        275
```

USE OF CASEINOLYTIC PROTEASE P FUNCTION AS A BIOMARKER OF DRUG RESPONSE TO IMIPRIDONE-LIKE AGENTS

REFERENCE TO SEQUENCE LISTING

The Sequence Listing submitted Nov. 27, 2021, as a text file named "1070_205WO_ST25.txt," created on Nov. 27, 2021, and having a size of 4,000 bytes is hereby incorporated by reference pursuant to 37 CFR § 1.52(e)(5).

FIELD OF THE INVENTION

The present invention relates to the use of caseinolytic protease P (ClpP) function and/or concentration as a biomarker for predicting the response of a neoplastic disease, preferably cancer or another disease where enhancing ClpP activity may provide a therapeutic benefit, to a compound of Formula I. In other aspects it relates to methods and kits, as well as methods of treatment involving the use of the biomarker. In addition, chemical matter that activates ClpP is described.

BACKGROUND OF THE INVENTION

Mammalian mitochondria contain a serine protease complex, (ClpP), that is the proteolytic component of the ClpXP protein degradation complex. This complex plays a central role in mitochondrial protein quality control (Houry, W. A. et al, Cell Chemical Biology 2018, 25, 1017-1030 and references cited therein) and in regulating bioenergetic activity of a cell. Houry, W. A. et al also reports that ClpP is highly expressed in multiple cancers and has important roles in cell metastasis. In addition, mitochondrial dysfunction is central in the disease mechanism and likely a causative factor for many neurodegenerative diseases (Beal and Johri, J Pharmcol Exp Thera. 2012, 342(3), 619-630 and references cited therein). Deficiency in ClpP induces an overload of mitochondrial misfolded/unfolded proteins, suppresses mitochondrial respiratory activity, increases mitochondrial oxidative damage and causes cell death (Qi et al, Acta Neuropathologica, 2019, 137, 939-960 and references cited therein).

Agents have been identified that regulate the function of ClpP. The direct activation of a protease with a small molecule is a rare occurrence in drug discovery. Agents that activate ClpP have been reported (Sieber, S. A. et al, Angew. Chem. Int. Ed. 2018, 57, 14,602-14607 and references cited therein). In addition, agents that inhibit ClpP have also been reported (Schimmer, A. D. et al, Cancer Cell 2015, 27, 864-876 and references cited therein). Both Schimmer, A. D. et al and Sieber, S. A. et al describe the use of their agents to treat cancer. Orally active agents to treat cancer have a preferred market potential due to ease of administration when dosed repeatedly. However, highly potent small molecule upregulators of ClpP activity are not known. Larger macrocyclic activators of ClpP are known, "ADEPs" but lack the structural characteristics for oral bioavailability (Lipinski's rules, Oprea et al, Adv. Drug Deliv Rev. 2016, 101, 89-98 and references cited therein).

Proteases highly similar to human ClpP have been found to be encoded in the genome of bacteria and some viruses. Agents that modulate ClpP function have been shown to have utility in treating bacterial infections. Kao R. Y. T. et al describe small-molecule inhibitors of ClpP and their effects on *Staphylococcus aureus* (Kao, R. Y. T. et al, PNAS 2018, 115, 8003-8008 and references cited therein). In addition, ClpP activators been described (Lee R. E. et al, ACS Infect Dis 2019, November 8; 5(11): 1915-1925 and references cited therein.)

Mitochondria have a number of quality control systems to insure homostasis (proteostasis). Deficiencies in these systems lead to mitochondrial dysfunction, a hallmark of aging, various neurodegenerative diseases, cardiovascular diseases and cancer (Li R. et al, Ann Rev Biophy, 2020, Jan. 13. doi: 10.1146/annurev-biophys-121219-081604 and references cited therein, Martins L. M., J Mol Med, 2013, 91, 665-671 and references cited therein and Jeong Y. Y., Cells, 2020, 9(1), 150 and references cited therein. Alpha-synuclein accumulation and mitochondrial dysfunction have been implicated in the pathology of Parkinson's disease and Alzheimer's disease (Qi et al, Acta Neuropathologica, 2019, 137, 939-960 and references cited therein and Nielsen and Twohig, Mol Neurodegener, 2019, 14(1), 23 and references cited therein). In addition, alpha-synuclein can lead to a decrease of the protein level of ClpP. Notably enhancement of ClpP activity in cellular systems reduced alpha-synuclein-associated pathology.

ONC201, a small molecule drug to treat cancer, has advanced to clinical trials and is being evaluated for the treatment of several cancers. Several published reports describe various aspects of the mechanism of action for ONC201. Publications describe that ONC201 functions through G protein-coupled receptors (GPCRs) (El-Deiry W. S., Neoplasia 2018, 20, 80-91 and references cited therein). Additionally, a report describes changes in cellular function, including mitochondrial function with ONC201 treatment (Lipkowitz S., Oncotarget 2018, 9, 18, 454-18, 479 and references cited therein).

Perrault syndrome is a disorder characterized by ovarian dysgenesis in females and senrorineural hearing loss in both genders. In more severe cases, additional symptoms may include ataxia, neuropathies and intellectual disability (Dougan, D. A., Sci Rep 2018, 8(1), 12862 and references cited therein). Mutations in six different genes have been linked to this disease and for Perrault syndrome type 3 mutations in ClpP is causal. Two mutations, Y229D and 1208M are believed to alter the peptidase activity with Y229D shown to inhibit ClpP-peptidase activity.

Loss-of-function mutations in genes for heme biosynthetic enzymes can give rise to congenital porphyrias. ClpX promotes heme biosysnthesis and a mutation in ClpX (Gly298Asp) results in a pathological accumulation of the heme biosynthesis intermediate protophyria (PPIX). (Paw B. H., Proc. Natl. Acad. Sci. USA. 114:E8045-E8052 (2017) and referenced cited therein).

Non-dividing hepatocytes in end stage liver disease indicates permanent growth arrest, cryptogenic cirrhosis (Ramakrishna, G. et al, Cell Mol Gastroenterol Hepatol. 2019, 8(1):73-94 and references cited therein). A common cause of cryptogenic cirrhosis is fatty liver disease. Contemporary drug development processes, often termed translational medicine approaches, focus on identifying the correct patient for treatment with a specific intervention of a critical aspect of the disease process. This requires multiple inputs, including an understanding of specific molecular events critical to the individual's disease process and a clear understanding on how a specific therapeutic will intervene in that individual's disease process (Rossetti L., Drug Dis. Today 2016, 21, 517-526 and references cited therein). Central to this approach are the development and use of biomarkers and related companion diagnostics with specific therapeutic treatment.

SUMMARY OF THE INVENTION

In this invention we report that human ClpP (hClpP or HSClpP) is a biomarker for the chemical action of ONC201 and related chemical analogs and this biomarker can be used to determine if a patient is a candidate for this drug treatment and if the drug treatment is having the expected molecular effect. Specifically, we show that these compounds directly bind and activate the peptidase activity of hClpP. The binding and activating effects on hClpP occur in a time and dose-dependent manner and parallel the growth inhibitory effects of these compounds on cancer cells. Our findings thus demonstrate that the biological actions of ONC201 (and related compounds), are dependent on the physical activation of hClpP. Our findings pertain to hClpP and ClpP (ClpP) in other mammalian species. In addition, ONC201 and related chemical analogs, bind directly to and activate the peptidase activity of bacterial ClpP (bClpP). This pertains to *Staphylococcus aureus* and other bacterial species. We expect that the effects on bClpP occur in a time and dose-dependent manner and are responsible for the growth inhibitory effects of these compounds on bacterial cells. We also expect that the anti-microbial actions of ONC201 and structurally related compounds, are due to the physical activation of bClpP. This invention also allows for the evaluation of susceptible bacteria to ONC201 and chemically-related compounds by molecular means.

A large group of neurodegenerative disorders are characterized by the relative selective death of neuronal subtypes. Impaired mitochondrial dysfunction may be causative for a number of neurodegenerative diseases such as, but are not limited to, Parkinson's disease, Huntington's disease, amyotrophic lateral sclerosis, Friedreichs ataxia and Alzheimer's disease. This invention entails the use of agents described herein to treat these diseases, how to select a patient that will benefit from such treatment and a method to monitor a patient's response to the treatment.

We disclose that fluorescent, positron emission tomography ($F^{18}$-PET), near infrared and other small molecule probes, can be chemically coupled to the compounds described in this invention, as a direct way to image ClpP expression in tumors or other tissues (Liu H-W., Chem Soc. Review, 2018, 47, 7140-7180 and references cited therein; Pantel A. R., Cancer Lett, 2017, 387, 25-31 and references cited therein). This provides the basis for detecting ClpP expression in tumors as a biomarker of cancer. Secondly, the use of these probes can be directly used to measure the efficacy of ClpP engagement by drugs such as ONC201 and the chemical agents described herein or other ClpP binders, by an assay to measure the competitive reduction in ClpP binding. Target (ClpP) engagement by ONC201, or other compounds described herein, can be directly measured in live animals, people or in in vitro screening assays. Combined with ClpP enzymatic activity assays, the engagement of this ClpP by small molecules can be directly measured. Third, the development of ClpP-dependent activity probes can be applied to determine the activity of ClpP in tumors or cell lysates. Applying the principles of enzymatically-activated fluorescent probes as described in (Liu H-W., Chem Soc. Review, 2018, 47, 7140-7180 and references cited therein), we propose attaching reactive chemical groups to the compounds of this invention for this purpose. The amine reactive TR-compounds will be conjugated with chemical fluorescent substrates with the purposes of targeting these compounds to ClpP in intact tumors and directly measuring ClpP using this approach. Fourth, the use of the TR-compound probe, can be used to discover novel ClpP binding molecules by utilizing the displacement of the TR-probe compound by unknown compounds in high throughput assays using time-resolved fluorescence assays or other assays. We further disclose that the use of our TR-compound probe can be similarly used to identify novel small molecule binders of the bacterial ClpP (bClpP) enzymes. Combined with bClpP activity assays, the effects of these small molecules on bClpP activity can be directly determined. This provides unique TR-probe compounds, for the discovery of bClpP binders as potential antibacterial agents. In addition, new chemical matter that has utility as anticancer agents is described.

DETAILED DESCRIPTION OF THE INVENTION

Figure 1:
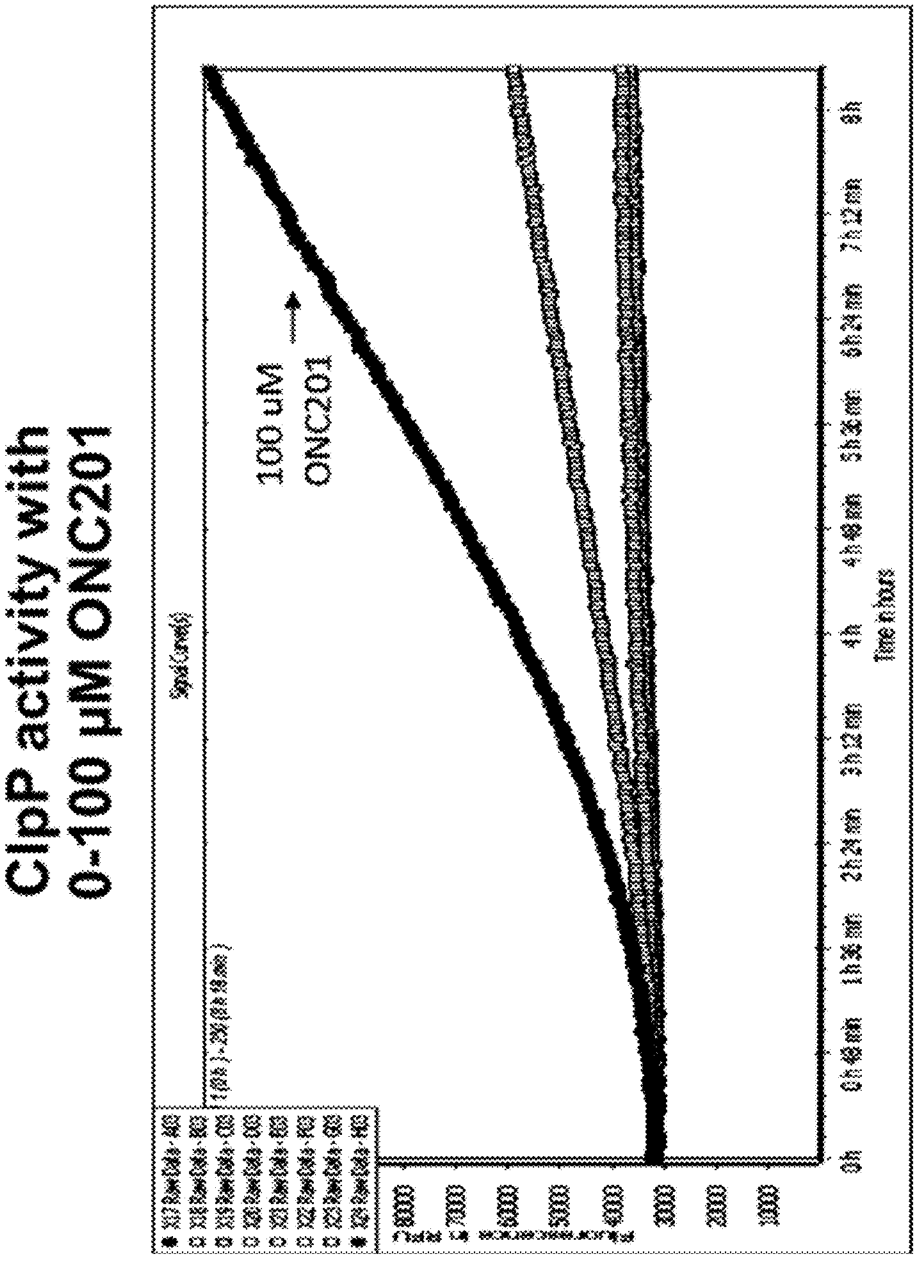
FIG. 1: Kinetics of hClpP activity without pre-incubation with ONC201 and Ex. 51 (TR57) hClpP Peptide Hydrolysis Assays in the Presence of ONC201 and Ex. 51 (TR57). Shown are the time- and dose-dependent increase in coumarin fluorescence release from Ac-WLA-AMC by the enzymatic activity of purified hClpP. Protocol 1.

The present invention relates to methods of determining whether an individual is responsive to an agent described by Formula I and methods of determining whether an individual is maintaining responsiveness to an agent described by Formula I comprising assaying biological samples for the level of at least one biomarker. The present invention further relates to kits for performing the methods. The present invention further describes new chemical matter and its use to treat cancer, various proliferative diseases, various immunological diseases, various inflammatory diseases, bacterial infections, neurodegenerative diseases, viral diseases such as HIV, the condition acquired immunodeficiency syndrome (AIDS), hereditary spastic paraplegia, cystic fibrosis (CF) and Perrault syndrome. ClpP, its relationship to cancer and other diseases and targeted therapeutics, is described by Wong, K S, and Houry, W A (ACS Chem. Biol., 2019: DIO: 10.102.1021/acschembio.9b00347, and references cited therein). All publications, patents and patent applications cited in this specification are herein incorporated by reference as if each individual publication, patent or patent application were specifically and individually indicated to be incorporated by reference.

The term: "and references cited therein" following a specific citation, be it a publication, patent or patent application, indicates all citations within that specific citation are also herein incorporated.

Decreased expression of ClpP, both in RNA and in the expressed protein (ClpP), in cells from a patient with hereditary spastic paraplegia may be corrected by the treatment of compounds and the use of methods from this invention (Bross, P et al, Neuroscience, 2008, 153, 474-482).

One aspect of the invention relates to the treatment of hereditary spastic paraplegia through the administration of compounds of this invention.

One aspect of the present invention relates to novel methods for the detection of ClpP as a biomarker of cancer and other diseases. This is based on our original discovery that ONC201 and chemically related compounds as defined by Formula I, are high-affinity binders and activators of ClpP enzymatic activity. Another aspect of this invention relates to the use of the described herein agents as activity probes to detect ClpP protein and activity levels in tumors and cells including biological samples taken from mammals. These biological samples may be acquired from the mammal before or after treatment with compounds described by Formula I. In addition, these samples may also be treated with compounds described by Formula I and the response to the compound may be determined by changes in ClpP activity levels and protein levels, or other related marker to ClpP activity.

Another aspect of the invention relates to the regulation of the complex ClpXP and its components, ClpP and the AAA+ ATPase, ClpX. This regulation of these components may be used to treat disease.

One aspect of the present invention relates to novel methods for the detection of ClpXP as a biomarker of cancer and other diseases.

One aspect of the present invention relates to novel methods for the detection of ClpX as a biomarker of cancer and other diseases.

Another aspect of the present invention relates to the identification of other chemical matter as binders to ClpP. Compounds of the present invention may be used in an assay to screen libraries of compounds to identify new chemical matter.

A. Development of High Affinity ClpP Binding Probes for Detection of ClpP in Live Animals, Patients or Intact Cells.

Figure 4:
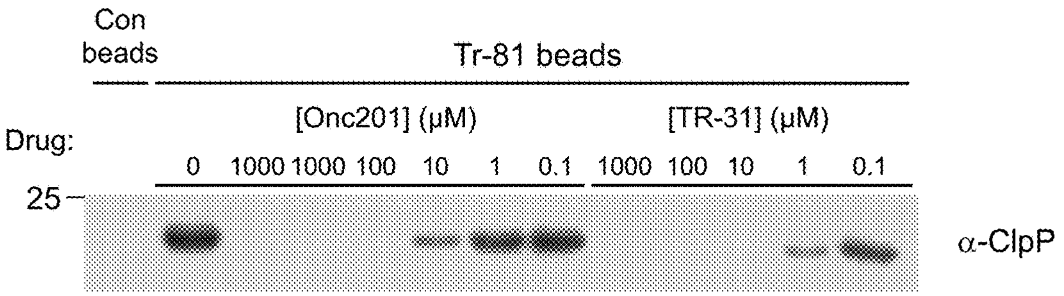
FIG. 4: HClpP is Binding Protein for Compounds of the Invention. Shown are in vitro hClpP binding to immobilized Ex. 59 (TR81) Sepharose beads. HELA cell lysates were briefly incubated (10 min) with carrier (0.1% DMSO) or ONC201 or Ex. 2 (TR31, ONC212) dissolved in DMSO at the concentrations shown in FIG. 4. These samples were applied to an immobilized TR-81 Sepharose column (50 ul) and washed to remove unbound proteins. Samples were eluted with SDS-PAGE sample buffer, applied to SDS-PAGE and the samples Western blotted for hClpP. As shown, increasing the concentration of ONC201 and Ex. 2 (TR31) in the lysate, competed hClpP off of the Ex. 59 (TR81) resin in a dose-dependent manner. Similar results were obtained with Ex. 51 (TR57) (not shown). Studies are to determine compounds of the invention binding to the protein ClpP.
Figure 5:
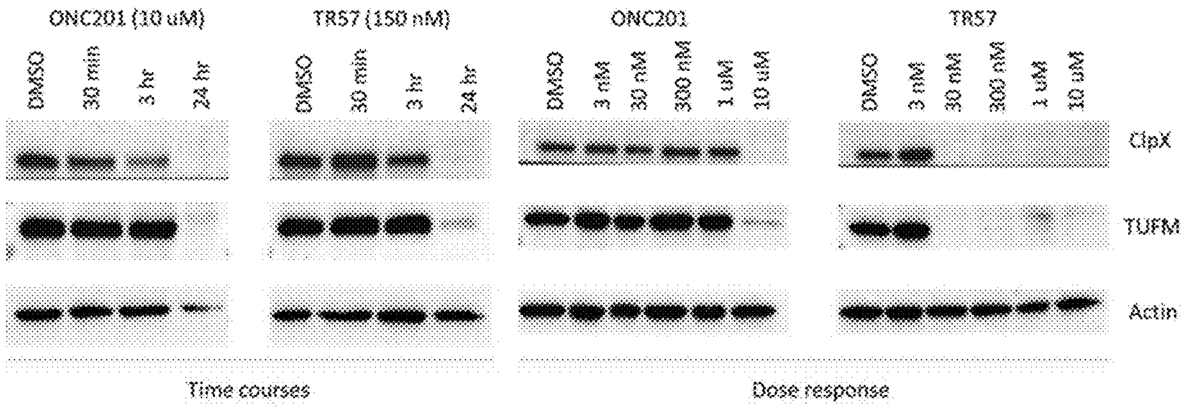
FIG. 5: ClpX and TUFM concentration, response and time course data for ONC201 and TR57 on SUM159 cells. Shown are studies showing effects of compounds of the invention and reduction of the protein ClpX and TUFM, as measured by Western blots, when cancer cells (SUM159) are exposed to these compounds.
Figure 6:
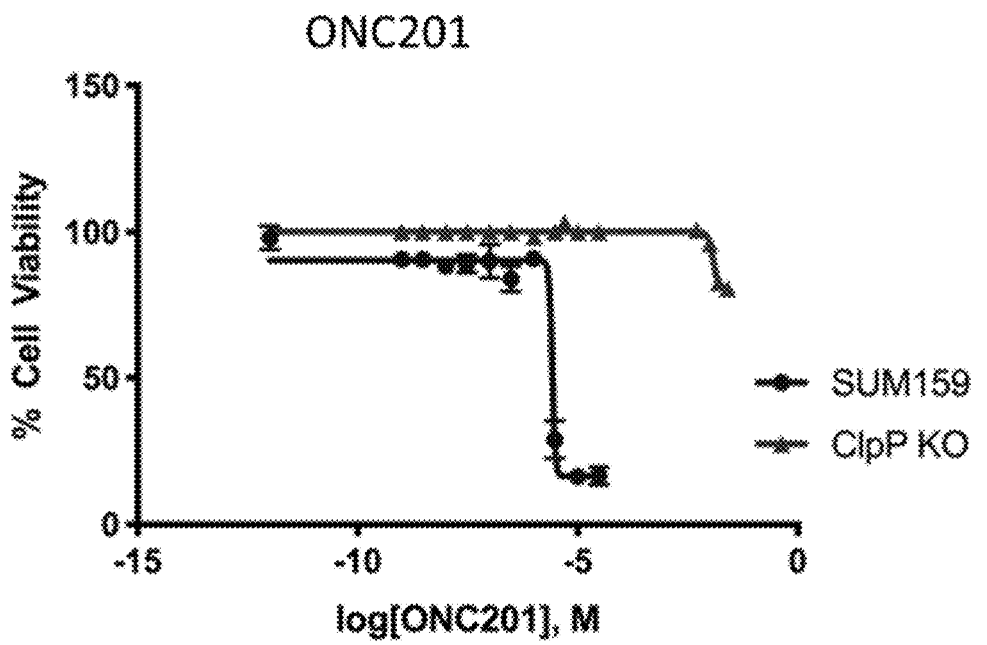
FIG. 6: ClpP CRISPR knockout cells are resistant to the effects of ONC201 and TR57. Shown are studies examining the effects of ONC201 and Ex. 51 (TR57) on growth of the cancer cell line SUM159 compared to that of a cell line (SUM159, ClpP CRISPR KO), without the protein ClpP.
Figure 6:
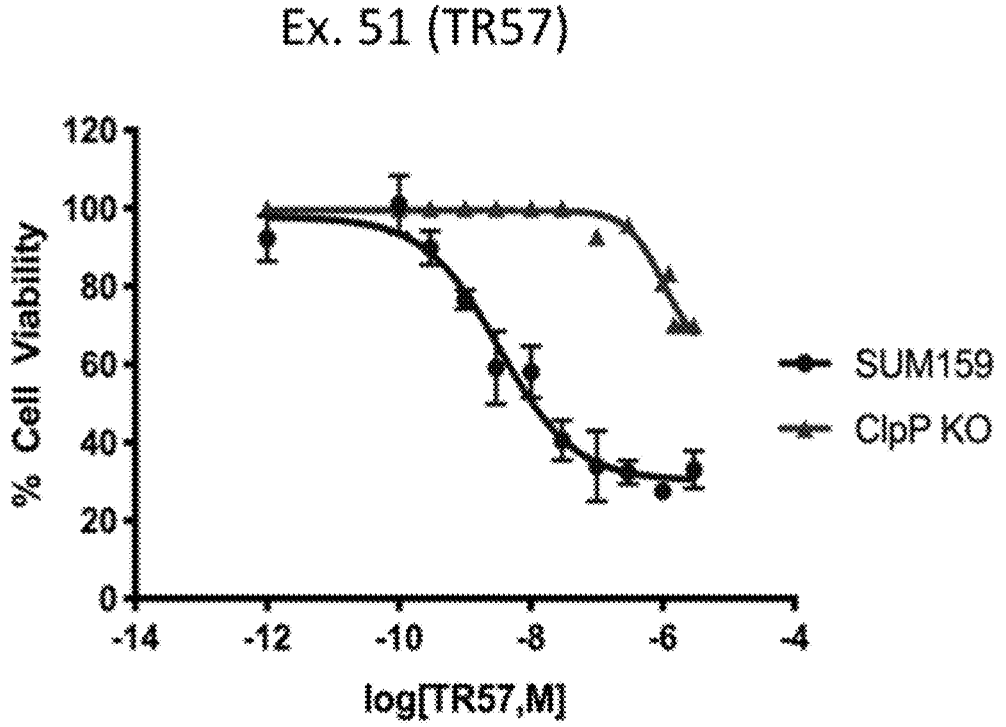
Figure 7:
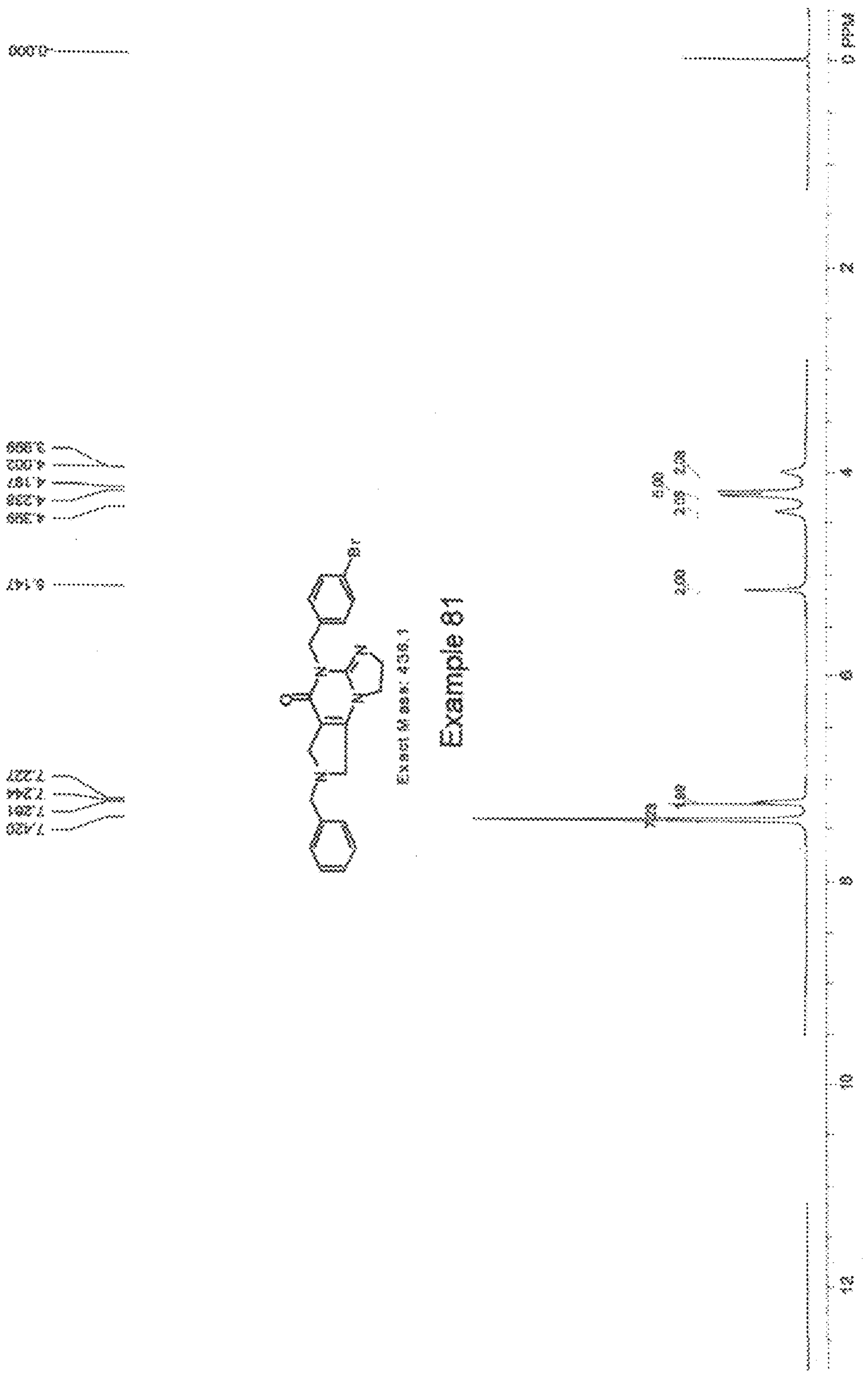
FIG. 7: $^{1}$HNMR of Examples 81 and 82.

We have found that hClpP directly binds to TR79, TR80 and TR81, compounds of this inventions, when coupled to Sepharose beads. In addition, we determined that ONC201, ONC212 (TR31) and others (TR57), compete hClpP (human-ClpP) off of the above functionalized Sepharose beads in a dose-dependent manner (FIG. 4). This provides that ONC201 and other analogs and related chemical matter of the invention bind to hClpP (Graves L. M. et al, ACS Chem Biol., 2019, 14(5), 1020-1029 and references cited therein. This invention further describes the attachment of fluorescent, infrared, PET and other imaging moieties to a subset of compounds of Formula I using chemically reactive functionality. These imaging moieties in this invention disclosure are known collectively as "Dyes". Examples of compounds with these characteristics are TR79, TR80 and TR81. These probes are used as cell permeable imaging probes for the detection of ClpP as a biomarker of cancer or other disease.

B. Measure Probe Displacement to Evaluate Small Molecule Therapeutic Binding to Biomarker Protein ClpP.

The probes, as described herein, of the present invention will be used to measure the efficacy of target (ClpP) engagement by therapeutics directed at this enzyme. This would include ONC201, ONC206, ONC212 and other compounds of Formula I for the treatment of disease in a mammal. Animals or humans will be exposed to these probes and tumors imaged by fluorescence, PET or other imaging modalities. Exposure to ONC201 or related compounds will be performed and the amount of probe remaining bound to ClpP will be determined by imaging. Determining signal before and after such exposure will allow a direct measurement of how effectively this biomarker target (ClpP) is binding ONC201 or other ClpP binding related therapeutics.

C. Develop ClpP Activity-Based Probes for the Detection of ClpP Activity in Tumors, Cells or Cell Lysates A subset of compounds of Formula I are used to create activity-dependent probes selective for ClpP. An extensive array of cleavable fluorescent, or other such chemical moieties, known to those skilled in the art, are used to create ClpP activity probes. Examples of suitable compounds of Formula I are TR79, TR80 and TR81, each has a chemically reactive amine suitable for coupling (resulting in a "couple agent") with a wide range of agents. These couple agents will be applied to 1) direct binding of these molecules to ClpP, and 2) measure ClpP activity through hydrolysis of the fluorescent molecule. These agents will also be used for imaging of ClpP activity in tumors, tissues or cell lysates.

D. Development of ClpP Probes for High Throughput Screens for ClpP Binding and Regulation The various probes/coupled agents described in this invention are diagnostic reagents to evaluate compound binding to ClpP from mammalian and bacterial sources. The assay is based on the displacement of the fluorescent (or otherwise) probes from ClpP. Time-resolved fluorescence anisotropy (or similar assays) will be used to measure displacement of the probe compound from ClpP by said compounds. This will form the basis of an HTS screening procedure to discover new small molecule interactors of ClpP from human or bacterial sources.

DEFINITIONS

The terms used herein have their ordinary meaning and the meaning of such terms is independent at each occurrence thereof. That notwithstanding and except where stated otherwise, the following definitions apply throughout the specification and claims.

a) Biology Related Definitions

Neoplastic disease: neoplasia is the abnormal growth and proliferation of abnormal cells or abnormal amounts of cells due to a benign or malignant process.

Biological sample. The term "sample" with respect to an individual encompasses blood and other liquid samples of biological origin, solid tissue samples such as a biopsy specimen and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

The term "biological sample" encompasses a clinical sample. The types of "biological samples" include, but are not limited to: tissue obtained by surgical resection, tissue obtained by biopsy, cells in culture, cell supernatants, cell lysates, tissue samples, organs, bone marrow, blood, plasma, serum, fine needle aspirate, lymph node aspirate, cystic aspirate, a paracentesis sample, a thoracentesis sample and the like. A "biological sample" can include cells (e.g., target cells, normal cells, blood cells, tissue cells, etc.) can be suspected of comprising such cells, or an be devoid of cells. A biological sample can include biological fluids derived from cells (e.g., a cancerous cell, an infected cell, etc.), e.g., a sample comprising polynucleotides and/or polypeptides that is obtained from such cell (e.g., a cell lysate or other cell extract comprising polynucleotides and/or polypeptides). A biological sample comprising an infected cell from a patient can also contain non-infected cells. In some embodiments the biological sample is blood or a derivative thereof, e.g. plasma, serum, etc.

Obtaining and assaying a sample. The term "assaying" is used herein to include the physical steps of manipulating a biological sample to generate data related to the sample. As will be readily understood by one of ordinary skill in the art, a biological sample must be "obtained" prior to assaying the sample. This, the term "assaying" implies that the sample has been obtained. The terms "obtained" or "obtaining" as used herein encompass the act of receiving an extract or isolated biological sample. For example, a testing facility can "obtain" a biological sample in the mail (or via delivery, etc.) prior to assaying the sample. In some cases, the biological sample was "extracted" or "isolated" from an individual by another party prior to mailing (i.e., delivery, transfer, etc.), and then "obtained" by the testing facility upon arrival of the sample. This, a testing facility can obtain the sample and then assay the sample, thereby producing data related to the sample.

The terms "obtained" or "obtaining" as used herein can also include the physical extraction or isolation of a biological sample from the subject. Accordingly, a biological sample can be isolated from a subject (and thus "obtained") by the same person or same entity that subsequently assays the sample. When a biological sample is "extracted" or "isolated" from a first party or entity and then transferred (e.g., delivered, mailed, etc.) to a second party, the sample was obtained by the first party (and also "isolated" by the first party), and then subsequently "obtained" (but not "isolated") by the second party. Accordingly, in some embodiments, the step of obtaining does not comprise the step of isolating a biological sample.

In some embodiments, the step of obtaining comprises the step of isolating a biological sample (e.g., a pre-treatment biological sample, a post-treatment biological sample, etc.). Methods and protocols for isolating various biological samples (e.g., a blood sample, a serum sample, a plasma sample, a biopsy sample, an aspirate, etc.) will be known to one of ordinary skill in the art and any convenient method may be used to isolate a biological sample.

It will be understood by one of ordinary skill in the art that in some cases, it is convenient to wait until multiple samples (e.g., a pre-treatment biological sample and a post-treatment biological sample) have been obtained prior to assaying the samples. Accordingly, in some cases an isolated biological sample (e.g., a pre-treatment biological sample, a post-treatment biological sample, etc.) is stored until all appropriate samples have been obtained. One of ordinary skill in the art will understand how to appropriately store a variety of different types of biological samples and any convenient method of storage may be used (e.g., refrigeration) that is appropriate for the particular biological sample. In some embodiments, a pre-treatment biological sample and a post-treatment are assayed in parallel. In some cases, multiple different post-treatment biological samples and/or a pre-treatment biological sample are assayed in parallel. In some cases, biological samples are processed immediately or as soon as possible after they are obtained.

In subject methods, the concentration (i.e., “level”), or expression level of a gene product, which may be an RNA, a protein, etc., (which will be referenced herein as a biomarker), in a biological sample is measured (i.e, “determined”). By “expression level” (or “level”) it is meant the level of gene product (e.g., the absolute and/or normalized value determined for the RNA expression level of a biomarker or for the expression level of the encoded polypeptide, or the concentration of the protein in a biological sample). The term “gene product” or “expression product” are used herein to refer to the RNA transcription products (RNA transcripts, e.g., mRNA, an unspliced RNA, a splice variant mRNA, and/or fragmented RNA) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc.

The terms “determining”, “measuring”, “evaluating”, “assessing”, “assaying”, and “analyzing” are used interchangeably herein to refer to any form of measurement, and include determining if an element is present or not. These terms include both quantitative and/or qualitative determinations. Assaying may be relative or absolute. For example, “assaying” can be determining whether the expression level is less than or “greater than or equal to” a particular threshold, (the threshold can be predetermined or can be determined by assaying a control sample). On the other hand, “assaying to determine the expression level” can mean determining a quantitative value (using any convenient metric) that represents the level of expression (i.e, expression level, e.g., the amount of protein and/or RNA, e.g., mRNA) of a particular biomarker. The level of expression can be expressed in arbitrary units associated with a particular assay (e.g., fluorescence units, e.g., mean fluorescence intensity (MFI)), or can be expressed as an absolute value with defined units (e.g., number of mRNA transcripts, number of protein molecules, concentration of protein, etc.). Additionally, the level of expression of a biomarker can be compared to the expression level of one or more additional genes (e.g., nucleic acids and/or their encoded proteins) to derive a normalized value that represents a normalized expression level. The specific metric (or units) chosen is not crucial as long as the same units are used (or conversion to the same units is performed) when evaluating multiple biological samples from the same individual (e.g., biological samples taken at different points in time from the same individual). This is because the units cancel when calculating a fold-change (i.e., determining a ratio) in the expression level from one biological sample to the next (e.g., biological samples taken at different points in time from the same individual).

For measuring RNA levels, the amount or level of an RNA in the sample is determined, e.g., the level of an mRNA. In some instances, the expression level of one or more additional RNAs may also be measured, and the level of biomarker expression compared to the level of the one or more additional RNAs to provide a normalized value for the biomarker expression level. Any convenient protocol for evaluating RNA levels may be employed wherein the level of one or more RNAs in the assayed sample is determined.

A number of exemplary methods for measuring RNA (e.g., mRNA) expression levels (e.g., expression level of a nucleic acid biomarker) in a sample are known by one of ordinary skill in the art, and any convenient method can be used. Exemplary methods include, but are not limited to: hybridization-based methods (e.g., Northern blotting, array hybridization (e.g., microarray); in situ hybridization; in situ hybridization followed by FACS; and the like) (Parker & Barnes, Methods in Molecular Biology 106:247-283 (1999)); RNAse protection assays (Hod et al, Biotechniques, 1992, 13 852-854 and references cited therein); PCR-based methods (e.g., reverse transcription PCR (RT-PCR), quantitative RT-PCR (qRT-PCR), real-time RT-PCR, etc.)(Weis et al, Trends in Genetics 1992, 8 263-264 and references cited therein); nucleic acid sequencing methods (e.g., Sanger sequencing, Next Generation sequencing (i.e., massive parallel high throughput sequencing, e.g., Illumina’s reversible terminator method, Roche’s pyrosequencing method (454), Life Technologies’ sequencing by ligation (the SOLiD platform), Life Technologies’ Ion Torrent platform, single molecule sequencing, etc.); and the like.

In some embodiments, the biological sample can be assayed directly. In some embodiments, nucleic acid of the biological sample is amplified (e.g., by PCR) prior to assaying. As such, techniques such as PCR (Polymerase Chain Reaction), RT-PCR (reverse transcriptase PCR), qRT-PCR (quantitative RT-PCR), etc. can be used prior to the hybridization methods and/or the sequencing methods discussed above.

For measuring mRNA levels, the starting material is typically total RNA or poly A+ RNA isolated from a biological sample (e.g., suspension of cells from a peripheral blood sample, a bone marrow sample, etc., or from a homogenized tissue, e.g., a homogenized biopsy sample, an aspirate, a homogenized paraffin- or OCT-embedded sample, etc.). General methods for mRNA extraction are well known in the art and are disclosed in standard textbooks of molecular biology, including Ausubel et al., Current Protocols of Molecular Biology, John Wiley and Sons (1997). RNA isolation can also be performed using a purification kit, buffer set and protease form commercial manufacturers, according to the manufacturer’s instructions. For example, RNA from cell suspensions can be isolated using Qiagen RNeasy mini-columns, and RNA from cell suspensions or homogenized tissue samples can be isolated using the TRIzol reagent-based kits (Invitrogen), MasterPure™ Complete DNA and RNA Purification Kit (EPICENTRE™, Madison, Wis.), Paraffin Block RNA Isolation Kit (Ambion, Inc.) or RNA Stat-60 kit (Tel-Test).

A variety of different manners of measuring mRNA levels are known in the art, e.g., as employed in the field of differential gene expression analysis. One representative and convenient type of protocol for measuring mRNA levels is array-based gene expression profiling. Such protocols are hybridization assays in which a nucleic acid that displays “probe” nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839;

5,580,732; 5,661,028; 5,800,992; the disclosures of which are herein incorporated by reference; as well as WO 95/21265; WO 96/31622; WO 97/10365; WO 97/27317; EP373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The term "Stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of transcriptosome), may be both qualitative and quantitative.

Alternatively, non-array-based methods for quantitating the level of one or more nucleic acids in a sample may be employed. These include those based on amplification protocols, e.g., Polymerase Chain Reaction (PCR)-based assays, including quantitative PCR, reverse-transcription PCR (RT-PCR), real-time PCR, and the like, e.g., TaqMan® RT-PCR, MassARRAY® System, BeadArray® technology, and Luminex® technology; and those that rely upon hybridization of probes to filters, e.g., Northern blotting and in situ Examples of some of the nucleic acid sequencing methods listed above are described in the following references: Margulies et al, Nature 2005, 437, 376-80 and references cited therein; Ronaghi et al, Analytical Biochemistry 1996, 242, 84-89 and references cited therein; Shendure et al, Science 2005, 309 1728 and references cited therein; Imelfort et al, Brief Bioinform. 2009, 10, 609-618 and references cited therein; Fox et al, Methods Mol Biol. 2009, 553, 79-108 and references cited therein; Appleby et al, Methods Mol Biol. 2009; 513, 19-39 and references cited therein and Morozova et al, Genomics 2008, 92, 255-264 and references cited therein, which are incorporated by reference for the general descriptions of the methods and the particular steps of the methods, including all starting products, reagents, and final products for each of the steps.

For measuring protein levels, the amount or level of a polypeptide in the biological sample is determined. In some embodiments, the extracellular protein level is measured. For example, in some cases, the protein (i.e., polypeptide) being measured is a secreted protein (e.g., a cytokine or chemokine) and the concentration can therefore be measured in the extracellular fluid of a biological sample (e.g., the concentration of a protein can be measured in the serum). In some embodiments the concentration is a relative value measured by comparing the level of one protein relative to another protein. In other embodiments the concentration is an absolute measurement of weight/volume or weight/weight hybridization.

In some cases, the cells are removed from the biological sample (e.g., via centrifugation, via adhering cells to a dish or to plastic, etc.) prior to measuring the concentration. In some cases, the intracellular protein level is measured by lysing the removed cells of the biological sample to measure the level of protein in the cellular contents. In some cases, both the extracellular and intracellular levels of protein are measured by separating the cellular and fluid portions of the biological sample (e.g., via centrifugation), measuring the extracellular level of the protein by measuring the level of protein in the fluid portion of the biological sample, and measuring the intracellular level of protein by measuring the level of protein in the cellular portion of the biological sample (e.g., after lysing the cells). In some cases, the total level of protein (i.e., combined extracellular and intracellular protein) is measured by lysing the cells of the biological sample to include the intracellular contents as part of the sample.

In some instances, the concentration of one or more additional proteins may also be measured, and biomarker concentration compared to the level of the one or more additional proteins to provide a normalized value for the biomarker concentration. Any convenient protocol for evaluating protein levels may be employed wherein the level of one or more proteins in the assayed sample is determined.

While a variety of different manners of assaying for protein levels are known to one of ordinary skill in the art and any convenient method may be used, one representative and convenient type of protocol for assaying protein levels is ELISA, an antibody-based method. In ELISA and ELISA-based assays, one or more antibodies specific for the proteins of interest may be immobilized onto a selected solid surface, preferably a surface exhibiting a protein affinity such as the wells of a polystyrene microtiter plate. After washing to remove incompletely adsorbed material, the assay plate wells are coated with a non-specific "blocking" protein that is known to be antigenically neutral with regard to the test sample such as bovine serum albumin (BSA), casein or solutions of powdered milk. This allows for blocking of non-specific adsorption sites on the immobilizing surface, thereby reducing the background caused by non-specific binding of antigen onto the surface. After washing to remove unbound blocking protein, the immobilizing surface is contacted with the sample to be tested under conditions that are conducive to immune complex (antigen/antibody) formation. Following incubation, the antisera-contacted surface is washed so as to remove non-immunocomplexed material. The occurrence and amount of immunocomplex formation may then be determined by subjecting the bound immunocomplexes to a second antibody having specificity for the target that differs from the first antibody and detecting binding of the second antibody. In certain embodiments, the second antibody will have an associated enzyme, e.g. urease, peroxidase, or alkaline phosphatase, which will generate a color precipitate upon incubating with an appropriate chromogenic substrate. After such incubation with the second antibody and washing to remove unbound material, the amount of label is quantified, for example by incubation with a chromogenic substrate such as urea and bromocresol purple in the case of a case of a peroxidase label or 2,2'-azino-di-(3-ethyl-benzthiazoline)-6-sulfonic acid (ABTS) and $H_2O_2$, in the case of a peroxidase label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody. The solid substrate upon which the antibody or antibodies are immobilized can be made of a wide variety of materials and in a wide variety of shapes, e.g., microtiter plate, microbead, dipstick, resin particle, etc. The substrate may be chosen to maximize signal to noise ratios, to minimize background binding, as well as for ease of separation and cost. Washes may be affected in a manner most appropriate for the substrate being used, for example, by removing a bead or dipstick from a reservoir, emptying or diluting a reservoir such as a microtiter plate well, or rinsing a bead, particle, chromatographic column or filter with a wash solution or solvent.

Alternatively, non-ELISA based-methods for measuring the levels of one or more proteins in a sample may be employed. Representative exemplary methods include but are not limited to antibody-based methods (e.g., Western blotting, proteomic arrays, xMAP™ microsphere technology (e.g., Luminex® technology), immunohistochemistry, flow cytometry, and the like) as well as non-antibody-based methods (e.g., mass spectrometry).

Biomarkers. The term "biomarker" as used herein means a gene product, i.e. protein or RNA, whose concentration (i.e., "level") and enzymatic activity (function) reports the activity of an administered modulator of ClpP (both level and/or function). This ClpP modulator is also known as a ClpP agent. Because some individuals may not be responsive to treatment with a ClpP agent, a biomarker can be used to determine whether a ClpP agent has the desired effect in an individual (e.g., determining whether the individual is responsive to the ClpP agent, determining whether the individual is maintaining responsiveness to the ClpP agent, and if the individual is a candidate for treatment with the ClpP agent, etc.). For example, a biomarker whose level increases upon administration of a ClpP agent when an individual is responsive to the ClpP agent is a "positive biomarker"; a biomarker whose level decreases upon administration of a ClpP agent when an individual is responsive to the ClpP agent is a "negative biomarker"; and a biomarker whose level does not change upon administration of a ClpP agent when an individual is responsive to the ClpP agent is a "neutral biomarker."

In some embodiments, the concentration or level of a biomarker is determined before and after the administration of a ClpP agent and the degree of change, or lack thereof, is interpreted as an indication of whether an administered ClpP agent is in fact affecting the function and/or level of ClpP, and/or whether this blockade has the desired effect (i.e., whether the immune system has been activated in response to contact with or administration of a ClpP agent). In summary, the concentration or level of a biomarker is determined before and after the administration of a ClpP agent to an individual and the degree of change, or lack thereof, of level and/or enzymatic function (taken in context with time of exposure to the ClpP agent) is interpreted as an indication of whether the individual would be "responsive" to the ClpP agent, whether the individual is "responsive" to the ClpP agent and/or whether the individual is "maintaining responsiveness" to the ClpP agent.

A "positive biomarker" is a biomarker whose level increases in response to contact and/or treatment with a ClpP agent when an individual and/or cell is responsive to the ClpP agent. As such, a biological sample isolated from an individual to whom a ClpP agent has been administered exhibits an increased level of a positive biomarker (relative to the level of the same biomarker measured from the same type of biological sample from the same individual prior to the administration of the ClpP agent) if the ClpP agent is having the desired effect. In some embodiments, the level of a positive biomarker increases by about 1.5-fold or more (e.g., 2-fold or more, 2.5-fold or more, 3-fold or more, 3.5-fold or more, 4-fold or more, 4.5-fold or more, or 5-fold or more, 8-E) fold or more, 10-fold or more, 15-fold or more) in response to contact and/or treatment with a ClpP agent when an individual and/or cell is responsive to the ClpP agent.

Positive biomarkers include, but are not necessarily limited to: ClpP, ClpX, ClpXP, H3 K27M, LONP and Malic enzyme 1 (ME1). Additional positive biomarkers (>2× increase) established by treatment of a cancer cells with a compound of Formula I include:

| | | |
|---|---|---|
| Bis(5-nucleosyl)-tetraphosphatase [asymmetrical] | Guanine nucleotide-binding protein subunit alpha-11; Guanine nucleotide-binding protein subunit alpha-14 | Serine/arginine-rich splicing factor 10 |
| Plasminogen activator inhibitor 1 | Nuclear factor NF-kappa-B p100 subunit; Nuclear factor NF-kappa-B p52 subunit | Protein dpy-30 homolog |
| ATP-binding cassette sub-family D member 3 | Fragile X mental retardation protein 1 | Mediator of RNA polymerase II transcription subunit 15 |
| Plastin-1 | Intron-binding protein aquarius | H/ACA ribonucleoprotein complex subunit 2 |
| Cyclin-dependent kinase 6 | MKI67 FHA domain-interacting nucleolar phosphoprotein | Coronin-7 |
| Histone H2A type 1-C; Histone H2A type 3; Histone H2A type 1-B/E; Histone H2A type 1-A; Histone H2AX | Nucleolar protein 56 | Sodium bicarbonate cotransporter 3 |
| Catenin alpha-2 | Ephrin type-A receptor 2 | CCA tRNA nucleotidyltransferase 1, mitochondrial |
| Methyl-CpG-binding domain protein 3 | Tetratricopeptide repeat protein 4 | Probable dimethyladenosine transferase |
| Regulation of nuclear pre-mRNA domain-containing protein 2 | 60S ribosomal protein L7-like 1 | MMS19 nucleotide excision repair protein homolog |
| Charged multivesicular body protein 7 | Glucosylceramidase | ATP-dependent RNA helicase DDX18 |
| V-type proton ATPase subunit S1 | Sepiapterin reductase | Exosome complex component RRP40 |
| Nuclear receptor-binding protein | AMP-activated kinase (AMPK), cytosolic, phospho and non-phospho | CAM kinase kinase, cytosolic, phospho and non-phospho |

-continued

| | | |
|---|---|---|
| DRP1, cytosolic | Mitochondrial fission factor, (MFF1)-phospho and non phospho | Activating transcription factor 4 |
| C/EBP homologous protein | Alpha-Synuclein | Serine, threonine kinase TBK, total and phospho |
| Heme oxygenase 1 (HO1) | Nuclear Factor erythroid 2-related factor (NRF2) | Voltage-dependent anion channel 1, 2, 3, mitochondrial, total and phospho |

The level of any combination of the above positive biomarkers can be measured and utilized in the subject methods.

A "negative biomarker" is a biomarker whose level decreases in response to contact and/or treatment with a ClpP agent when an individual and/or cell is responsive to the ClpP agent. As such, a biological sample isolated from an individual to whom a ClpP agent has been administered exhibits a decreased level of a negative biomarker (relative to the level of the same biomarker measured from the same type of biological sample from the same individual prior to the administration of the ClpP agent) if the ClpP agent is having the desired effect. In some embodiments, the level of a negative biomarker decreases by about 1.5-fold or more (e.g., 2-fold or more, 2.5-fold or more, 3-fold or more, 3.5-fold or more, 4-fold or more, 4.5-fold or more, or 5-fold or more, 8-fold or more, 10-fold or more, 15-fold or more) in response to contact and/or treatment with a ClpP agent when an individual and/or cell is responsive to the anti-CD47 agent. Negative biomarkers include, but are not necessarily limited to: ClpP, ClpX, ClpXP, H3 K27M, LONP and Malic enzyme 1 (ME1). Additional negative biomarkers (>2× decrease) established by treatment of a cancer cells with a compound of Formula I include:

| | | |
|---|---|---|
| GrpE protein homolog 1, mitochondrial | 39S ribosomal protein L12, mitochondrial | Keratin, type II cytoskeletal 1 |
| 28S ribosomal protein S17, mitochondrial | E3 ubiquitin-protein ligase HECTD1 | Aconitate hydratase, mitochondrial |
| Keratin, type I cytoskeletal 10 | Elongation factor Tu, mitochondrial (TUFM) | Hydroxymethylglutaryl-CoA synthase, cytoplasmic |
| 2,4-dienoyl-CoA reductase, mitochondrial | NADH dehydrogenase [ubiquinone] 1 alpha subcomplex subunit 2 | Electron transfer flavoprotein subunit alpha, mitochondrial |
| 39S ribosomal protein L41, mitochondrial | Pyrroline-5-carboxylate reductase 1, mitochondrial | Methylcrotonoyl-CoA carboxylase beta chain, mitochondrial |
| 39S ribosomal protein L3, mitochondrial | 28S ribosomal protein S34, mitochondrial | 28S ribosomal protein S23, mitochondrial |
| Succinyl-CoA ligase [ADP-forming] subunit beta, mitochondrial | Acyl-coenzyme A thioesterase 13; Acyl-coenzyme A thioesterase 13, N-terminally processed | Methyltransferase-like protein 7A |
| 39S ribosomal protein L11, mitochondrial | Putative phospholipase B-like 2; Putative phospholipase B-like 2 32 kDa form; Putative phospholipase B-like 2 45 kDa form | Dihydrolipoyllysine-residue succinyltransferase component of 2-oxoglutarate dehydrogenase complex, mitochondrial |
| Isocitrate dehydrogenase [NADP], mitochondrial | ATP synthase subunit gamma, mitochondrial | Dihydrolipoyllysine-residue acetyltransferase component of pyruvate dehydrogenase complex, mitochondrial |
| Branched-chain-amino-acid aminotransferase, mitochondrial | Succinyl-CoA ligase [GDP-forming] subunit beta, mitochondrial | Delta(3,5)-Delta(2,4)-dienoyl-CoA isomerase, mitochondrial |
| Succinate dehydrogenase [ubiquinone] flavoprotein subunit, mitochondrial | Dihydrolipoyl dehydrogenase, mitochondrial | 39S ribosomal protein L49, mitochondrial |
| 39S ribosomal protein L37, mitochondrial | ATP synthase subunit g, mitochondrial | 39S ribosomal protein L13, mitochondrial |
| Succinate dehydrogenase [ubiquinone] iron-sulfur subunit, mitochondrial | ATP synthase F(0) complex subunit B1, mitochondrial | Sulfide:quinone oxidoreductase, mitochondrial |
| ATP synthase subunit e, mitochondrial | Succinyl-CoA ligase [ADP/GDP-forming] subunit alpha, mitochondrial | 39S ribosomal protein L2, mitochondrial |
| Myosin light chain 1/3, skeletal muscle isoform; Myosin light chain 3 | 28S ribosomal protein S7, mitochondrial | Synaptosomal-associated protein 29 |
| NADH dehydrogenase [ubiquinone] 1 alpha subcomplex subunit 5 | 39S ribosomal protein L38, mitochondrial | Polyribonucleotide nucleotidyltransferase 1, mitochondrial |
| ERAL1, mitochondria | IARS2, mitochondrial | Superoxide dismutase, cytoplasmic |
| Mitochondrial-processing peptidase subunit alpha | Nitric oxide associated protein 1 (NOA1), mitochondrial | NDUFV1, NDUFV2, mitochondrial |
| Activating transcription factor 4 | C/EBP homologous protein | Alpha-Synuclein |

-continued

| | | |
|---|---|---|
| Transcription factor A, mitochondrial (TFAM) | Serine, threonine kinase mTor, total and phospho | Eukaryotic translation initiation factor 4E binding protein (EIF4EBP), total and phospho |

A "neutral biomarker" is a biomarker whose level does not significantly increase or decrease in response to contact and/or treatment with a ClpP agent when an individual and/or cell is responsive to the ClpP agent. The term "neutral biomarker" is used to refer to a protein or RNA whose level may have been expected to change (e.g., because the level of the gene changes in other contexts that alter an individual's immune state, e.g., during an inflammatory response), but was experimentally shown not to change in a context where a ClpP agent is used modulate ClpP level and/or function. As such, a biological sample isolated from an individual to whom a ClpP agent has been administered exhibits a similar level of a neutral biomarker (relative to the level of the same biomarker measured from the same type of biological sample from the same individual prior to the administration of the ClpP agent or to a standardized control) if the ClpP agent is having the desired effect. In some embodiments, the level of a neutral biomarker changes less than about 5-fold (e.g., less than about 4.5-fold, less than about 4-fold, less than about 3.5-fold, less than about 3-fold, less than about 2.5-fold, less than about 2-fold, or less than about 1.5-fold) in response to contact and/or treatment with a ClpP agent when an individual and/or cell is responsive to the ClpP agent. Neutral biomarkers include, but are not necessarily limited to: ClpP, ClpXP, ClpX, H3 K27M, LONP and Malic enzyme 1 (ME1). In addition, for neurodegenerative diseases alpha-synuclein and alpha-synuclean A53T (mutant) may be used. The level of any combination of the above neutral biomarkers can be measured and utilized in the subject methods.

Chemistry Related Definitions

Chemical names, common names, and chemical structures may be used interchangeably to describe the structure. If a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" portions of "hydroxyalkyl," "fluoroalkyl," "—O-alkyl," etc.

As used herein, and throughout this disclosure, the following terms, unless otherwise indicated, shall be understood to have the following meanings:

The term "therapeutically effective amount" as used herein, refers to an amount of the compound of Formula (I) and/or additional therapeutic agent, or a composition thereof that is effective in producing the desired therapeutic, ameliorative, inhibitory or preventative effect when administered to a patient suffering from cancer or another disease or disorder of undesirable cell proliferation. In the combination therapies of the present invention, a therapeutically effective amount can refer to each individual agent or to the combination as a whole, wherein the amounts of all agents administered are together effective, but wherein the component agent of the combination may not be present individually in an effective amount. In reference to the treatment of cancer, a therapeutically effective amount, refers to that amount which has the effect of (1) reducing the size of the tumor, (2) inhibiting (that is slowing to some extent, preferably stopping) tumor metastasis, (3) inhibiting to some extent (preferably stopping) tumor growth or tumor invasiveness and/or (4) relieving to some extent (or preferably, eliminating) one or more signs or symptoms associated with cancer.

The term "preventing" as used herein with respect to cancer or a disease or disorder of undesirable cell proliferation, refers to reducing the likelihood or rate of disease or disorder progression.

The use of a dashed or dotted line signifies a single bond between said molecular fragment and another defined molecular fragment. For example, the selection of Q1 for Q in Formula (I) yields the following structure:

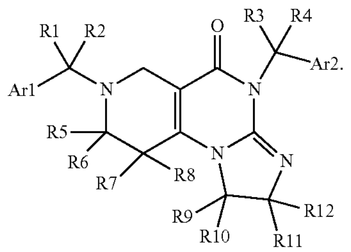

In another example, the selection of Q2 for Q in Formula (I) yields the following structure:

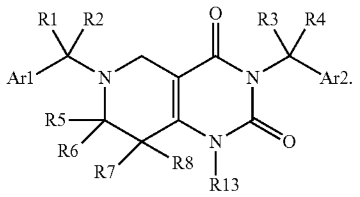

In another example, the selection of Q3 for Q in Formula (I) yields the following structure:

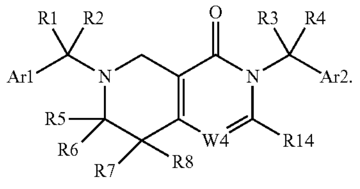

In another example, the selection of Q4 for Q in Formula (I) yields the following structure:

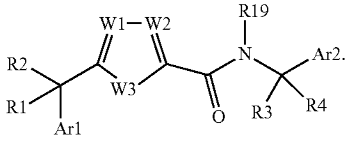

In another example, the selection of Q5 for Q in Formula (I) yields the following structure:

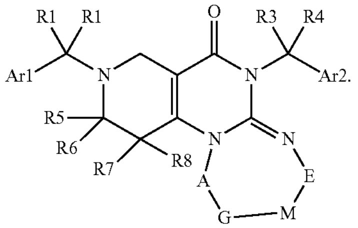

In another example, the selection of Q6 for Q in Formula (I) yields the following structure:

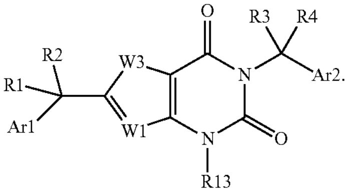

In another example, the selection of Q7 for Q in Formula (I) yields the following structure:

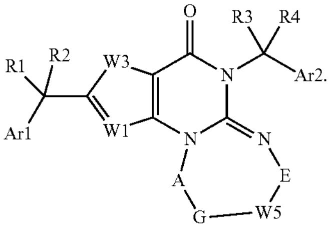

In another example, the selection of Q8 for Q in Formula (I) yields the following structure:

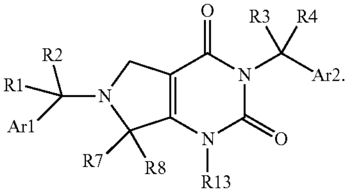

In another example, the selection of Q9 for Q in Formula (I) yields the following structure:

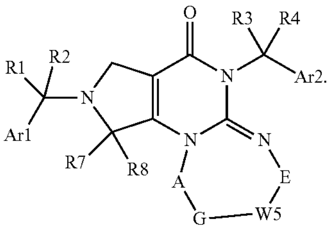

In another example, the selection of Q10 for Q in Formula (I) yields the following structure:

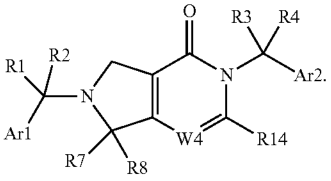

In another example, the selection of Q11 for Q in Formula (I) yields the following structure:

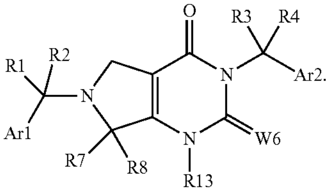

In another example, the selection of Q12 for Q in Formula (I) yields the following structure:

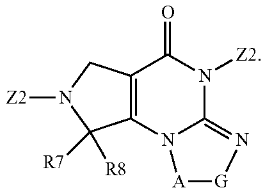

In another example, the selection of Q13 for Q in Formula (I) yields the following structure:

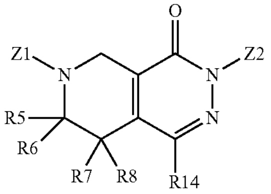

In another example, the selection of Q14 for Q in Formula (I) yields the following structure:

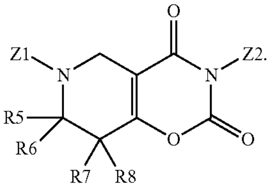

The term "alkyl" as used herein, refers to an aliphatic hydrocarbon group having one of its hydrogen atoms replaced with a bond having the specified number of carbon atoms. The alkyl group may be straight chain or branched chain groups. In addition to the term "alkyl", alkyl groups may be further defined by the number of carbon atom. Alkyl substituents typically contain 1 to 20 carbon atoms "(C1-C20)alkyl", preferably 1-12 carbon atoms "(C1-C12)alkyl", more preferably 1 to 8 carbon atoms "(C1-C8)alkyl", or 1 to 6 carbon atoms "(C1-C6)alkyl", or 1 to 4 carbon atoms "(C1-C4)alkyl". In different embodiments, an alkyl group contains from 7-12 carbon atoms "(C7-C12)alkyl" or from 7 to 20 carbon atoms "(C7-C20)alkyl". Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. All alkyl groups described herein may be optionally substituted by one or more substituent groups, which are selected independently unless otherwise indicated. Alkyl groups described herein as substituted alkyl ("substituted alkyl") will be substituted with one or more substituent groups, which are selected independently unless otherwise indicated. The total number of substituent groups may equal the total number of hydrogen atoms on the alkyl moiety, to the extent such substitution makes chemical sense. Optionally substituted alkyl groups ("optionally substituted alkyl") typically contain from 1 to 6 optional substituents, preferably from 1 to 4 optional substituents and more preferably from 1 to 3 optional substituents. For example, an optionally substituted ethyl group is "optionally substituted (C2)alkyl" or "(C2) optionally substituted alkyl" and a substituted ethyl group is "substituted (C2)alkyl" or "(C2) substituted alkyl".

Suitable substituent groups for alkyl, "alkyl", "optionally substituted alkyl" and "substituted alkyl" include, but are not limited to (C3-C8)cycloalkyl, 3-12 membered heterocyclyl, (C6-C12)aryl, 5-12 membered heteroaryl, halo, =O (oxo), =S (thiono), =N—CN, =N—$OR^X$, =$NR^X$, —CN, —C(O)$R^X$, —$CO_2R^X$, —C(O)$NR^XR^Y$, —$SR^X$, —$SOR^X$, —$SO_2R^X$, —$SO_2NR^XR^Y$, —$NO_2$, —$NR^XR^Y$, —$NR^X$C(O)$R^Y$, —$NR^X$C(O)$NR^XR^Y$, —$NR^X$C(O)$OR^X$, —$NR^XSO_2R^Y$, —$NR^XSO_2NR^XR^Y$, —$OR^X$, —OC(O)$R^X$ and —OC(O)$NR^XR^Y$; where in each $R^X$ and $R^Y$ is independently hydrogen, (C1-C6)alkyl, (C2-C6)alkenyl, (C2-C6)alkynyl, (C3-C6)cycloalkyl, 3-12 membered heterocyclyl, (C6-C12)aryl, or 5-12 membered heteroaryl, or $R^X$ and $R^Y$ may be taken together with the nitrogen atom to which they are attached to form a 3-12 membered heterocyclyl or 5-12 membered heteroaryl system, each optionally containing 0, 1 or 2 additional heteroatoms; each $R^X$ and $R^Y$ is optionally substituted with 1 to 3 substituents independently selected from the group consisting of halo, =O, —CN, —C(O)R', —$CO_2$R', —C(O)$NR'_2$, —$SO_2$R', —$NR'_2$, —OR', wherein each R' is independently hydrogen, (C1-C6)alkyl, (C3-C6) cycloalkyl, or 3-12 membered heterocyclyl. However, suitable substituent for "substituted alkyl" does not include hydrogen.

"Alkenyl" refers to an alkyl group, as defined herein, consisting of at least two carbon atoms and at least one carbon-carbon bond. Typically, alkenyl groups have 2 to 20 carbon atoms "(C2-C20)alkenyl", preferably 2 to 12 carbon atoms "(C2-C12)alkenyl", more preferably 2 to 8 carbon atoms "(C2-C8)alkenyl", or 2 to 6 carbon atoms "(C2-C6) alkenyl", or 2 to 4 carbon atoms "(C2-C4)alkenyl". Representative examples include, but are not limited to, ethenyl, 1-propenyl, 2-propenyl, 1-, 2-, or 3-butenyl, and the like. An alkenyl group may be optionally substituted ("optionally substituted alkenyl"). Suitable substituent groups for alkenyl are as described herein for, "optionally substituted alkyl", "substituted alkyl" and alkyl.

"Alkynyl" refers to an alkyl group, as defined herein, consisting of at least two carbon atoms and at least one carbon-carbon triple bond. Alkynyl groups have 2 to 20 carbon atoms "(C2-C20)alkynyl", preferably 2 to 12 carbon atoms "(C2-C12)alkynyl", more preferably 2 to 8 carbon atoms "(C2-C8)alkynyl", or 2 to 6 carbon atoms "(C2-C6) alkynyl", or 2 to 4 carbon atoms "(C2-C4)alkynyl". Representative examples include, but are not limited to, ethynyl, 1-propynyl, 2-propynyl, 1-, 2-, or 3-butynyl, and the like. Any alkynyl groups may be optionally substituted. Suitable substituent groups for alkynyl are as described herein for, "optionally substituted alkyl", "substituted alkyl" and alkyl.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 fluorine atoms. Non-limiting examples of fluoroalkyl groups include —$CH_2F$, —$CHF_2$, and —$CF_3$. The term "(C1-C3) fluoroalkyl" refers to a fluoroalkyl group having from 1 to 3 carbon atoms. The term "(C1)fluoroalkyl" refers to —$CH_2F$, —$CHF_2$, and —$CF_3$.

The term "aryl" as used herein, refers to an aromatic monocyclic or multicyclic ring system comprising from 6 to about 14 carbon atoms. In one embodiment, an aryl group contains from about 6 to 10 carbon atoms (C6-C10)aryl. In another embodiment, an aryl group is phenyl. Non-limiting examples of aryl groups include phenyl and naphthyl. Aryl groups may be optionally substituted. Suitable substituent groups for aryl are as described herein for, "optionally substituted alkyl", "substituted alkyl" and alkyl.

The term "cycloalkyl," as used herein, refers to a saturated ring containing the specified number of ring carbon atoms, and no heteroatoms. Cycloalkyl substituents typically contain 3 to 8 carbon atoms "(C3-C8)cycloalkyl", preferably 3-7 carbon atoms "(C3-C7)cycloalkyl", more preferably 3 to 6 carbon atoms "(C3-C6)cycloalkyl", or 3 to 5 carbon atoms "(C3-C5)cycloalkyl". Non-limiting examples of monocyclic cycloalkyls include cyclopropyl, cyclobutyl, cyclopentyl, and cyclohexyl. All cycloalkyl groups described herein may be optionally substituted by one or more substituent groups, which are selected independently unless otherwise indicated. Cycloalkyl groups described herein as optionally substituted ("optionally substituted cycloalkyl") may be substituted by one or more substituents groups, which are selected independently unless otherwise indicated. Cycloalkyl groups described herein as substituted cycloalkyl ("substituted cycloalkyl") will be substituted with one or more substituent groups, which are selected independently unless otherwise indicated. The total number of substituent groups may equal the total number hydrogen atoms on the cycloalkyl moiety, to the extent such substitution makes chemical sense. Optionally substituted cycloalkyl groups typically contain from 1 to 6 optional substituents, preferably from 1 to 4 optional substituents and more preferably from 1 to 3 optional substituents. For example, an optionally substituted cyclopropyl group is "optionally substituted (C3)cycloalkyl" and a substituted cyclopropyl group is "substituted (C2)cycloalkyl". In one embodiment a cycloalkyl group contains 3 to 9 carbon atoms, "(C3-C9)cycloalkyl". In another embodiment a substituted cycloalkyl group contains 3 to 9 carbon atoms, "substituted (C3-C9)cycloalkyl". Suitable substituent groups for cycloalkyl are as described herein for, "optionally substituted alkyl", "substituted alkyl" and alkyl.

The term "cycloalkenyl" as used herein, refers to partially unsaturated carbocyclic ring system containing the specified number of carbon atoms. Cycloalkenyl substituents typically contain 4 to 8 carbon atoms "(C4-C8)cycloalkenyl" and preferably 5-6 carbon atoms "(C5-C6)cycloalkenyl". Non-limiting examples of monocyclic cycloalkenyls include cyclobutenyl, cyclopentenyl, cyclohexenyl, and cycloheptenyl. Cycloalkenyl groups described herein may be optionally substituted with one or more substituent groups, which are selected independently unless otherwise indicated. The total number of substituent groups may equal the total number of hydrogen atoms on the cycloalkenyl moiety, to the extent such substitution makes chemical sense. Optionally substituted cycloalkenyl groups typically contain from 1 to 6 optional substituents, preferably from 1 to 4 optional substituents and more preferably from 1 to 3 optional substituents. For example, a cyclopentenyl group is "(C5) cycloalkenyl" and an optionally substituted cyclopentenyl group is "optionally substituted (C5)cycloalkenyl". In one embodiment a cycloalkenyl group contains 4 to 8 carbon atoms, "(C4-C8)cycloalkenyl". Suitable substituent groups for cycloalkenyl are as described herein for, "optionally substituted alkyl", "substituted alkyl" and alkyl.

The term "cycloalkylalkyl" as used herein, refers to a cycloalkyl ring, typically a (C3-C9)cycloalkyl, which is connected to the base molecule through an alkylene linker of 1 to 6 carbon atoms "(C1-C6)alkylene". Cycloalkylalkyl groups are described by the number of carbon atoms in the carbocyclic ring and the number of carbon atoms in the linker. Cycloalkylalkyl groups described herein may be optionally substituted with one or more substituents groups, which are selected independently unless otherwise indicated. Cycloalkylalkyl groups described herein as optionally substituted ("optionally substituted cycloalkylalkyl") may be substituted by one or more substituent groups, which are selected independently unless otherwise indicated. Cycloalkylalkyl groups described herein as substituted cycloalkylalkyl ("substituted cycloalkylalkyl") will be substituted with one or more substituent groups, which are selected independently unless otherwise indicated. The total number of substituent groups may equal the total number of hydrogen atoms on the cycloalkylalkyl moiety, to the extent such substitution makes chemical sense. Optionally substituted cycloalkylalkyl groups typically contain from 1 to 6 optional substituents, preferably from 1 to 4 optional substituents and more preferably from 1 to 3 optional substituents. In one embodiment a cycloalkyl group contains 3 to 9 carbon atoms and the linker alkyl group contains 1 to 6 carbon atoms, "(C3-C9)cycloalkyl(C1-C6)alkyl". For example, cyclopropylethyl group is "(C3)cycloalkyl(C2)alkyl" and an optionally substituted cyclopropylethyl group is "optionally substituted (C3)cycloalkyl(C2)alkyl". In addition, a substituted cyclopropylethyl group is "substituted (C3)cycloalkyl(C2) alkyl". Suitable substituent groups for cycloalkylalkyl are as described herein for, "optionally substituted alkyl", "substituted alkyl" and alkyl.

The term "cycloalkenylalkyl" as used herein, refers to a cycloalkenyl ring, typically a (C4-C8)cycloalkenyl, which is connected to the base molecule through an alkylene linker of 1 to 6 carbon atoms "(C1-C6)alkylene". Cycloalkenylalkyl groups are described by the number of carbon atoms in the carbocyclic ring and the number of carbon atoms in the linker. Thus a "(C5)cycloalkyenyl(C1)alkyl" group is a cyclopentenyl group connected to the base molecule though a methylene group ($—CH_2—$). Cycloalkenylalkyl groups described herein may be optionally substituted with one or more substituent groups, which are selected independently unless otherwise indicated.

The total number of substituent groups may equal the total number of hydrogen atoms on the cycloalkenylalkyl moiety, to the extent such substitution makes chemical sense. Optionally substituted cycloalkenylalkyl groups typically contain from 1 to 6 optional substituents, preferably from 1 to 4 optional substituents and more preferably from 1 to 3 optional substituents. In one embodiment a cycloalkenyl group contains 4 to 8 carbon atoms and the linker alkyl group contains 1 to 6 carbon atoms, "(C4-C8)cycloalkenyl (C1-C6)alkyl". For example, cyclopentenylethyl group is "(C5)cycloalkenyl(C2)alkyl" and an optionally substituted cyclopentenylethyl group is "optionally substituted (C5) cycloalkenyl(C2)alkyl". Suitable substituent groups for cycloalkenylalkyl are as described herein for, "optionally substituted alkyl", "substituted alkyl" and alkyl.

In some instances, substituted alkyl groups may be specifically named with reference to the substituent group. For example "haloalkyl" refers to an alkyl group having the specified number of carbon atoms that is substituted by one or more halo substituents, and typically contain 1 to 6 carbon atoms and 1, 2 or 3 halo atoms (i.e., "(C1-C6)haloalkyl"). Thus, a (C1-C4)haloalkyl group includes trifluoromethyl ($—CF_3$) and difluoromethyl ($—CF_2H$). Haloalkyl groups described herein may be optionally substituted with one or more substituent groups, which are selected independently unless otherwise indicated. The total number of substituent groups (the sum of the number of halo and any other substituents defined herein) may equal the total number of hydrogen atoms on the unsubstituted parent alkyl moiety, to the extent such substitution makes chemical sense. For example, for $—CH_2CH_2CH(OH)CH_2CF_3$ the parent alkyl moiety is N-pentyl ($—(CH_2)_4CH_3$) with 11 possible positions for substitution. This example is not meant to be limiting. Haloalkyl groups described herein as optionally substituted ("optionally substituted haloalkyl") may be substituted by one or more substituent groups, which are selected independently unless otherwise indicated. Haloalkyl groups described herein as substituted haloalkyl ("substituted haloalkyl") will be substituted with one or more substituent groups, which are selected independently unless otherwise indicated. The total number of substituent groups may equal the total number hydrogen atoms on the haloalkyl moiety, to the extent such substitution makes chemical sense. Optionally substituted haloalkyl groups typically contain from 1 to 6 optional substituents, preferably from 1 to 4 optional substituents and more preferably from 1 to 3 optional substituents. For example, an optionally substituted halopropyl group is "optionally substituted (C3)haloalkyl" and a substituted halopropyl group is "substituted (C3) haloalkyl". In one embodiment a cycloalkyl group contains 1 to 6 carbon atoms, "(C1-C6)haloalkyl". In another embodiment a substituted haloalkyl group contains 1 to 6 carbon atoms, "substituted (C1-C6)haloalkyl". Suitable substituent groups for haloalkyl are as described herein for, "optionally substituted alkyl" and "substituted alkyl".

"Alkoxy" refers to a monovalent —O-alkyl group, wherein the alkyl portion has the specified number of carbon atoms. The alkyl portion of the alkoxy group, may be straight chain or branched chain groups. Alkoxy groups typically contain 1 to 8 carbon atoms "(C1-C8)alkoxy", or 1 to 6 carbon atoms "(C1-C6)alkoxy" or 1 to 4 carbon atoms "(C1-C4)alkoxy". Non-limiting examples of alkoxy groups include methoxy, ethoxy, n-propoxy, isopropoxy, n-butoxy and t-butoxy. All alkoxy groups described herein may be optionally substituted with one or more substituent groups, which are selected independently unless otherwise indicated. Alkoxy groups described herein as optionally substituted ("optionally substituted alkoxy") may be substituted by one or more substituent groups, which are selected independently unless otherwise indicated. Alkoxy groups described herein as substituted alkoxy ("substituted alkoxy") will be substituted with one or more substituent groups, which are selected independently unless otherwise indicated. The total number of substituent groups may equal the total number of hydrogen atoms on the alkoxy moiety, to the extent such substitution makes chemical sense. Optionally substituted alkoxy groups typically contain from 1 to 6 optional substituents, preferably from 1 to 4 optional substituents and more preferably from 1 to 3 optional substituents. For example, an optionally substituted ethoxy group is "optionally substituted (C2)alkoxy" and a substituted butoxy group is "substituted (C4)alkoxy". In one embodiment an alkoxy group contains 1 to 6 carbon atoms, "(C1-C6)alkoxy". In another embodiment a substituted alkoxy group contains 1 to 6 carbon atoms, "substituted (C1-C6) alkoxy". Suitable substituent groups for alkoxy are as described herein for, "optionally substituted alkyl", "substituted alkyl" and alkyl.

"Cycloalkoxy" refers to a monovalent —O-cycloalkyl group, wherein the cycloalkyl portion has the specified number of carbon atoms. The cycloalkyl portion of the alkoxy group, typically contain 3 to 9 carbon atoms "(C3-C9)cycloalkoxy", or 3 to 6 carbon atoms "(C3-C6)cycloalkoxy". Non-limiting examples of cycloalkoxy groups include cyclopropoxy, cyclobutoxy and cyclopentoxy. All cycloalkoxy groups described herein may be optionally substituted with one or more substituent groups, which are selected independently unless otherwise indicated. The total number of substituent groups may equal the total number of hydrogen atoms on the cycloalkoxy moiety, to the extent such substitution makes chemical sense. Optionally substituted cycloalkoxy groups typically contain from 1 to 6 optional substituents, preferably from 1 to 4 optional substituents and more preferably from 1 to 3 optional substituents. Suitable substituent groups for cycloalkoxy are as described herein for, "optionally substituted alkyl", "substituted alkyl" and alkyl.

The term "haloalkoxy" refers to a monovalent —O-haloalkyl group wherein the alkyl portion has the specified number of carbon atoms that are substituted by one or more halo substituents, and typically contain 1 to 6 carbon atoms and 1, 2 or 3 halo atoms (i.e., "(C1-C6)haloalkoxy") In some instances, substituted alkyl groups may be specifically named with reference to the substituent group. For example "haloalkoxy" refers to an alkyl group having the specified number of carbon atoms. Thus, a (C1-C4)haloalkoxy group includes trifluoromethoxy (—$OCF_3$). Haloalkoxy groups described herein may be substituted by one or more substituent groups, which are selected independently unless otherwise indicated. The total number of substituent groups may equal the total number of hydrogen atoms on the haloalkyl moiety, to the extent such substitution makes chemical sense. Optionally substituted haloalkoxy groups typically contain from 1 to 3 optional substituents and preferably from 1 to 2 optional substituents. In one embodiment a haloalkoxy group contains 1 to 6 carbon atoms, "(C1-C6)haloalkoxy". An example of a substituted haloalkoxy group contains 1 to 6 carbon atoms, "(C1-C6) haloalkoxy". Suitable substituent groups for haloalkyloxy are as described herein for, "optionally substituted alkyl" and "substituted alkyl".

The term "halo" as used herein, means —F, —Cl, —Br or —I. In one embodiment, a halo group is —Cl. In another embodiment, a halo group is —Br.

The term "halogen" as used herein, means —F, —Cl, —Br or —I. In one embodiment, a halogen group is —Cl. In another embodiment, a halogen group is —Br.

The term "acyl" as used herein means —C(O)alkyl or —C(O)cycloalkyl. The alkyl group may be straight chain or branched chain groups. Alkyl substituent of an acyl group typically contain 1 to 20 carbon atoms, preferably 1-12 carbon atoms, more preferably 1 to 8 carbon atoms, 1 to 6 carbon atoms, or 1 to 4 carbon atoms. The cycloalkyl substituent of an acyl group typically contain 3 to 8 carbon atoms, preferably 3-7 carbon atoms, more preferably 3 to 6 carbon atoms, or 3 to 5 carbon atoms. The alkyl and cycloalkyl moieties of an acyl group may be substituted. Suitable substituent groups are as described herein for, "optionally substituted alkyl", "substituted alkyl" and alkyl.

The term "aryl" or "aromatic" refer to an optionally substituted monocyclic biaryl or fused bicyclic ring systems, having the well-known characteristics of aromaticity, wherein at least one ring contains a completely conjugated pi-electron system. Typically, aryl groups contain 6 to 20 carbon atoms, "(C6-20)aryl" as ring members, preferably 6 to 14 carbon atoms "(C6-C14)aryl" or more preferably 6 to 12 carbon atoms "(C6-C12)aryl". Fused aryl groups may include an aryl ring (e.g., a phenyl ring) fused to another aryl ring, or fused to a saturated or partially unsaturated carbocyclic or heterocyclic ring. The point of attachment to the base molecule on such fused aryl ring systems may be a carbon atom of the aromatic portion or a carbon or nitrogen atom of the non-aromatic portion of the ring system. Example, without limitation, of aryl groups include phenyl, biphenyl, naphthyl, anthracenyl, phenanthrenyl, indanyl, indenyl, and tetrahydronaphthyl. Aryl groups described herein may be optionally substituted with one or more substituents groups, which are selected independently unless otherwise indicated. Suitable substituent groups for the aryl group are further described herein.

The term "heteroaryl" or heteroaromatic" may be used interchangeably herein, to refer to an aromatic monocyclic or multicyclic ring system comprising about 5 to about 14 ring atoms, wherein from 1 to 4 of the ring atoms is independently N, O, or S and the remaining ring atoms are carbon atoms. These systems having the well-known characteristics of aromaticity. Heteroaryl rings are attached to the base molecule via a ring atom of the heteroaromatic ring, such that aromaticity is maintained. The inclusion of a heteroatom permits aromaticity in 5-membered rings as well as 6 membered rings. In one embodiment, a heteroaryl group has 5 to 10 ring atoms. In another embodiment, a heteroaryl group is a monocyclic ring system and has 5 to 6 ring atoms. In another embodiment, a heteraryl group is a bicyclic ring system. The term "heteroaryl" also includes a heteroaryl, as defined above, fused to a heterocyclyl as defined below. The term "heteroaryl" also encompasses a heteroaryl group, as defined above, which is fused to a benzene, a cyclohexadiene or a cyclohexane ring. Non-limiting examples of heteroaryls include pyridyl, pyrazinyl, furanyl, thienyl, pyrimidinyl, pyridine (including N-substituted pyridines), isoxazolyl, isothiazolyl, oxazolyl, oxadiazolyl, thiazolyl, pyrazonyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo[2,1-b]thiazolyl, and alike. Heteroaryl or heteroaromatic groups described herein may be optionally substituted with one or more substituents groups, which are selected independently unless otherwise indicated. Suitable substituent groups for the heteroaryl or heteroaromatic groups are further described herein.

The terms "heterocyclyl", "heterocyclic" or "heteroalicyclic" may be used interchangeably herein, to refer to a non-aromatic saturated or partially saturated monocyclic or multicyclic ring system containing 3 to 11 ring atoms, wherein from 1 to 4 of the ring atoms are independently O, S, or N and the remainder of the ring atoms are carbon atoms. In one embodiment, a heterocyclic group is monocyclic and has 6 ring atoms, "6-membered heterocyclic ring". In another embodiment, a heterocyclic group is monocyclic and has 6 ring atoms with either 1 or 2 ring atoms being a heteroatom, "6-membered heterocyclic ring containing 1 or 2 heteroatoms". In another embodiment, a heterocyclic group is monocyclic and has either 4 or 5 ring atoms, "4- or 5-membered heterocyclic ring". In another embodiment, a heterocyclic group has 7, 8 or 9 ring atoms, "7-, 8- or 9-membered heterocyclic ring". In another embodiment, a heterocyclic group is bicyclic. A heterocyclic group can be joined to the rest of the molecule via a ring carbon or ring nitrogen atom. The nitrogen or sulphur atom of the heterocyclyl can be optionally oxidized to the corresponding N-oxide, S-oxide or S,S-dioxide. Any carbon atom bearing two hydrogens may be optionally oxidized to the corresponding carbonyl. Non-limiting examples of the monocyclic heterocyclic rings include oxetanyl, piperidyl, pyrrolidinyl, piperazinyl, morpholinyl, thiomorpholinyl, thiazolidinyl, dihydropyranyl, pyran, 1,4-dioxanyl, tetrahydrofuranyl, tetrahydrothiophenyl, delta-lactam, delta-lactone and the like. Heterocyclic groups described herein may be optionally substituted with one or more substituents groups, which are selected independently unless otherwise indicated. Suitable substituent groups for the heterocyclic groups are further described herein. Heterocyclic groups may be unsubstituted or substituted by the same groups suitable for alkyl, aryl or heteroaryl. In one embodiment a heterocyclic ring contains 6 atoms and is substituted with 1 to 4 groups as defined herein, "6-membered heterocyclic ring substituted with one to four groups". In addition, ring nitrogen atoms may be optionally substituted, when specified, by groups suitable for an amine, e.g., alkyl, acyl, carbamoyl, sulfonyl substituents, etc., and ring S atoms may be optionally substituted by 1 or 2 oxo groups (i.e., $S(O)_q$, where q is 0, 1 or 2). In one embodiment a 4 or 5 membered heterocyclic ring is optionally substituted, as given above, "optionally substituted 4- or 5-membered heterocyclic ring". In another embodiment, a 7, 8- or 9-membered heterocyclic ring is optionally substituted, as given above, "optionally substituted 7-, 8- or 9-membered heterocyclic ring".

Aryl, heteroaryl and heterocyclic moieties described herein as optionally substituted ("optionally substituted") may be substituted by one or more substituent groups, which are selected independently unless otherwise indicated. Aryl, heteroaryl and heterocyclic moieties described herein as substituted ("substituted") are substituted by one or more substituent groups, which are selected independently unless otherwise indicated. Optionally substituted aryl, heteroaryl or heterocyclic groups typically contain from 1 to 5 optional substituents, sometimes 1 to 4 optional substituents, preferably 1 to 3 optional substituents, or more preferably 1-2 optional substituents. Substituted aryl, heteroaryl or heterocyclic groups contain at least one substituent as described herein and may optionally contain up to 5 total substituents each independently selected. The substituent groups used are the substituent groups suitable for use as described herein.

Substituent groups suitable for aryl, heteroaryl and heterocyclic rings include, but are not limited to: (C1-C8)alkyl, (C2-C8)alkenyl, (C2-C8)alkynyl, (C3-C8)cycloalkyl, 3-12 membered heterocyclyl, (C6-C12)aryl, 5-12 membered heteroaryl, halo, =O (oxo), =S (thiono), =N—CN, =N—$OR^X$, =$NR^X$, —CN, —C(O)$R^X$, —$CO_2R^X$, —C(O)$NR^XR^Y$, —$SR^X$, —$SOR^X$, —$SO_2R^X$, —$SO_2NR^XR^Y$, —$NO_2$, —$NR^XR^Y$, —$NR^X$C(O)$R^Y$, —$NR^X$C(O)$NR^XR^Y$, —$NR^X$C(O)$OR^X$, —$NR^XSO_2R^Y$, —$NR^XSO_2NR^XR^Y$, —$OR^X$, —OC(O)$R^X$ and —OC(O)$NR^XR^Y$; where in each $R^X$ and $R^Y$ is independently hydrogen, (C1-C6)alkyl, (C2-C6)alkenyl, (C2-C6)alkynyl, (C3-C6)cycloalkyl, 3-12 membered heterocyclyl, (C6-C12)aryl, or 5-12 membered heteroaryl, or $R^X$ and $R^Y$ may be taken together with the nitrogen atom to which they are attached to form a 3-12 membered heterocyclyl or 5-12 membered heteroaryl system, each optionally containing 0, 1 or 2 additional heteroatoms; each $R^X$ and $R^Y$ is optionally substituted with 1 to 3 substituents independently selected from the group consisting of halo, =O, —CN, —C(O)R', —$CO_2$R', —C(O)$NR'_2$, —$SO_2$R', —$NR'_2$, —OR', wherein each R' is independently hydrogen, (C1-C6)alkyl, (C3-C6)cycloalkyl, or 3-12 membered heterocyclyl. However, suitable substituent for "substituted alkyl" does not include hydrogen.

"Unsubstituted amino" refers to a group —$NH_2$. Where the amino is described as substituted or optionally substituted, the term includes groups of the form —$NR_XR_Y$, where each $R^X$ and $R^Y$ is independently selected from hydrogen, (C1-C8)alkyl, (C3-C9)cycloalkyl, alkynyl, heterocyclyl, acyl, aryl, heteroaryl, thioacyl, cycloalkylalkyl, arylalkyl, or heteroalkylalkyl, in each case having the specified number of atoms and optionally substituted as described herein. Typically, alkyl substituents on amines contain 1 to 8 carbon atoms, preferably 1 to 6 carbon atoms, or more preferably 1 to 4 carbon atoms. The term also includes forms wherein $R_X$ and $R_Y$ are taken together with the nitrogen to which they are attached to form a 3-12 membered heterocyclyl or 5-12 membered heteroaryl ring, each of which may be optionally substituted as described herein for heterocyclyl or heteroaryl rings and which may contain 1 to 3 additional heteroatoms selected from N, O, and S as ring members, provided that such rings do not contain contiguous oxygen atoms or contiguous sulphur atoms. The term, as described above, extends to the amino residue of another functional group (for example, —C(O)$NR_XR_Y$, —$S(O)_2NR_XR_Y$, and alike). In one embodiment, $R_X$ and $R_Y$ of —$NR_XR_Y$; of —C(O)$NR_XR_Y$, may be taken together with the nitrogen to which they are attached ("taken together with the nitrogen to which they are attached") to form a ring (a 3-12 membered heterocyclyl or 5-12 membered heteroaryl ring, each of which may be optionally substituted as described herein for heterocyclyl or heteroaryl rings and which may contain 1 to 3 additional heteroatoms selected from N, O, and S as ring members, provided that such rings do not contain contiguous oxygen atoms or contiguous sulphur atoms). In another embodiment, $R_X$ and $R_Y$ of —$NR_XR_Y$; of —$S(O)_2NR_XR_Y$, may be taken together with the nitrogen to which they are attached to form a ring (a 3-12 membered heterocyclyl or 5-12 membered heteroaryl ring, each of which may be optionally substituted as described herein for heterocyclyl or heteroaryl rings and which may contain 1 to 3 additional heteroatoms selected from N, O, and S as ring members, provided that such rings do not contain contiguous oxygen atoms or contiguous sulphur atoms).

Two adjacent substituents on a ring may be taken together, with the atoms to which they are attached, to form a ring. The term "together with the carbon atoms to which they are attached may form a ring" is defined herein to mean two adjacent residues residing on a ring may be combined together with the carbon atoms to which they are attached to form a 4-6 membered heterocyclyl, a 4-6 membered carbocyclyl, or a 4-6 membered heteroaryl ring, each of which may be optionally substituted as described herein for heterocyclyl or heteroaryl rings. Thus formed heterocyclyl and heretoaryl rings may contain 1 to 3 additional heteroatoms selected from N, O, and S as ring members, (provided that such rings do not contain contiguous oxygen atoms or contiguous sulphur atoms). Representative examples derived from a phenyl moiety include, but are not limited to, benzofuranyl, benzothiophenyl, indolyl, benzimidazolyl, indazolyl, benzotrizolyl, indazolyl, quinolinyl, isoquinolinyl, cinnolinyl, azaquinazoline, quinoxalinyl, 2,3-dihydro-1H-indenyl, phthalanyl, 2,3-dihydrobenzofuryl, benzodioxoyl, benzodioxanyl, and the like. Representative examples thus formed hetereocyclyl rings include, but are not limited to:

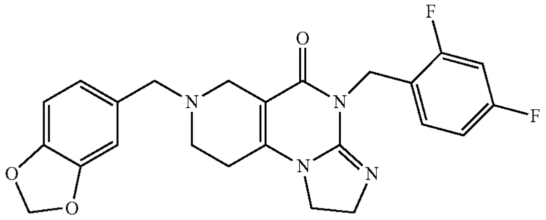 [SMILES: O=C1C2=C(CCN(Cc3ccc4c(c3)OCO4)C2)N2CCN=C2N1Cc1ccc(F)cc1F]

and alike. Representative examples thus formed carbocyclyl rings include, but are not limited to:

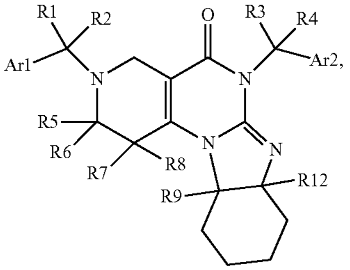

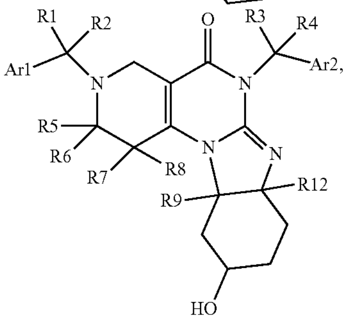

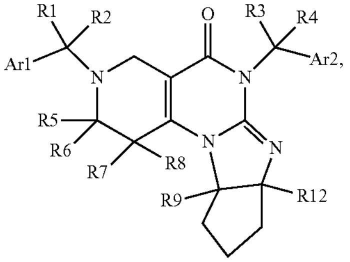

and alike.

Two substituents bound to a common carbon may be taken together with the carbon to which they are attached to form a ring. The term "together with the carbon to which they are attached may form a nonaromatic ring having 2 oxygen atoms" is defined herein to mean two alkoxy or two oxygen substituted alkyl groups may be combined with the carbon atom to which they are attached to form a ring of 4 to 7 atoms containing two oxygen atoms. Representative examples thus formed heterocyclic rings include but are not limited to:

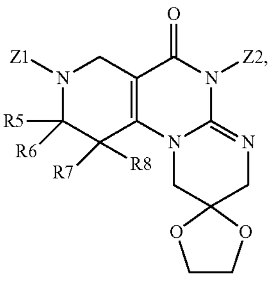

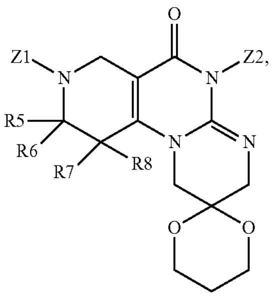

and alike.

Two substituents bound to a common nitrogen atom may be taken together, with the nitrogen to which they are attached, to form a ring. The term "together with the nitrogen atom to which they are attached may form a ring" is defined herein to mean two residues residing on a nitrogen atom may be combined together to form a 3-12-membered heterocyclyl, a 3-7-membered carbocyclyl, or a 5-12-membered heteroaryl ring, each of which may be optionally substituted as described herein for heterocyclyl or heteroaryl rings. Thus formed heterocyclyl and heteroaryl rings may contain 1 to 3 additional heteroatoms selected from N, O, and S as ring members, (provided that such rings do not contain contiguous oxygen atoms or contiguous sulphur atoms). Non-limiting examples derived from a nitrogen atom include the following moieties: azetidinyl, pyrrolidinyl, piperidinyl, morpholinyl, 1,4-azathianyl, 1,3,4-triazolyl, tetrazolyl, imidazolyl and alike.

Two substituents may be taken together to form an oxo residue (=O). "R5 and R6 may be taken together to form =O" means an oxygen atom is double bonded to the carbon atom that had both R5 and R6 residues. For A1 that would result in the following substructure, see 1AA. In addition, for "R7 and R8 may be taken together to form =O" means an oxygen atom is double bonded to the carbon atom that had both R7 and R8 residues, see 1 AB.

1AA

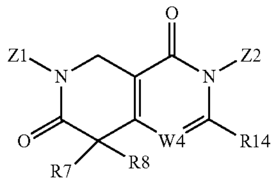

1AB

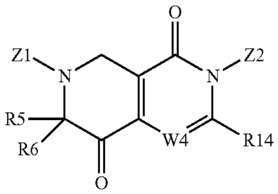

The term "substituted" means that one or more hydrogen atoms of the designated are replaced with a selection from the indicated group, provided that the atoms' normal valencies under the existing circumstances are not exceeded, and that the substitution results in a stable compound. By "stable compound" or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form" as used herein, refers to the physical state of a compound after the compound is isolated from a synthetic process (e.g., from a reaction mixture), a natural source, or a combination thereof. The term "in purified form" also refers to the physical state of a compound after the compound is obtained from a purification process or processes described herein or well-known to the skilled artisan (e.g., chromatography, recrystallization and the like).

The term optionally substituted alkyl with dye ("optionally substituted alkyl with dye") means that an alkyl residue may be substituted with the substituents defined for an optionally substituted alkyl residue, define herein, and either the carbon of the alkyl residue or a suitable substituent may be modified with a dye. As part of the dye residue there may be a linker moiety such as an alkyl chain or a poly ether chain. Compounds described by when Q is either Q2 or Q3 may be coupled with various infrared, fluorescent, phosphorescent, radioactive or infrared fluorescent as shown in Synthetic Scheme 3. Compounds shown as SS10 are valuable intermediates for the fashioning compounds of this invention to other diagnostic agents. The length of the carbon linker determined by n can be 1-30 however n=1-5 is more optimal. These analogs are made as described above using an appropriate protecting groups for the terminal functionality. The amine terminus of the alkyl chain has particular value as a reactive species and can easily fashion many common functional groups such as: amides, carbamates, secondary amines, etc., using acid chlorides, ketenes, carboxylic acids (with coupling agents) and alike. Other terminal residues in addition to the amine may be used to fashion linkers, such as —SH, —OH, —Cl, —Br and —I. These terminal residues may be linked to various dyes and imaging agents. Commercially available (BroadPharm, Inc, 6625 Top Gun Street, Suite 103, San Diego, CA 92121) fluorescent dyes containing a large variety of functional groups for easy of coupling and different length of PEG spacer for increased water solubility. Enable efficient biolabeling in imaging and diagnostic R&D. Classes of agents sold by BroadPharm, Inc include: BDP, Cyanine 3, Cyanine 5, Cyanine 5.5, Cyanine 7, fluorescein and pyrene. This example is not meant to be limiting.

It should be noted that any carbon as well as heteroatom with unsatisfied valences in the text, schemes, examples and tables herein is assumed to have the sufficient number of hydrogen atom(s) to satisfy the valences.

Compounds may be known by one or more designation. For example, ONC201 is also TIC10. Other compounds may be referred by a designation that begins with "TR". With regard to these agents the following example shows the nomenclature that refers to the same chemical compound. For example, the following refer to the same compound: TR57, TR-57, Tr57, Tr-57, tr-57 and tr57.

One or more compounds of the invention may exist in unsolvated as well as solvated forms with pharmaceutically acceptable solvents such as water, ethanol, and the like, and it is intended that the invention embrace both solvated and unsolvated forms.

The compounds of Formula (I) may contain one or more stereogenic centers and can thus occur as racemates, racemic mixtures, single enantiomers, diastereomeric mixtures and individual disatereomers. Each such asymmetric center will independently produce two optical isomers and it is intended that all of the possible optical isomers and diastereomers in mixtures and as pure or partially purified compounds are included within the ambit of this invention.

As used herein, the term "composition" is intended to encompass a product comprising the specified ingredients in the specified amounts, as well as any product which results, directly or indirectly, from combination of the specified ingredients in the specified amounts.

In the compounds of generic Formula (I) and compounds of the generic formulas, 1A, 2A, 3A, 4A, 5A, 6A, 7A, 8A, 9A, 10A, 11A, 12A, 13A, 14A, 15A and 16A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I) and compounds of the generic formulas, 1A, 2A, 3A, 4A, 5A, 6A, 7A, 8A, 9A, 10A, 11A, 12A, 13A, 14A, 15A and 16A. Enriching in a particular isotope may provide an advantageous characteristic(s), for example enriching for deuterium may afford certain therapeutic advantages, such as increasing in vivo half-life or reducing dosages. In addition, isotopic enrichment may also enrich a compound's usefulness in the characterization of biological samples. Compounds enriched in a specific isotope may be prepared via synthetic methods described herein and methods known to those skilled in the art by using reagents and starting material enriched with the specific isotope.

Prodrugs of the compounds of the invention are contemplated herein. The term "prodrug", as employed herein, denotes a compound which upon administration to a subject, undergoes chemical conversion by metabolic or chemical processes to yield a compound of Formula (I). Prodrugs may have beneficial properties, such as but not limited to, the enhancement of absorption and/or oral bioavailability.

The compounds of Formula (I) may in some cases form salts which are also with the scope of this invention. Reference to a compound of the formula (I) herein is understood to include reference to salts thereof, unless otherwise noted. The term "salt(s)" as used herein denotes acidic and/or basic salts formed with inorganic and/or organic acids and bases. Zwitterionic (internal or inner salts) are included within the term "salt(s)" as used herein (and may be formed, for example, where the R substituents comprise an acid moiety such as a carboxyl group). Also included herein are quaternary salts ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the Formula (I) may be formed, for example, by reacting a compound of Formula (I) by reacting a compound of Formula (I) with an equivalent amount of an acid or base in a medium such as one the allows for the precipitation of the salt (example, ether) or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example by P. Stahl et al, Camille G. (eds.) Handbook of Pharmaceutical Salts. Properties, Selection and Use. (2002) Zurich: Wiley-VCH. This disclosure is incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes compounds of Formula (I) in all their isolated forms.

This invention provides a method of determining whether a mammal is responsive to a compound of the general Formula I, the method comprising:

administering the compound of Formula I to an individual after isolating a pre-treatment biological sample, and before isolating a post-treatment biological sample of the sample type of biological sample, wherein the biological sample is selected from a blood sample, a serum sample, a plasma sample, a bone sample, a biopsy sample, a fine needle aspirate, a lymph node aspirate, a cystic aspirate, a paracentesis sample, a thoracentesis sample;

assaying the pre-treatment and post-treatment biological samples to determine the level of the biomarker ClpP and;

determining that the individual is a candidate for treatment with a compound of Formula I when the level of the pre-treatment biomarker is 1.5× or greater above normal levels, or determining if the individual is responsive to treatment with a compound of Formula I when either the level of the biomarker ClpP is reduced by greater than 50% of the pre-treatment biomarker;

Z1-Q Formula I

Z1 is:

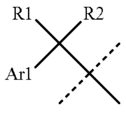

;

Z2 is:

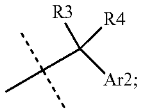

;

Q is independently selected from the group consisting of:

Q1

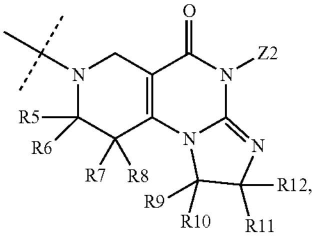

,

Q2

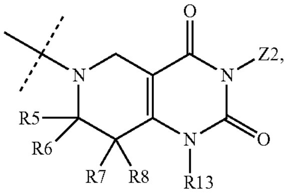

,

Q3

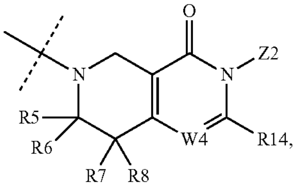

,

Q4

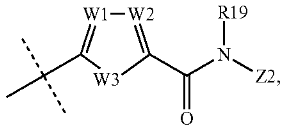

,

Q5

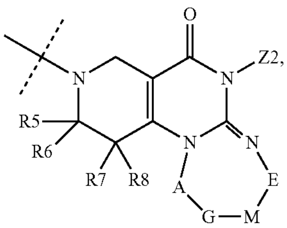

,

Q6

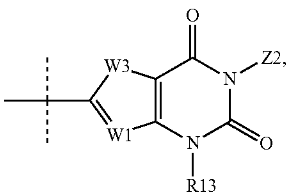

,

-continued

Q7

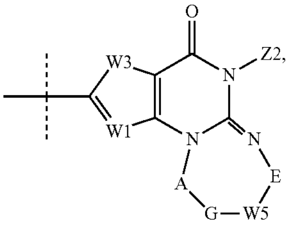

Q8

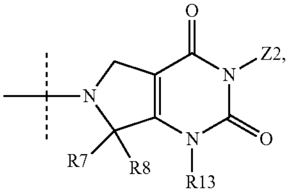

Q9

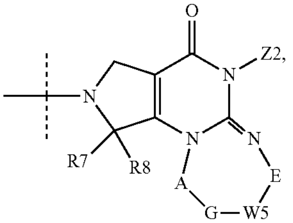

Q10

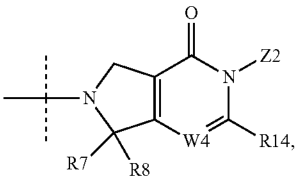

Q11

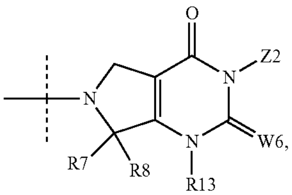

Q12

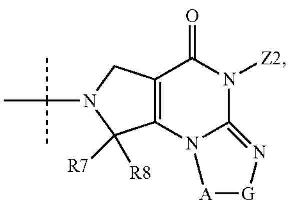

Q13

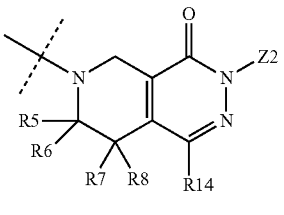

and

-continued

Q14

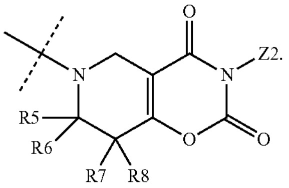

Ar1 and Ar2 are independently selected from aryl, heteroaryl, thiophenyl and phenyl;

Ar1 may be optionally substituted with from 1 to 5 J groups;

Ar2 is optionally substituted with from 1 to 5 JJ groups;

J is independently selected from halogen, —CN, (C1-C6) optionally substituted alkyl, (C3-C9) optionally substituted cycloalkyl, (C3-C9)cycloalkyl(C1-C6)alkyl, (C1-C6)haloalkyl, —$CF_3$, —$NH_2$, —$NO_2$, —SH, —SR15, —OH, (C1-C6) optionally substituted alkoxy, —NR17R18, substituted (C3-C9)cycloalkyl(C1-C6)alkyl, (C3-C9)cycloalkyl(C2-C6)alkynyl, (C4-C8)cycloalkenyl, (C4-C8)cycloalkenyl(C1-C6)alkyl, aryl, heteroaryl, heterocyclyl, optionally substituted aryl, optionally substituted heteroaryl, optionally substituted heterocyclyl, —C(O)OH, —C(O)OR15, —OC(O)OR15, (C2-C6)alkynyl, (C2-C8)alkenyl, (C1-C6)haloalkyoxy, —$S(O)_2$OR15, —$SO_2$NR17R18, —$S(O)_2$R15, —NR15$S(O)_2$R16, —C(O)NR17R18, —C(O)R15, and —NR15C(O)R16;

JJ is independently selected from hydrogen, halogen, —CN, (C1-C6) optionally substituted alkyl, (C3-C9) optionally substituted cycloalkyl, (C3-C9)cycloalkyl (C1-C6)alkyl, (C1-C6)haloalkyl, —$CF_3$, —$NH_2$, —$NO_2$, —SH, —SR15, —OH, (C1-C6) optionally substituted alkoxy, —NR17R18, substituted (C3-C9) cycloalkyl(C1-C6)alkyl, (C3-C9)cycloalkyl(C2-C6) alkynyl, (C4-C8)cycloalkenyl, (C4-C8)cycloalkenyl (C1-C6)alkyl, aryl, heteroaryl, —C(O)OH, —C(O)OR15, —OC(O)OR15, (C2-C6)alkynyl, (C2-C8) alkenyl, (C1-C6)haloalkyoxy, —$S(O)_2$OR15, —$SO_2$NR17R18, —$S(O)_2$R15, —NR15$S(O)_2$R16, —C(O)NR17R18, —C(O)R15, and —NR15C(O)R16;

R1, R2, R3, R4, R5, R6, R7 and R8 are each independently selected from hydrogen, halogen and (C1-C3) optionally substituted alkyl;

R9, R10, R11 and R12 are each independently selected from the group consisting of hydrogen, halogen, (C3-C6)cycloalkyl and (C1-C6) optionally substituted alkyl;

R10 and R11 together with the carbons atoms to which they are attached may form a nonaromatic ring having 3 to 6 carbon atoms;

R13 is independently selected from the group consisting of hydrogen, (C1-C6) optionally substituted alkyl, (C3-C6) optionally substituted cycloalkyl, (C1-C6)haloalkyl, (C2-C6) optionally substituted alkenyl, (C2-C6) optionally substituted alkynyl, —CN, —$S(O)_2$R15, —NR17R18, —$S(O)_2$R15, —C(NH)$NH_2$, —C(O)R15, ZW, and —C(O)OR15;

R14 is independently selected from hydrogen, (C1-C6) optionally substituted alkyl, (C3-C6)cycloalkyl, (C1-C6)haloalkyl, (C2-C6) optionally substituted alkenyl, (C2-C6) optionally substituted alkynyl, —CN, —$S(O)_2$R15, —NR17R18, —$S(O)_2$R15, —C(NH)$NH_2$, —C(O)R15, and —C(O)OR15;

R15, R16, R17, R18, R19, R28 and R29 are independently selected from hydrogen and (C1-C6) optionally substituted alkyl;

R17 and R18 together with nitrogen to which they are attached may form a ring of 3 to 6 atoms;

ZW is an (C1-C6) optionally substituted alkyl with dye;

W1 and W2 are independently selected from:

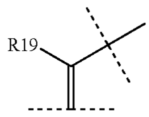

;

nitrogen and

W3 is independently selected from oxygen, —N(R15)-, and sulphur;

W4 is independently selected from the group consisting of =C(R14)- and nitrogen;

W5 is independently selected from the group consisting of a single bond, SS and

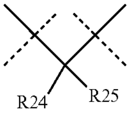

;

W6 is independently selected from the group consisting of oxygen, sulphur, and —NR14;

A is independently selected from the group consisting of SS and

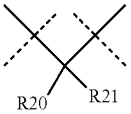

;

G is independently selected from the group consisting of SS and

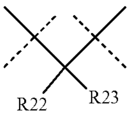

;

M is independently selected from the group consisting of SS and

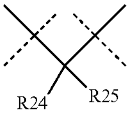

;

E is independently selected from the group consisting of a single bond, SS, and

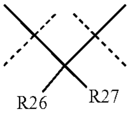

;

SS is independently selected from the group consisting of:

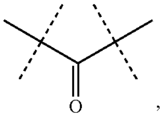

,

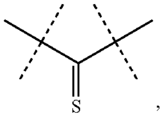

,

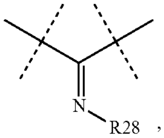

,

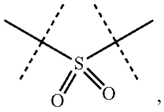

,

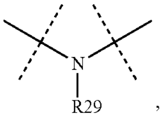

,

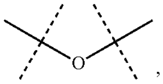

,

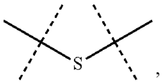

,

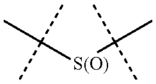

and

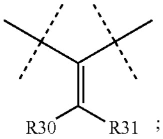

;

R20, R21, R26 and R27 are each independently selected from the group consisting of hydrogen, halogen and (C1-C6) optionally substituted alkyl;

R22, R23, R24 and R25 are each independently selected from the group consisting of hydrogen, halogen, —CN, (C1-C6) optionally substituted alkyl, (C3-C9) optionally substituted cycloalkyl, (C3-C9)cycloalkyl(C1-C6) alkyl, (C1-C6)haloalkyl, —$NH_2$, —$NO_2$, —SH, —SR15, —OH, (C1-C6) optionally substituted alkoxy, —NR17R18, substituted (C3-C9)cycloalkyl(C1-C6)alkyl, (C3-C9)cycloalkyl(C2-C6)alkynyl, (C4-C8)cycloalkenyl, (C4-C8)cycloalkenyl(C1-C6)alkyl, aryl, heteroaryl, —C(O)OH, —C(O)OR15, —OC(O)OR15, (C2-C6)alkynyl, (C2-C8)alkenyl, (C1-C6)haloalkyoxy, —$S(O)_2$OR15, —$SO_2$NR17R18, —$S(O)_2$R15, —NR15$S(O)_2$R16, —C(O)NR17R18, —C(O)R15, and —NR15C(O)R16;

R22 and R23 together with the carbon to which they are attached may form a nonaromatic ring having 3 to 6 carbon atoms;

R22 and R23 together with the carbon to which they are attached may form a nonaromatic ring having 1-2 oxygen atoms;

R24 and R25 together with the carbon to which they are attached may form a nonaromatic ring having 1-2 oxygen atoms;

R24 and R25 together with the carbon to which they are attached may form a nonaromatic ring having 3 to 6 carbon atoms;

R30 and R31 are each is independently selected from the group consisting of hydrogen and (C1-C6) optionally substituted alkyl.

Embodiments of this invention include testing the level of ClpP ex vivo in the sample taken from a mammal.

Embodiments of this invention include the sample to be tested is derived from normal tissue, tumor tissue, circulating tumor cells, plasma or whole blood.

Embodiments of this invention include the sample to be tested is derived from tumor tissue or circulating tumor cells.

Embodiments of this invention include a higher level of ClpP in a naive sample relative to a standard value or a set of standard values predicts efficacious response of said disease to treatment of a compound of formula I or pharmaceutically acceptable formulations thereof.

Embodiments of this invention include a lower level of ClpP in a sample relative to a standard value or a set of standard values after treatment of a compound of formula I or pharmaceutically acceptable formulations thereof predicts an efficacious response.

Embodiments of this invention include other biomarkers as described in this invention. These include the use of positive biomarkers described herein. In addition, this invention may use negative biomarkers. Also, negative biomarkers described herein may be used.

This invention provides compounds of Formula 1A:

1A

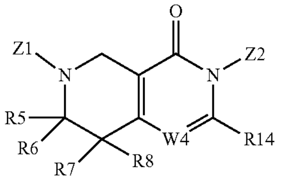

or pharmaceutically acceptable salt thereof.

This invention provides compounds of Formula 2A:

2A

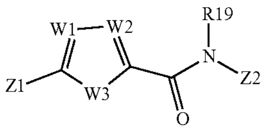

or pharmaceutically acceptable salt thereof.

This invention provides compounds of Formula 3A:

3A

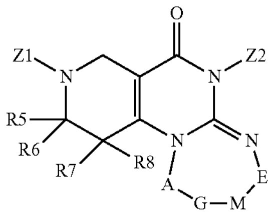

or pharmaceutically acceptable salt thereof.

This invention provides compounds of Formula 4A:

4A

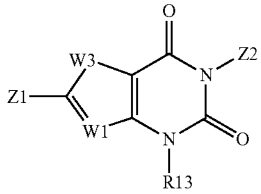

or pharmaceutically acceptable salt thereof.

This invention provides compounds of Formula 5A:

5A

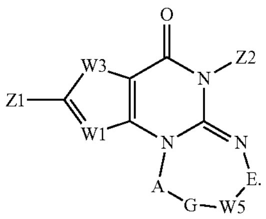

or pharmaceutically acceptable salt thereof.

This invention provides compounds of Formula 6A:

6A

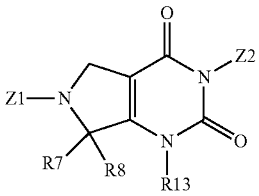

or pharmaceutically acceptable salt thereof.

This invention provides compounds of Formula 7A:

7A

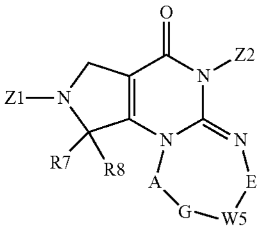

or pharmaceutically acceptable salt thereof.

This invention provides compounds of Formula 8A:

8A

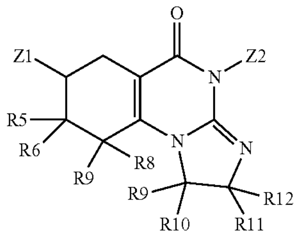

or pharmaceutically acceptable salt thereof.

This invention provides compounds of Formula 9A:

9A

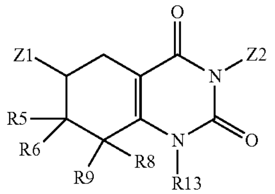

or pharmaceutically acceptable salt thereof.

This invention provides compounds of Formula 10A:

10A

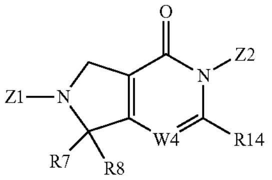

or pharmaceutically acceptable salt thereof.

This invention provides compounds of Formula 11A:

11A

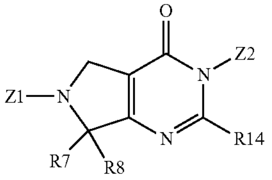

or pharmaceutically acceptable salt thereof.

This invention provides compounds of Formula 12A:

12A

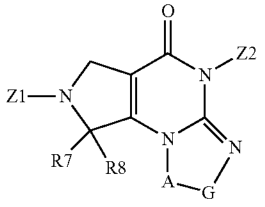

or pharmaceutically acceptable salt thereof.

This invention provides compounds of Formula 13A:

13A

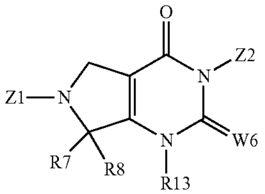

or pharmaceutically acceptable salt thereof.

This invention provides compounds of Formula 14A:

14A

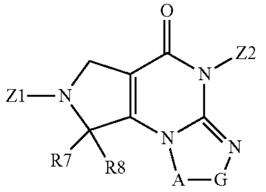

or pharmaceutically acceptable salt thereof.

This invention provides compounds of Formula 15A:

15A

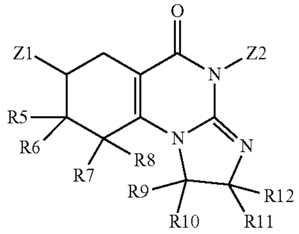

or pharmaceutically acceptable salt thereof.

This invention provides compounds of Formula 16A:

16A

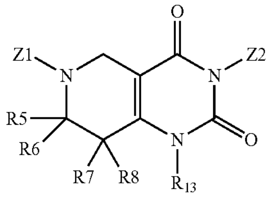

or pharmaceutically acceptable salt thereof.

This invention provides compounds of Formula 17A:

17A

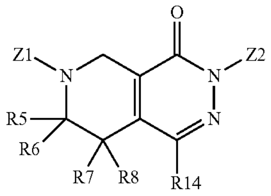

or pharmaceutically acceptable salt thereof.

This invention provides compounds of Formula 18A:

18A

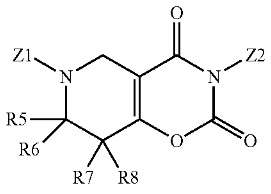

or pharmaceutically acceptable salt thereof.

The various radicals and or variables for 1A, 2A, 3A, 4A, 5A, 6A, 7A, 8A, 9A, 10A, 11A, 12A, 13A, 14A, 15A, 16A, 17A and 18A are defined herein as for Formula (I).

In another embodiment the present invention provides for the compounds and pharmaceutically acceptable salts of the formulas 1A, 2A, 3A, 4A, 5A, 6A, 7A, 8A, 9A, 10A, 11A, 12A, 13A, 14A, 15A, 16A, 17A and 18A.

In another embodiment the present invention provides for the compounds and pharmaceutically acceptable salts of the formulas 1A, 2A, 3A, 4A, 5A, 6A, 7A, 8A, 9A, 10A, 11A, 12A, 13A, 14A, 15A, 16A, 17A and 18A wherein:

Z1 is:

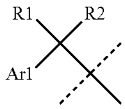

;

Z2 is:

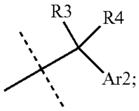

;

Ar1 and Ar2 are independently selected from aryl, heteroaryl, thiophenyl and phenyl;

Ar1 may be optionally substituted with from 1 to 5 J groups;

Ar2 is optionally substituted with from 1 to 5 JJ groups;

J is independently selected from halogen, —CN, (C1-C6) optionally substituted alkyl, (C3-C9) optionally substituted cycloalkyl, (C3-C9)cycloalkyl(C1-C6)alkyl, (C1-C6)haloalkyl, —$CF_3$, —$NH_2$, —$NO_2$, —SH, —SR15, —OH, (C1-C6) optionally substituted alkoxy, —NR17R18, substituted (C3-C9)cycloalkyl(C1-C6)alkyl, (C3-C9)cycloalkyl(C2-C6)alkynyl, (C4-C8)cycloalkenyl, (C4-C8)cycloalkenyl(C1-C6)alkyl, aryl, heteroaryl, heterocyclyl, optionally substituted aryl, optionally substituted heteroaryl, optionally substituted heterocyclyl, —C(O)OH, —C(O)OR15, —OC(O)OR15, (C2-C6)alkynyl, (C2-C8)alkenyl, (C1-C6)haloalkyoxy, —$S(O)_2OR15$, —$SO_2NR17R18$, —$S(O)_2R15$, —$NR15S(O)_2R16$, —C(O)NR17R18, —C(O)R15, and —NR15C(O)R16;

JJ is independently selected from hydrogen, halogen, —CN, (C1-C6) optionally substituted alkyl, (C3-C9) optionally substituted cycloalkyl, (C3-C9)cycloalkyl(C1-C6)alkyl, (C1-C6)haloalkyl, —$CF_3$, —$NH_2$, —$NO_2$, —SH, —SR15, —OH, (C1-C6) optionally substituted alkoxy, —NR17R18, substituted (C3-C9)cycloalkyl(C1-C6)alkyl, (C3-C9)cycloalkyl(C2-C6)alkynyl, (C4-C8)cycloalkenyl, (C4-C8)cycloalkenyl(C1-C6)alkyl, aryl, heteroaryl, —C(O)OH, —C(O)OR15, —OC(O)OR15, (C2-C6)alkynyl, (C2-C8)alkenyl, (C1-C6)haloalkyoxy, —$S(O)_2OR15$, —$SO_2NR17R18$, —$S(O)_2R15$, —$NR15S(O)_2R16$, —C(O)NR17R18, —C(O)R15, and —NR15C(O)R16;

R1, R2, R3, R4, R5, R6, R7 and R8 are each independently selected from hydrogen, halogen and (C1-C3) optionally substituted alkyl;

R9, R10, R11 and R12 are each independently selected from the group consisting of hydrogen, halogen, (C3-C6)cycloalkyl and (C1-C6) optionally substituted alkyl;

R10 and R11 together with the carbons atoms to which they are attached may form a nonaromatic ring having 3 to 6 carbon atoms;

R13 is independently selected from the group consisting of hydrogen, (C1-C6) optionally substituted alkyl, (C3-C6) optionally substituted cycloalkyl, (C1-C6)haloalkyl, (C2-C6) optionally substituted alkenyl, (C2-C6) optionally substituted alkynyl, —CN, —$S(O)_2R15$, —NR17R18, —$S(O)_2R15$, —$C(NH)NH_2$, —C(O)R15, ZW, and —C(O)OR15;

R14 is independently selected from hydrogen, (C1-C6) optionally substituted alkyl, (C3-C6)cycloalkyl, (C1-C6)haloalkyl, (C2-C6) optionally substituted alkenyl, (C2-C6) optionally substituted alkynyl, —CN, —$S(O)_2$ R15, —NR17R18, —$S(O)_2R15$, —$C(NH)NH_2$, —C(O)R15, and —C(O)OR15;

R15, R16, R17, R18, R19, R28 and R29 are independently selected from hydrogen and (C1-C6) optionally substituted alkyl;

R17 and R18 together with nitrogen to which they are attached may form a ring of 3 to 6 atoms;

ZW is an (C1-C6) optionally substituted alkyl with dye;

W1 and W2 are independently selected from:

nitrogen and

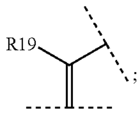

;

W3 is independently selected from oxygen, —N(R15)-, and sulphur;

W4 is independently selected from the group consisting of =C(R14)- and nitrogen;

W5 is independently selected from the group consisting of a single bond, SS and

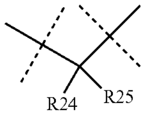

;

W6 is independently selected from the group consisting of oxygen, sulphur, and —NR14;

A is independently selected from the group consisting of SS and

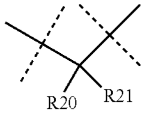

;

G is independently selected from the group consisting of SS and

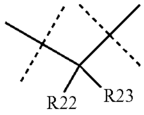

;

M is independently selected from the group consisting of SS and

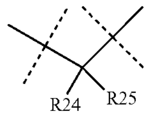 ;

E is independently selected from the group consisting of a single bond, SS, and

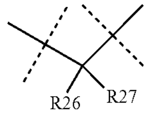 ;

SS is independently selected from the group consisting of:

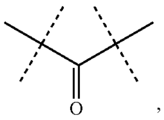 , 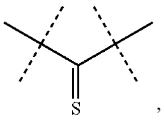 , 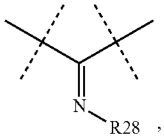 , 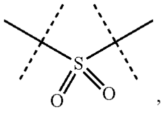 , 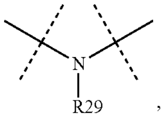 , 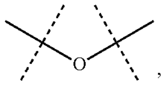 , 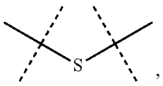 , 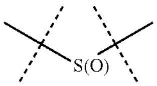 and 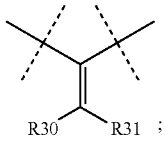 ;

R20, R21, R26 and R27 are each independently selected from the group consisting of hydrogen, halogen and (C1-C6) optionally substituted alkyl;

R22, R23, R24 and R25 are each independently selected from the group consisting of hydrogen, halogen, —CN, (C1-C6) optionally substituted alkyl, (C3-C9) optionally substituted cycloalkyl, (C3-C9)cycloalkyl(C1-C6) alkyl, (C1-C6)haloalkyl, —$NH_2$, —$NO_2$, —SH, —SR15, —OH, (C1-C6) optionally substituted alkoxy, —NR17R18, substituted (C3-C9)cycloalkyl(C1-C6)alkyl, (C3-C9)cycloalkyl(C2-C6)alkynyl, (C4-C8)cycloalkenyl, (C4-C8)cycloalkenyl(C1-C6)alkyl, aryl, heteroaryl, —C(O)OH, —C(O)OR15, —OC(O)OR15, (C2-C6)alkynyl, (C2-C8)alkenyl, (C1-C6)haloalkyoxy, —$S(O)_2OR15$, —$SO_2NR17R18$, —$S(O)_2R15$, —$NR15S(O)_2R16$, —C(O)NR17R18, —C(O)R15, and —NR15C(O)R16;

R22 and R23 together with the carbon to which they are attached may form a nonaromatic ring having 3 to 6 carbon atoms;

R22 and R23 together with the carbon to which they are attached may form a nonaromatic ring having 1-2 oxygen atoms;

R24 and R25 together with the carbon to which they are attached may form a nonaromatic ring having 1-2 oxygen atoms;

R24 and R25 together with the carbon to which they are attached may form a nonaromatic ring having 3 to 6 carbon atoms;

R30 and R31 are each is independently selected from the group consisting of hydrogen and (C1-C6) optionally substituted alkyl.

In another embodiment the present invention provides for the compounds and pharmaceutically acceptable salts of the formulas 1A, 2A, 3A, 4A, 5A, 6A, 7A, 8A, 9A, 10A, 11A, 12A, 13A, 14A, 15A, 16A, 17A and 18A wherein:

Z1 is

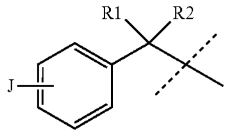

substituted with 0-5 J groups;

Z2 is

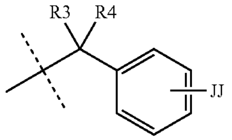

substituted with 1-5 JJ groups.

In another embodiment the present invention provides for the compounds and pharmaceutically acceptable salts of the formulas 1A, 2A, 3A, 4A, 5A, 6A, 7A, 8A, 9A, 10A, 11A, 12A, 13A, 14A, 15A, 16A, 17A and 18A wherein:

Z1 is

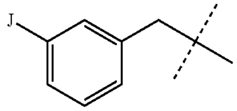

substituted with 1 J group;

Z2 is

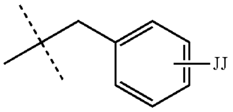

substituted with 1-5 JJ groups.

In another embodiment the present invention provides for the compounds and pharmaceutically acceptable salts of the formulas 1A, 2A, 3A, 4A, 5A, 6A, 7A, 8A, 9A, 10A, 11A, 12A, 13A, 14A, 15A, 16A, 17A and 18A wherein:

Z1 is

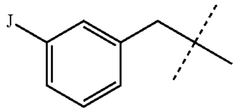 ;

substituted with 1 J group;

Z2 is

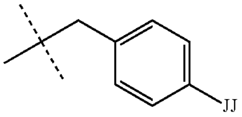

substituted with 1 JJ group.

In another embodiment the present invention provides for the compounds and pharmaceutically acceptable salts of the formulas 1A, 2A, 3A, 4A, 5A, 6A, 7A, 8A, 9A, 10A, 11A, 12A, 13A, 14A, 15A, 16A, 17A and 18A wherein:

Z1 is

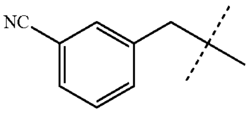

;

Z2 is

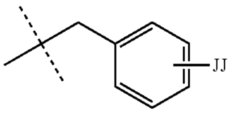

substituted with 1-5 JJ groups.

In another embodiment the present invention provides for the compounds and pharmaceutically acceptable salts of the formulas 1A, 2A, 3A, 4A, 5A, 6A, 7A, 8A, 9A, 10A, 11A, 12A, 13A, 14A, 15A, 16A, 17A and 18A wherein:

Z1 is

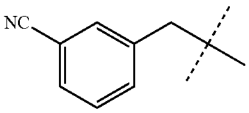

;

Z2 is

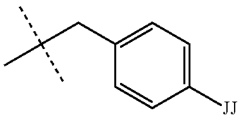

substituted with 1 JJ group.

In another embodiment the present invention provides for the compounds and pharmaceutically acceptable salts of the formulas 1A, 2A, 3A, 4A, 5A, 6A, 7A, 8A, 9A, 10A, 11A, 12A, 13A, 14A, 15A, 16A, 17A and 18A wherein:

Z1 is

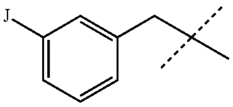

substituted with 1 J group;

Z2 is

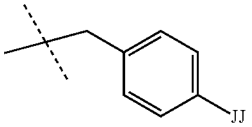

substituted with 1 JJ group;

R5, R6, R7, R8, R9, R10, R11 and R12 are hydrogen;

R14 is independently selected from hydrogen, (C1-C6) alkyl and —$NH_2$;

W1 and W2 are nitrogen;

W3 is independently selected from oxygen and sulphur;

W4 is independently selected from nitrogen and carbon;

W5 is independently selected from the group consisting of a single bond,

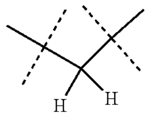

and

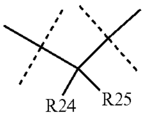

;

W6 is independently selected from oxygen, sulphur and $NH_2$;

R13 is independently selected from hydrogen and (C1-C6)alkyl;

A is

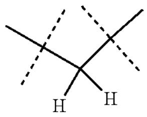

;

G is independently selected from

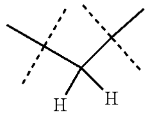

and

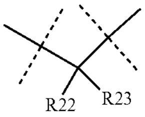

;

M is independently selected from the group consisting of

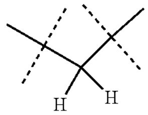

and

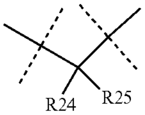

;

E is independently selected from the group consisting of a single bond,

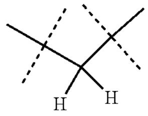

and

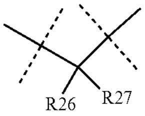

;

R14 is independently selected from hydrogen, (C1-C6) alkyl, and $NH_2$;

R19 is independently selected from hydrogen and (C1-C6)alkyl.

The methods of treating cancer described herein include a method for the treatment of cancer in a subject, comprising administering an effective amount of a compound of Formula 1A, 2A, 3A, 4A, 5A, 6A, 7A, 8A, 9A, 10A, 11A, 12A, 13A, 14A, 15A, 16A, 17A and 18A or a pharmaceutically acceptable salt thereof.

A pharmaceutical composition described herein, comprising a compound of Formula 1A, 2A, 3A, 4A, 5A, 6A, 7A, 8A, 9A, 10A, 11A, 12A, 13A, 14A, 15A, 16A, 17A and 18A or a pharmaceutically acceptable salt thereof, and a pharmaceutically acceptable carrier or excipient.

This invention also provides for the treatment of disease whereby the activation of ClpP would be effective. The methods described herein for the treatment of such disease would include the administration of a compound of the following Formulas: 1A, 2A, 3A, 4A, 5A, 6A, 7A, 8A, 9A, 10A, 11A, 12A, 13A, 14A, 15A, 16A, 17A and 18A or a pharmaceutically acceptable salt thereof. In addition, various neurodegenerative diseases may be treated with the compounds described herein. The methods described herein for the treatment of various neurodegenerative diseases would include the administration of a compound of the following Formulas: 1A, 2A, 3A, 4A, 5A, 6A, 7A, 8A, 9A, 10A, 11A, 12A, 13A, 14A, 15A, 16A, 17A and 18A or a pharmaceutically acceptable salt thereof. Also, the methods described herein for the treatment of Parkinson's disease, Huntington's disease, amyotrophic lateral sclerosis and Alzheimer's disease would include the administration of a compound of the following Formulas: 1A, 2A, 3A, 4A, 5A, 6A, 7A, 8A, 9A, 10A, 11A, 12A, 13A, 14A, 15A, 16A, 17A and 18A or a pharmaceutically acceptable salt thereof.

This invention also provides for the treatment of disease whereby the reduction in concentration and/or activity of ClpX would be effective. The methods described herein for the treatment of such disease would include the administration of a compound of the following Formulas: 1A, 2A, 3A, 4A, 5A, 6A, 7A, 8A, 9A, 10A, 11A, 12A, 13A, 14A, 15A, 16A, 17A and 18A or a pharmaceutically acceptable salt thereof. This invention also provides for the treatment of disease whereby the reduction in concentration and/or activity of TUFM would be effective. The methods described herein for the treatment of such disease would include the administration of a compound of the following Formulas: 1A, 2A, 3A, 4A, 5A, 6A, 7A, 8A, 9A, 10A, 11A, 12A, 13A, 14A, 15A, 16A, 17A and 18A or a pharmaceutically acceptable salt thereof.

In one embodiment of this invention the following compounds are anticipated to be activators of the protein ClpP. These compounds are formed via a selection of an FA2 fragment and the independent selection of fragments: FA1 and FA3 to form a single molecule. For FA1, Ar1 is phenyl which is optionally substituted with 1-5 J groups.

FA1:

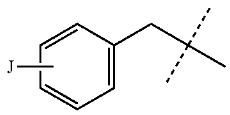

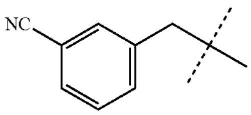

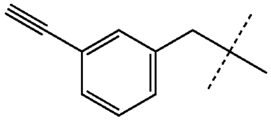

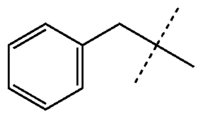

FA3:

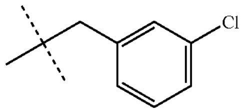

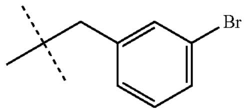

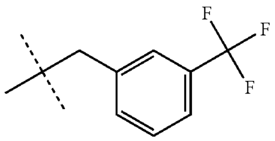

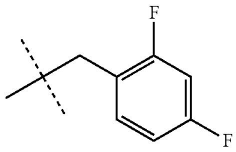

FA2:

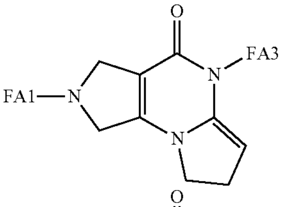

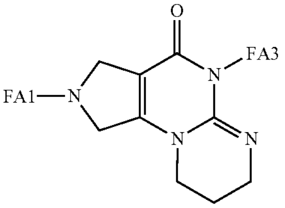

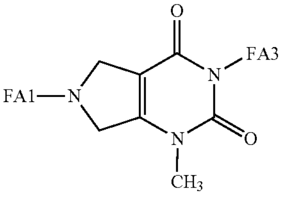

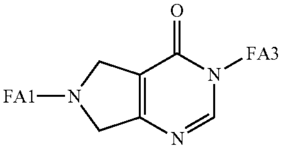

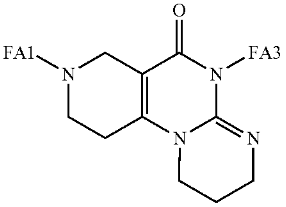

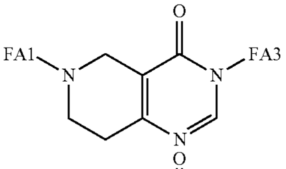

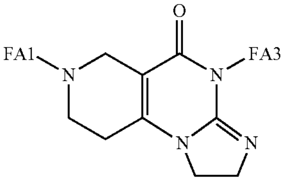

-continued
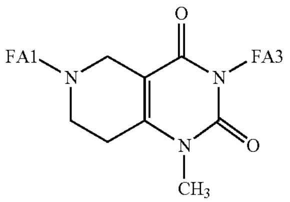
In another embodiment are compounds FA1-FA2-FA3.
In another embodiment preferred compounds of the invention are examples 66, 76 and 77.
This invention provides compounds:
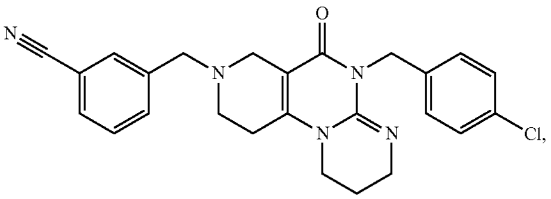
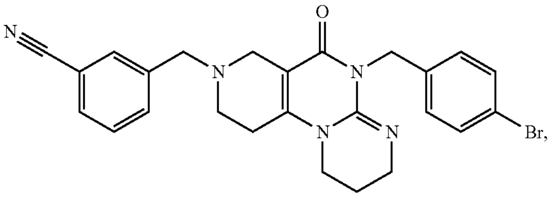
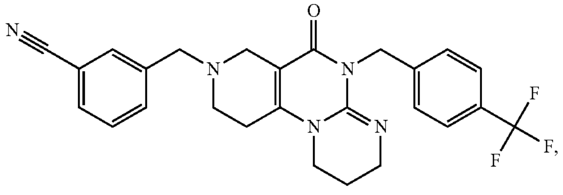
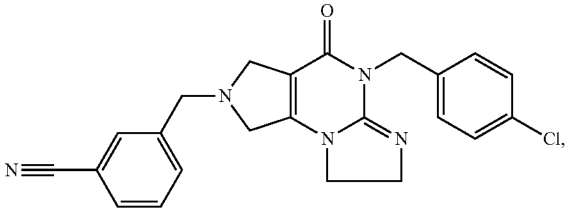
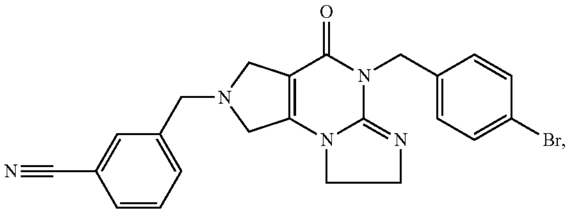
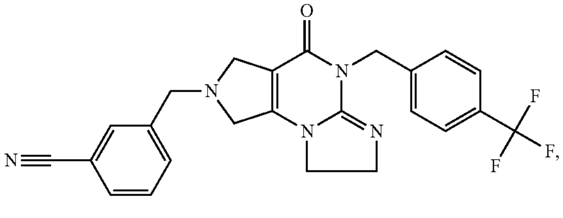
-continued
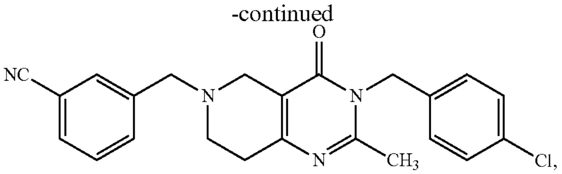
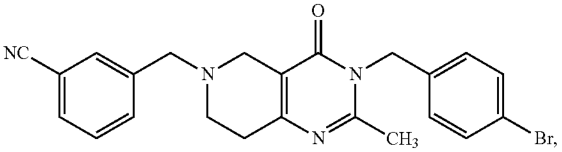
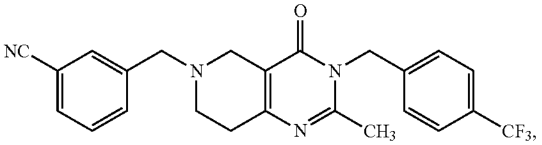
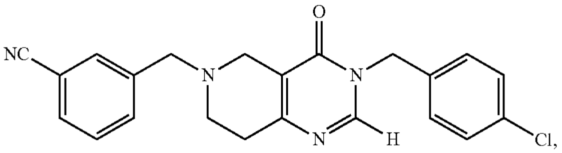
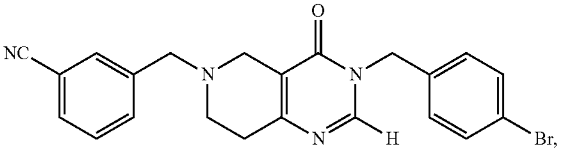
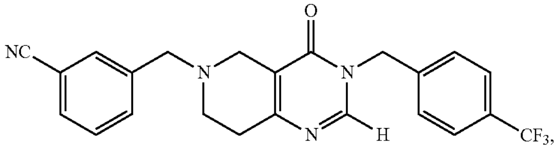
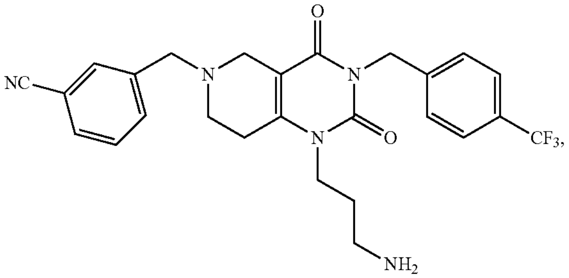
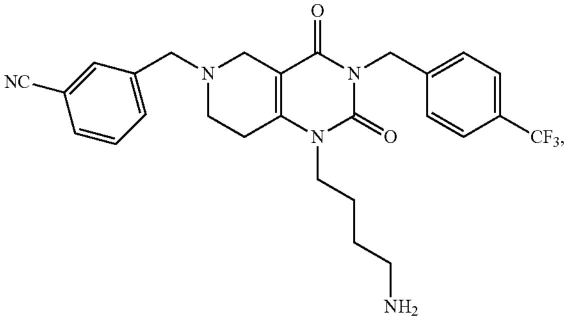

-continued
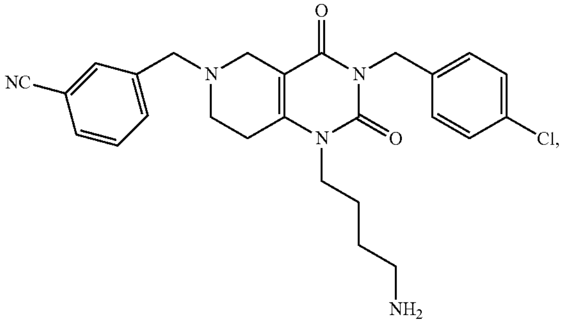
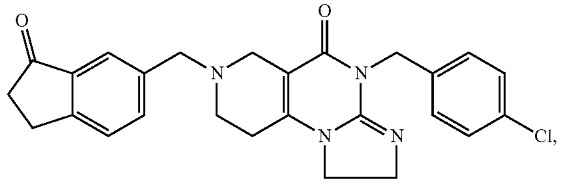
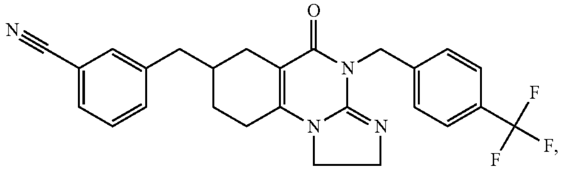
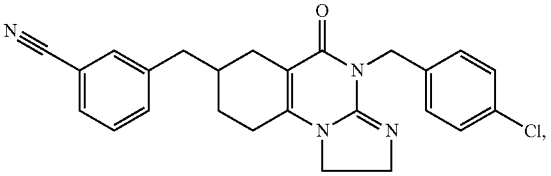
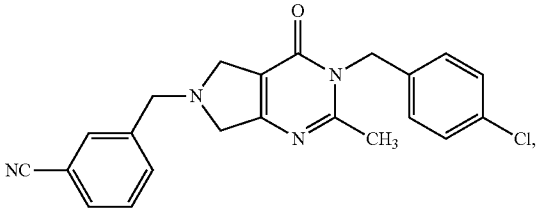
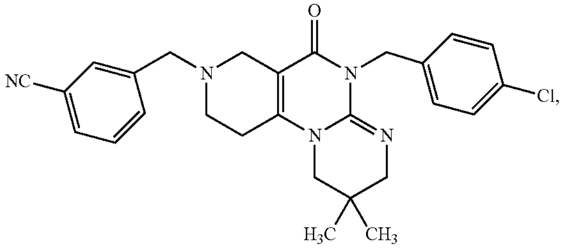
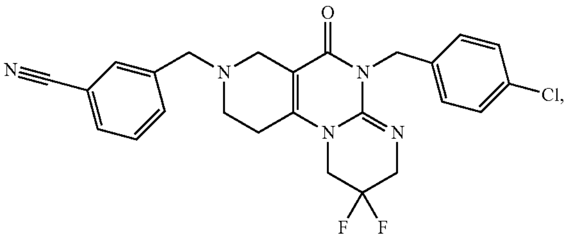
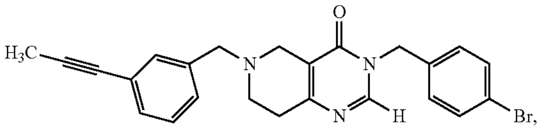
-continued
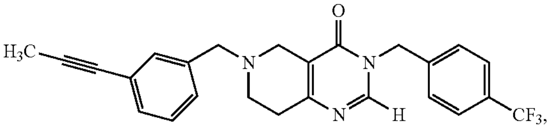
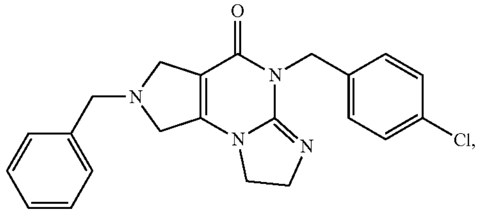
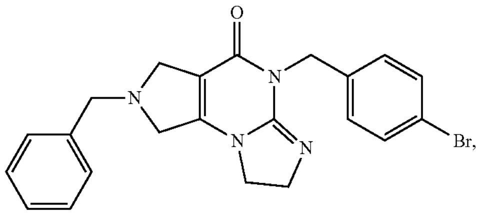
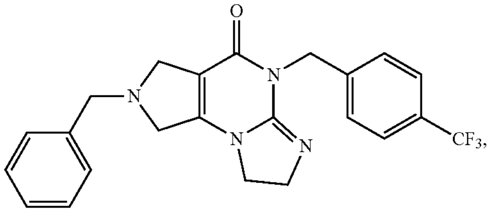
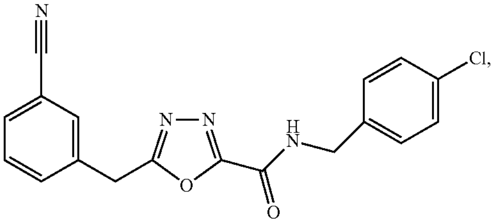
or a pharmaceutically acceptable salt thereof.
The methods of treating cancer described herein include a method for the treatment of cancer in a subject, comprising administering an effective amount of a compound:
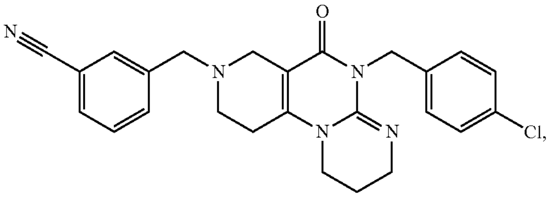
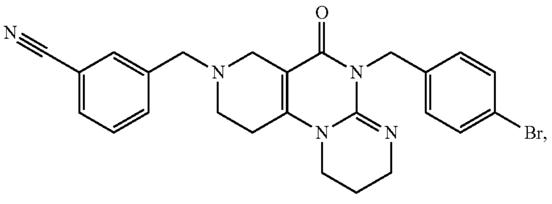

-continued
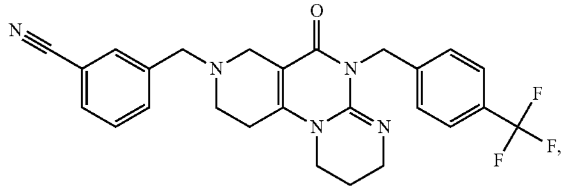
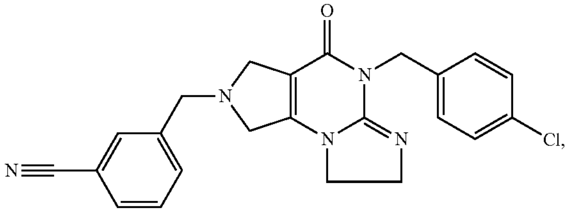
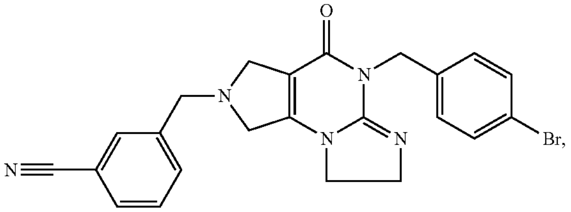
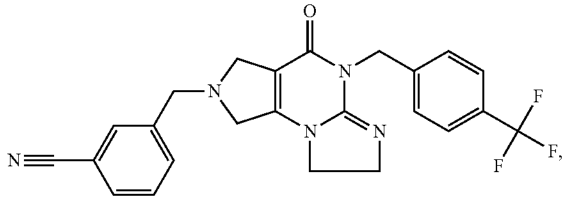
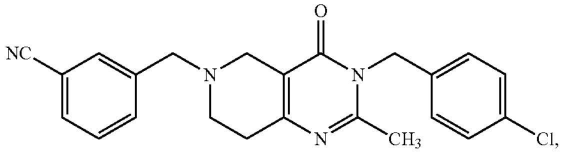
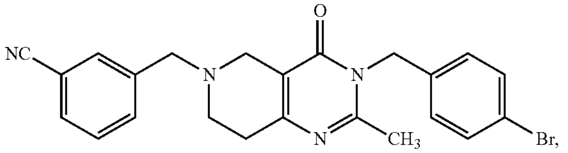
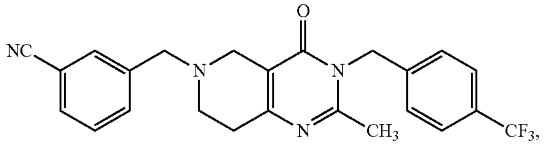
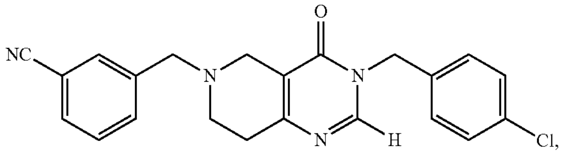
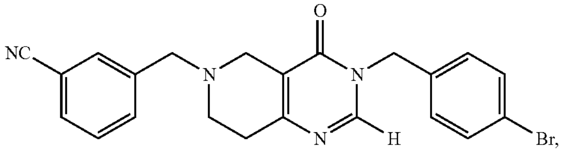
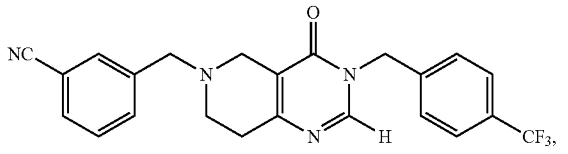
-continued
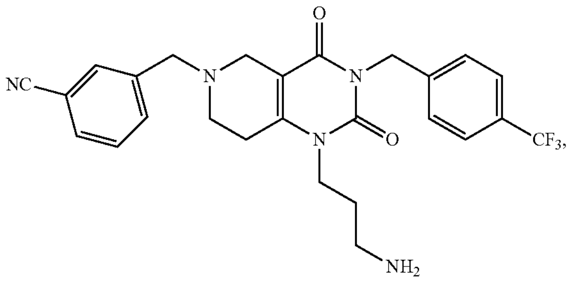
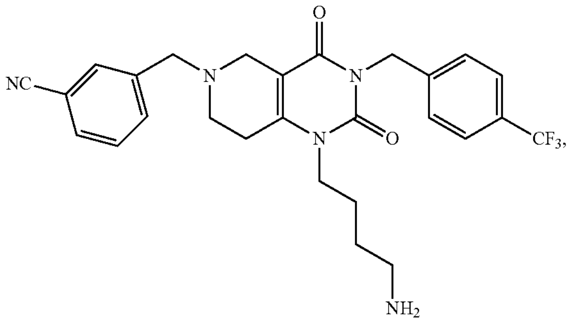
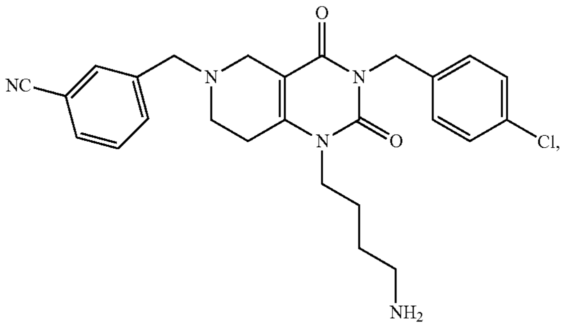
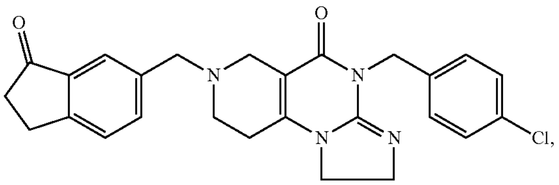
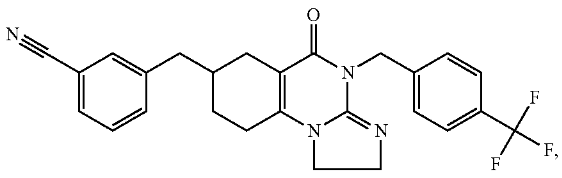
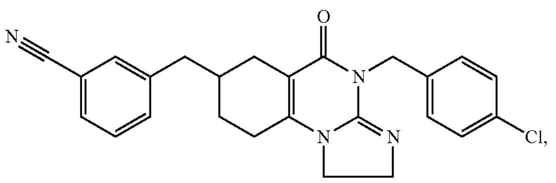
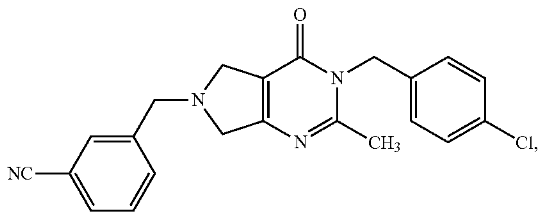

-continued
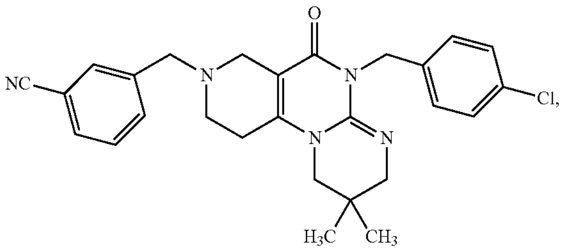
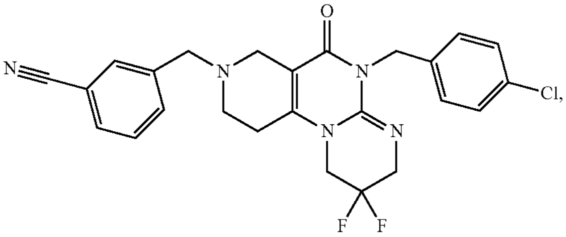
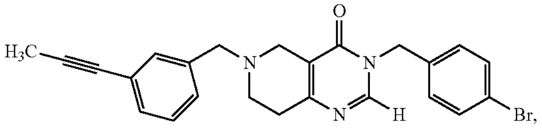
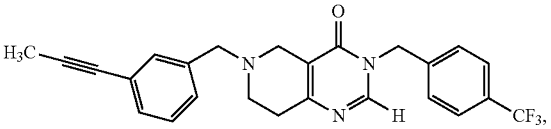
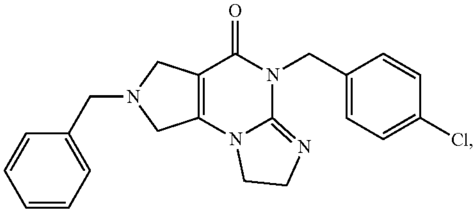
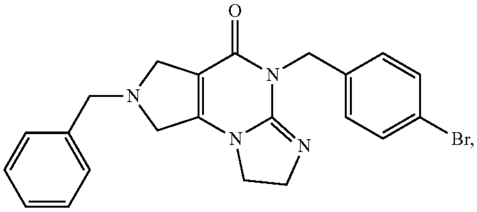
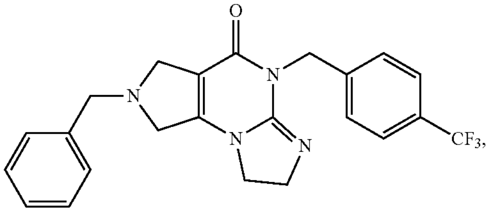
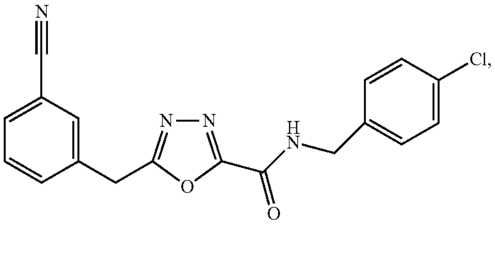
or a pharmaceutically acceptable salt thereof.
This invention anticipates the following compounds:
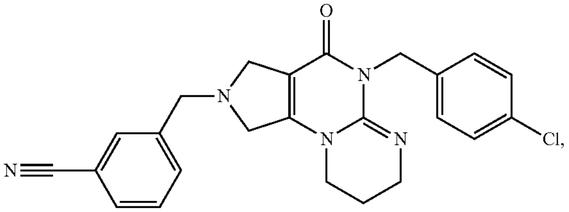
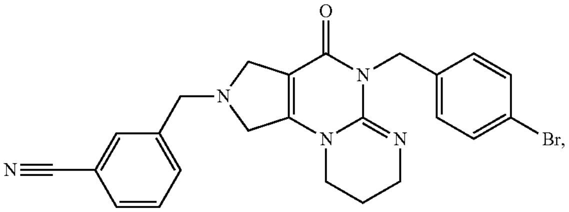
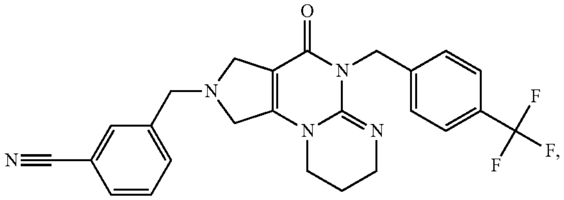
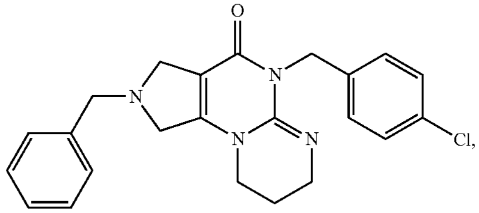
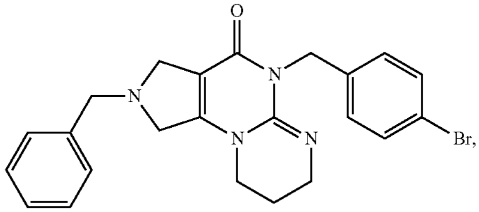
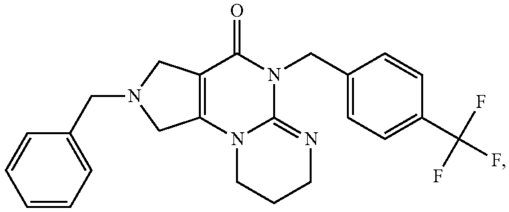
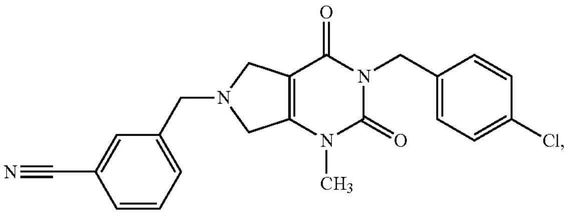
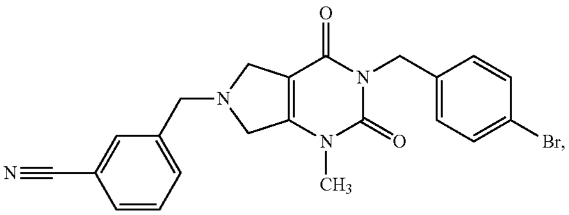

-continued
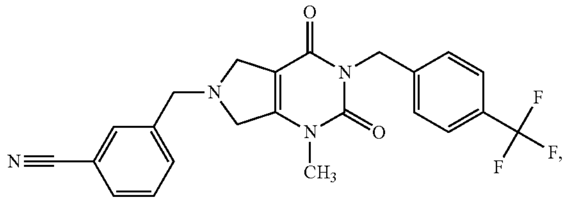
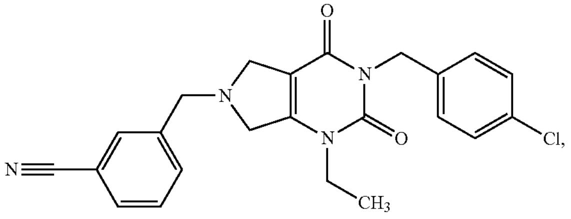
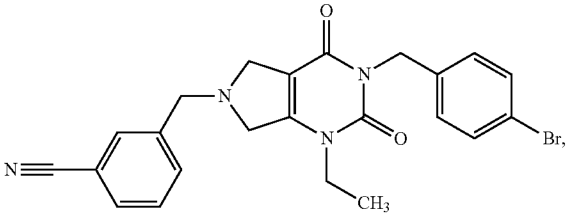
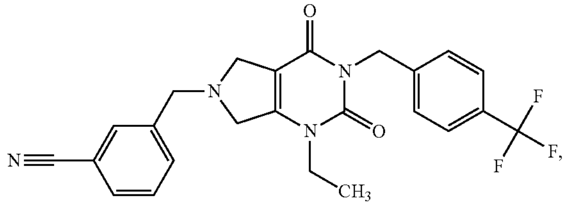
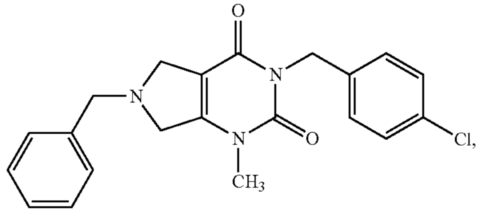
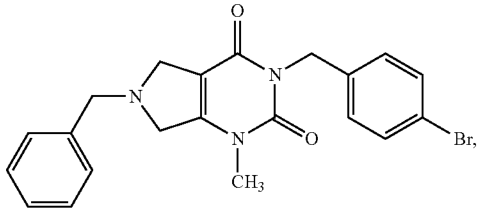
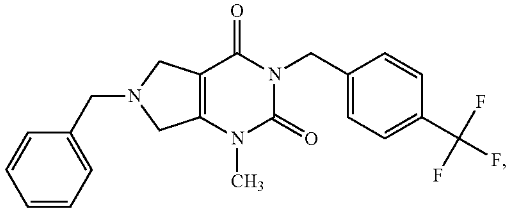
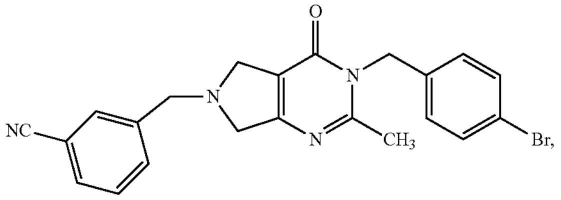
-continued
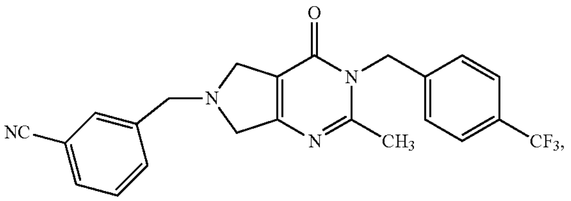
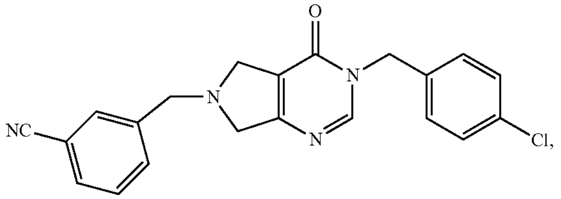
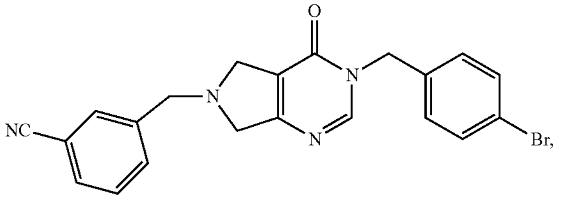
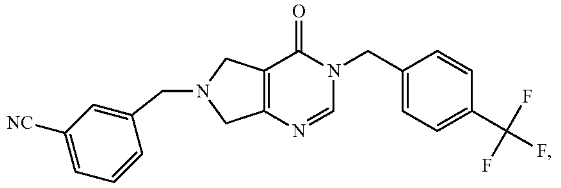
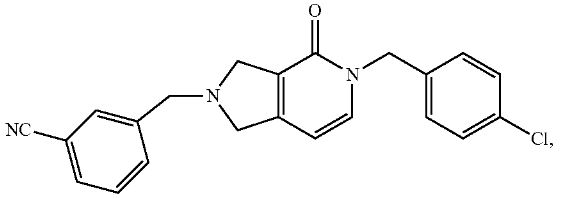
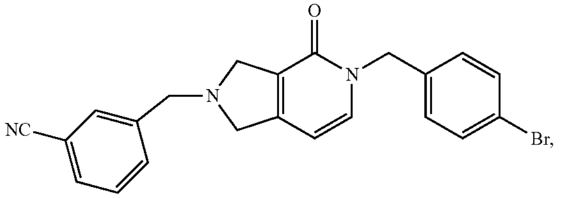
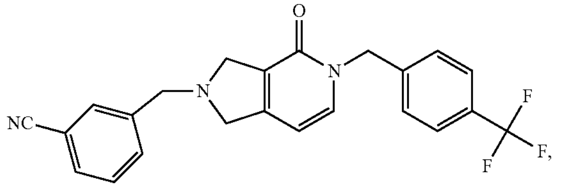
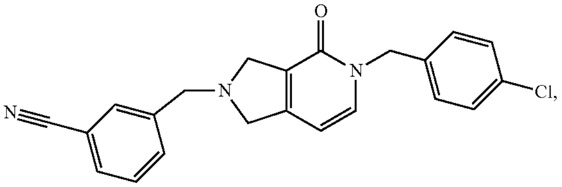
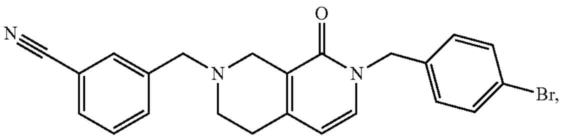

-continued
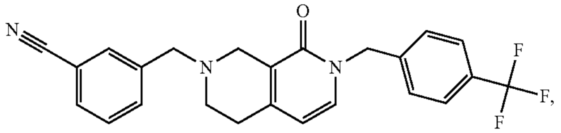
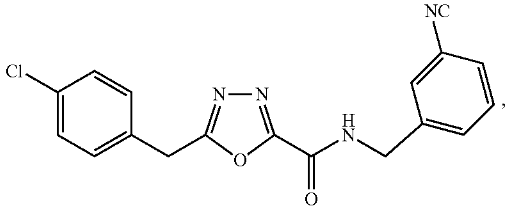
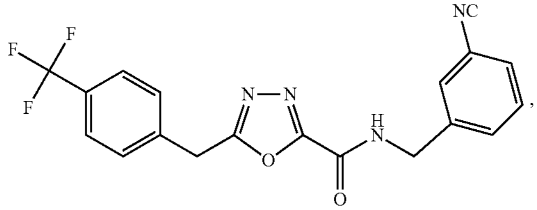
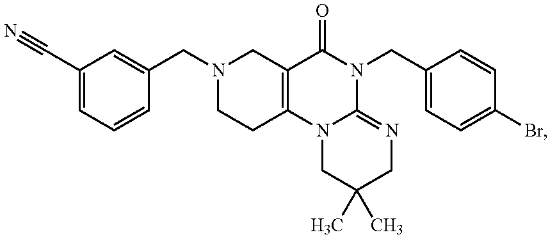
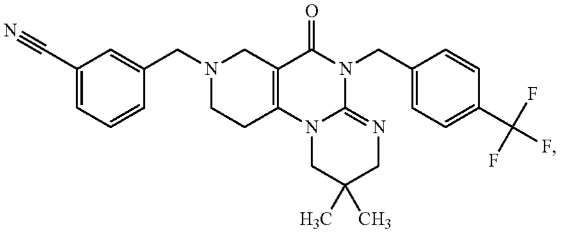
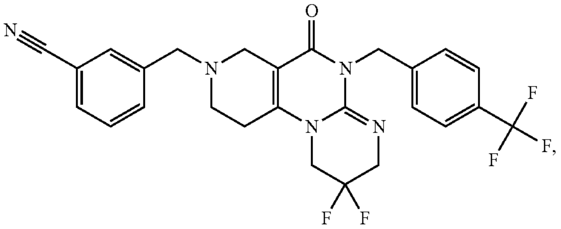
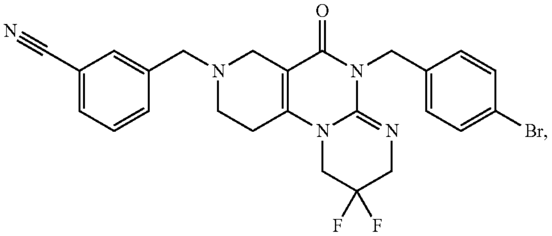
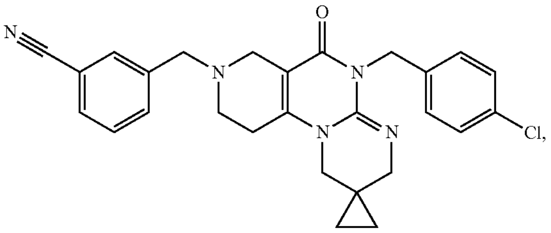
-continued
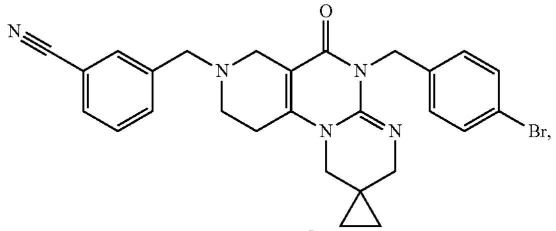
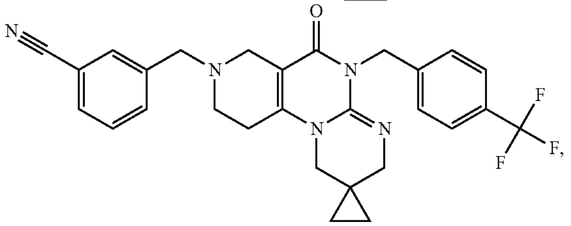
or a pharmaceutically acceptable salt thereof.
The anticipated methods of treating cancer described herein include a method for the treatment of cancer in a subject, comprising administering an effective amount of a compound:
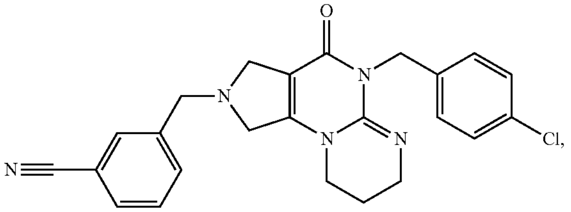
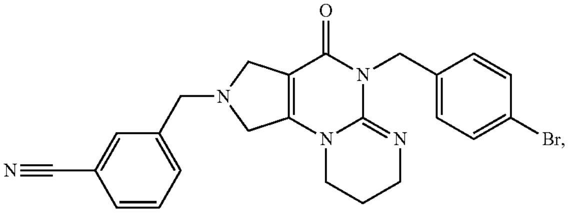
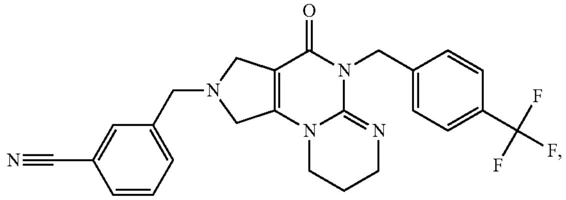
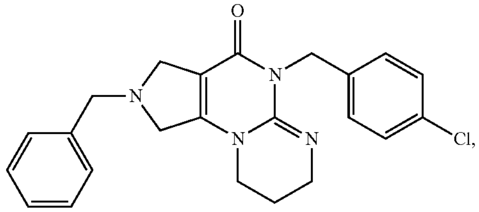
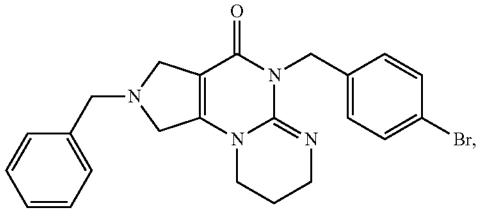

-continued
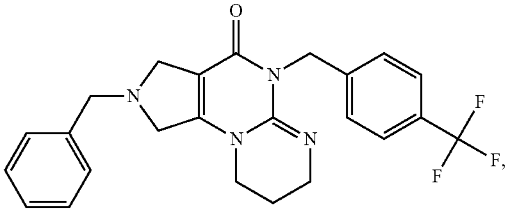,
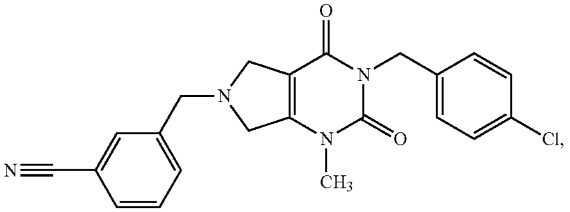,
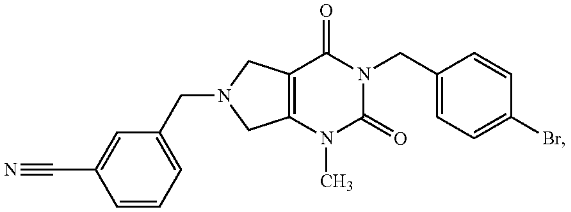,
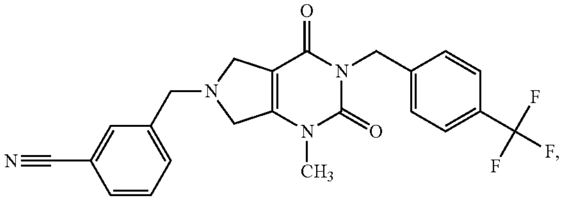,
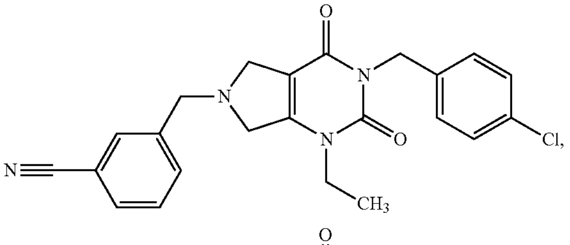,
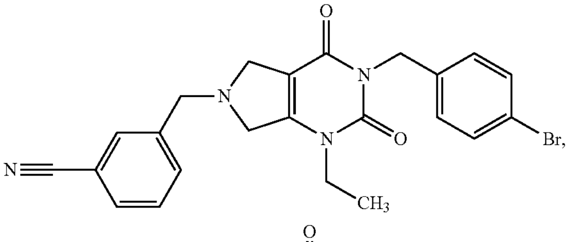,
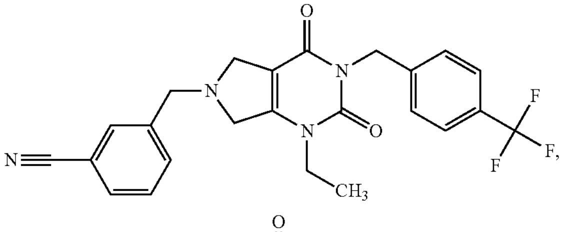,
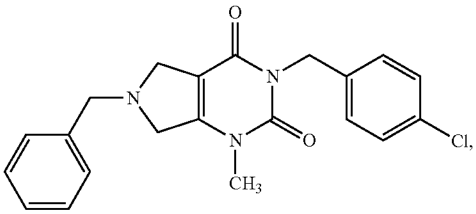,
-continued
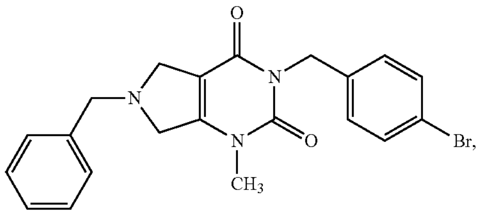,
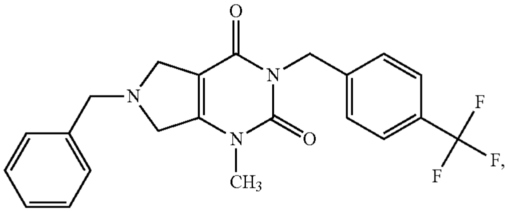,
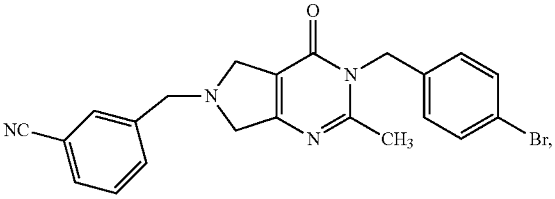,
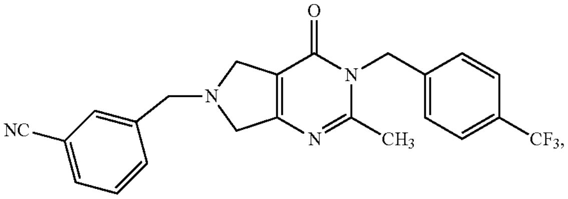,
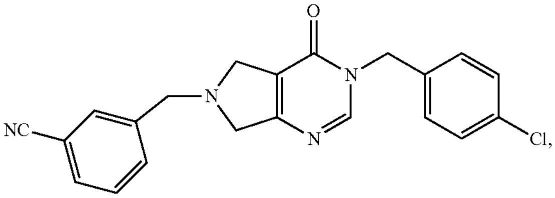,
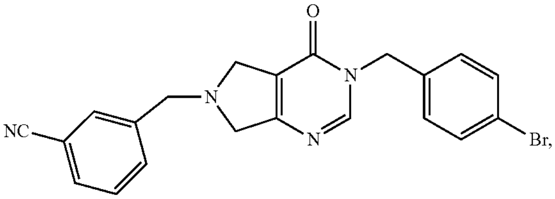,
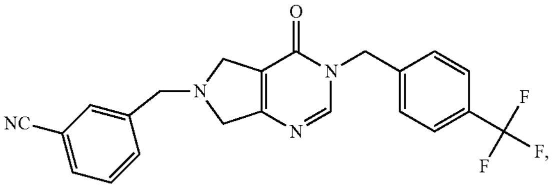,
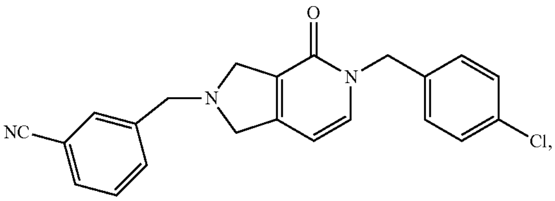, -continued
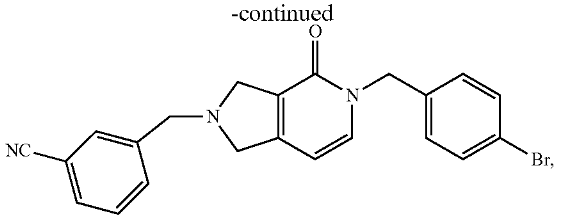
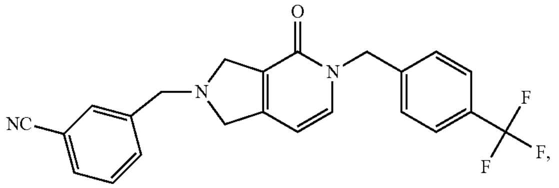
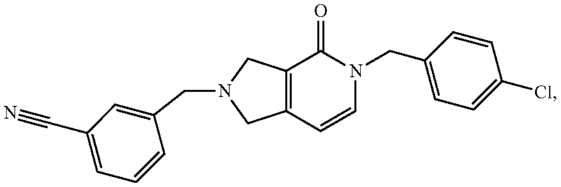
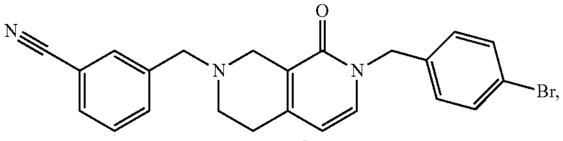
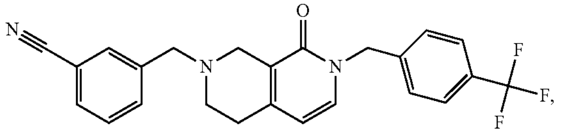
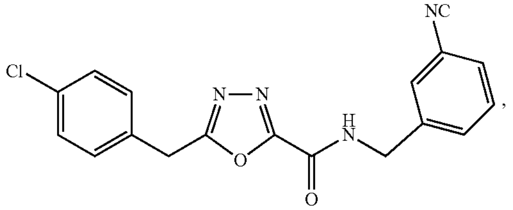
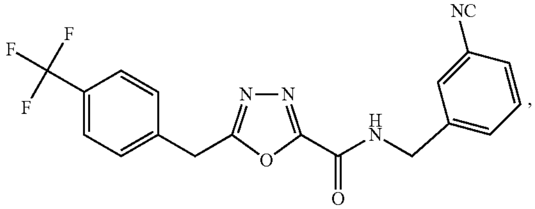
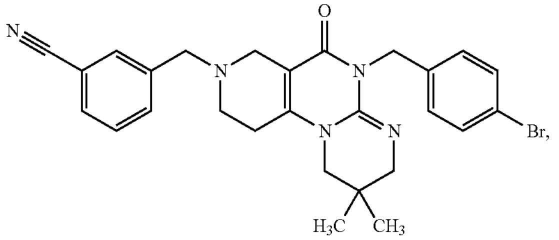
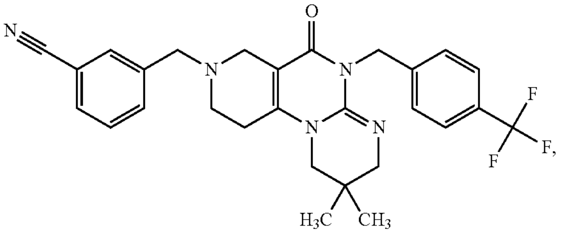
-continued
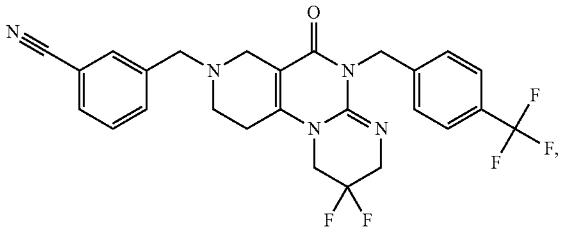
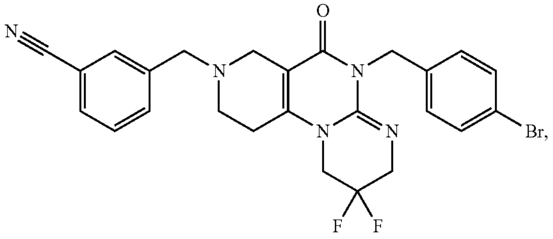
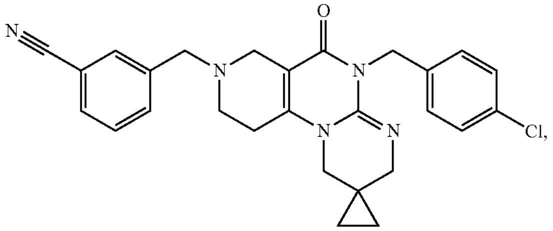
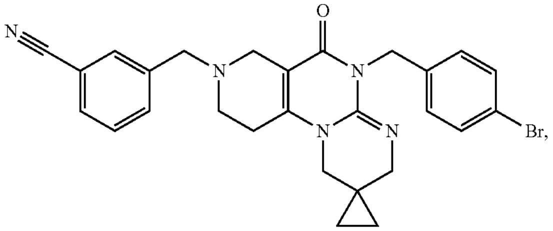
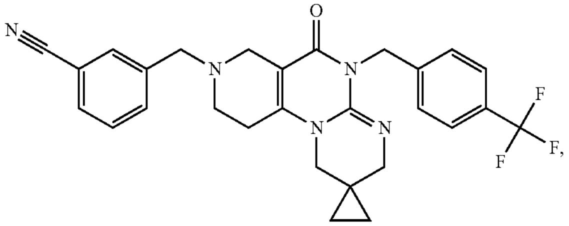
or a pharmaceutically acceptable salt thereof.
Another embodiment is a method of determining whether a mammal is responsive to the compound:
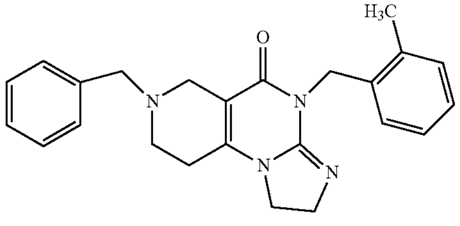
,
or a pharmaceutically acceptable salt thereof.
Another embodiment is a method of determining whether a mammal is responsive to the compound:

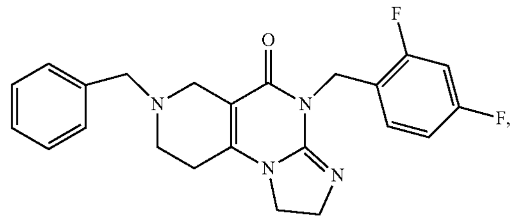 [SMILES: O=C1C2=C(CCN(Cc3ccccc3)C2)N2CCN=C2N1Cc1ccc(F)cc1F]

or a pharmaceutically acceptable salt thereof.

Another embodiment is a method for the treatment of a bacterial infection in a subject, comprising administering an effective amount of a compound of Formula I or a pharmaceutically acceptable salt thereof.

Another embodiment is a method for the treatment of a bacterial infection in a subject, comprising administering an effective amount of a compound of Formula I or a pharmaceutically acceptable salt thereof wherein:

Q is independently selected from Q2, Q3, Q4, Q5, Q6, Q7, Q8, Q9, Q10, Q11, Q12, Q13 and Q14.

Compounds of the Invention

Dosage Forms and Regimens

Administration of compounds of the invention may be affected by any method that enables delivery of the compounds to the site of action. These methods include oral routes, intraduodenal routes, parenteral injection (including intravenous, subcutaneous, intramuscular, or infusion), topical and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dose. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention may be dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose may be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention. It is to be noted that dosage values may vary with the type and severity of the condition to be alleviated, and may include single or multiple doses. It is to be further understood that for any particular subject, specific dosage regimens should be adjusted over time according to the individual need and the professional judgement of the person administering or supervising the administration of the compositions, and that dosage ranges set forth herein are exemplary only and are not intended to limit the scope or practice of the claimed composition. For example, doses may be adjusted based on pharmacokinetic or pharmacodynamics parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the active compound.

The pharmaceutically acceptable carrier may comprise any conventional pharmaceutical carrier or excipient. The choice of carrier and/or excipient, will to a large extent, depend on factors such as the particular mode of administration, the effect of the excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of material, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution, suspension or emulsion, for topical administration as an ointment or crease, or for rectal administration as a suppository.

Exemplary parenteral administration forms include solutions or suspensions of an active compound in a sterile aqueous solution, for example, aqueous propylene glycol or dextrose solutions. Such dosage forms may be suitably buffered, if desired.

The pharmaceutical composition may be in unit dosage forms suitable for single administration of precise amounts.

Pharmaceutical compositions suitable for the delivery of active agents and methods for their preparation will be readily apparent to those skilled in the art. Such compositions and methods for their preparation may be found, for example, in "Remington's Pharmaceutical Sciences", $19^{th}$ Edition (Mack Publishing Company, 1995), the disclosure of which is incorporated herein by reference in its entirety.

Compounds of the invention may be administered orally. Oral administration may involve swallowing, so that the compound enters the gastrointestinal tract, buccal or sublingual administration may be employed by which the compounds enters the blood stream directly from the mouth.

Formulations suitable for oral administration include solid formulations such as tablets, capsules containing particulates, liquids, or powders. Lozenges (including liquid filled), chews, multi- and nano-particulates, gels solid solution, liposome, films, ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, the active agent may make up from 1 wt % to 80 wt % of the dosage form, more typically from 5 wt % to 60 wt % of the dosage form. In addition to the active agent, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant may comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl, cellulose and hydroxypropyl methylcellulose. Tablets may also contain diluents, such as lactose, mannitol, xylitol, dextrose, sucrose, sorbitol, microcrystalline cellulose, starch, and dibasic calcium phosphate dehydrate.

Tablets may also optionally include surface active agents such as sodium lauryl sulfate and ploysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Exemplary tablets may contain up to about 80 wt % active agents for about 10 wt % to about 90 wt % binder, from about 0 wt % to about 85 wt % diluent, from about 2 wt % to about 10 wt % disintegrant, and from about 0.25 wt % to about 10 wt % lubricant.

The formulation of tablets is discussed in detail in "pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Suitable modified release formulations are described in U.S. Pat. No. 6,106,864. Details of other suitable release technologies such as high energy dispersions and osmotic and coated particles may be found in Verma et al, Pharmaceutical Technology On-line 25(2), 1-14 (2001). This disclosure of this reference is incorporated herein by reference in its entirety.

It is understood that compounds of Formula (I) can be formulated as a di-salt.

Parenteral Administration

Compounds of the invention may also be administered directly into the blood stream, into muscle, or into an internal organ. Suitable means for parenteral administration including intravenous, intraarterial, intraperitoneal, intrathecal, intraventricular, intraurethral, intracranial, intramuscular and subcutaneous. Suitable devices for parenteral administration include needle injectors, needle-free injectors and infusion techniques.

Parenteral formulations are typically aqueous solutions which may contain excipients such as salts, carbohydrates and buffering agents (preferably to a pH of 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may potentially be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may potentially be formulated as a solid, semi-solid, or thixotropic liquid for administration as an implanted depot providing modified release of the active compound. Examples of such formulations include drug-coated stents and PGLA microspheres.

The compounds of the invention may also potentially be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers bandages and microemulsions.

Dosage

The amount of the active compound administered will be dependent on the subject being treated, the severity of the disorder or condition, the rate of administration, the disposition of the compound and the discretion of the prescribing physician. However, the effective dose is typically in the range of about 0.001 to about 100 mg per kg body weight per day, preferably 0.01 to about 35 mg/kg/day, in a single or divided doses. For a human, this would amount to about 0.07 to about 700 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Combination Therapy

As used herein, the term "combination therapy" refers to the administration of a compound of the invention together with at least one additional pharmaceutical or medicinal agent (e.g., an anti-cancer agent), either sequentially or simultaneously.

As noted above, the compounds of the invention may potentially be used in combination with one or more additional anti-cancer agents, which are described below. When a combination therapy is used, the one or more additional anti-cancer agent may be administered sequentially or simultaneously with the compound of the invention. In one embodiment, the additional anti-cancer agent is administered to a mammal (subject, patient) prior to administration of the compound of the invention. In another embodiment, the additional anti-cancer agent is administered to the mammal after administration of the compound of the invention. In another embodiment, the additional anti-cancer agent is administered to the mammal simultaneously with the administration of the compound of the invention.

The invention also relates to a pharmaceutical composition for the treatment of abnormal cell growth in a mammal, including a human, which comprises an amount of a compound of the invention, as defined herein, in combination with one or more (preferably one to three) anti-cancer agents selected from a group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

In one embodiment of the present invention the anti-cancer agent used in conjunction with a compound of the invention and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKCbeta inhibitors, COX-2 inhibitors, integrins, MMP-2 (matrix-metalloproteinase 2) inhibitors, and MMP-9 (matrix-metalloproteinase 9) inhibitors.

Preferred anti-angiogenesis agents include sunitinib (Sutent®), bevacizumab (Avastin®), axitinib (AG 13736), SU 14813 (Pfizer), and AG 13958 (Pfizer).

Additional anti-angiogenesis agents include vatalanib (CGP 79787), Sorafenib (Nexavar®), pegaptanib octasodium (Macugen®), vandetanib (Zactima®), PF-0337210 (Pfizer), SU 14843 (Pfizer), AZD 2171 (AstraZeneca), ranibizumab (Lucentis®), Neovastat®) (AE 941), tetrathiomolyb-data (Coprexa®), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex®) and UCN 01 (Kyowa Hakko).

Other examples of anti-angiogenesis agents which may be used in conjuction with a compound of the invention and pharmaceutical compositions described herein include celecoxib (Celebrex®), parecoxib (Dynastat®), deracoxib (SC 59046), lumiracoxib (Preige™), valdecoxic (Bextra™), rofecoxib (Vioxx™), iguratimod (Careram®), IP 751 (Invedus), SC-58125 (Pharmacia) and etoricoxib (Arcoxia®).

Other anti-angiogenesis agents include exisulind (Aptosyn®), salsalate (Amigesic®), diflunisal (Dolobid®), ibuprofen (Motrin®), ketoprofen (Orudis®), nabumetone (Relafen®), piroxicam (Feldene®), naproxen (Aleve®, Naprosyn®), diclofenac (Voltarn®), indomethacin (Indocin®), sulindac (Clinoril®), tolmetin (Tolectin®), etodolac (Lodine®), ketorolac (Toradol®), and oxaprozin (Daypro®).

Other anti-angiogenesis agents include ABT 510 (abbott), apratastat (TMI 005), AZD 8955 (AstraZeneca), incyclinide (Metastat®), and PCK 3145 (*Procyon*).

Other anti-angiogenesis agents include acitretin (Neotigason®), plitidepsin (Aplidine®), cilengtide (EMD 121974), combretastatin A4 (CA4P), fenretinide (4 HPR), halofuginone (Tempostatin®), Panzem®, rebimastat (BMS 275291), catumaxomab, (Removab®), lenalidomide (Revlimid®), squalamine (EVIZON®), thalidomide (Thalomid®), Ukrain® (NSC 631570), Vitaxin® (MEDI 522), and zoledronic acid (Zomata®).

In another embodiment the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EgF inhibitors, ErbB-1 (EGFR) inhibitors, ErbB-2 inhibitors, pan-erb inhibitors, IGF1R inhibitors, MEK (1,2) inhibitors, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitors, P70S6 kinase inhibitors, CDK inhibitors, CDK4/6 inhibitors, BTK inhibitors of the WNT pathway and so called multi-targeted kinase inhibitors.

Preferred signal transduction inhibitors include gefitinib (Iressa®), cetuximab (Erbitux®), erlotinib (Tarceva®), trastuzmab (Herceptin®), sunitinib (Sutent®), imatinib (Gleevec®), Trametinib® (GSK1120212), abemaciclib (Verzenio®), palbociclib (Ibrance®), ribociclib ibrutinib (IMBRUVICA®), acalabrutinib (CALQUENCE®, LOXO-305, and Cobimetinib® (XL518).

Additional examples of signal transduction inhibitors which may be used in conjunction with a compound of the invention and pharmaceutical compositions described herein include BMS 214662, lonafarnib (Sarasar®), pelitrexol (AG 2037), matuzumab (EMD 7200), nimotuzumab (TheraCIM h-R3®), panitumumab (Vectibix®), vandetanib (Zactima®), pazopanib (SB 786034), BIBW 2992 (Boehringer Ingelheim), and Cervene® (TP 38).

Other examples of signal transduction inhibitors include Canertinib (CI 1033), pertuzumab (Omnitarg®), Lapatinib (Tycerb®), pelitinib (EKB 569), miltefosine (Miltefosin®), BMS 599626, Lapuleucel-T (Neuvenge®), NeuVax®), Osidem® (IDM 1), mubritinib (TAK-165), Panitumumab (Vectibix®), lapatinib (Tycerb®), pelitinib (EKB 569), erbafitinib (Balversa), and pertuzumab (Omnitarg®).

Other examples of signal transduction inhibitors include ARRY 142886, everolimus (Certican®), zotarolimus (Endeavor®), temsirolimus (Torisel®), and VX 680 (Vertex).

This invention contemplates the use of a compound of the invention together with antineoplastic agents. Antineoplastic agents include, but are not limited to, hormonal, anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose), polymerase-1 (PARP-1) inhibitors, microtubulin inhibitors, antibiotics, spindle inhibitors, platinum-coordinated compounds, gene therapeutic agents, antisense oligonucleotides, vascular targeting agents (VTAs) and statins.

Examples of antineoplastic agents used in combination therapy with a compound of the invention, include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486) selective estrogen receptor modulators (SERMs, such as tamoxifen, raloxifene, lasofoxifene, afimoxifene, arzoxifene, bazedoxifene, fispemifene, ormeloxifene, ospemifene, tesmilifene, toremifene, trilostance and CHF 4227 (Cheisi), selective estrogen-receptor downregulators (SERDs, such as fulvestrant), exemestane (Aromasin®), anastrozole (Arimidex®), atamestane, fadrozole, letrozole (Femara), gonadotropin-releasing hormone (GnRH, also commonly referred to as luteinizing hormone-releasing hormone [LHRH]) agonists such as buserelin (Suprefact), goserelin (Zoladex), leuprorelin (Lupron), and triptorelin (Trelstar®), abarelix (Plenaxis®), bicalutamide (Casodex®), cyproterone, flutamide (Eulexin®), megestrol, nilutamide (Nilandron), and osaterone, dutasteride, epristeride, finasteride, abarelix, goserelin, leuprorelin, triptorelin, bicalutamide, tamoxifen, exemestane, anastrozole, fadrozole, fromestane, letrozole, and combinations thereof.

Other examples of antineoplastic agents used in combination with a compound of the invention include, but are not limited to, suberolanilide hydroxamic acid (SAHA®, Merck), depsipeptide (FR901228), G2M-777, MS-275, pivaloyloxymethyl butyrate and PXD-101/Onconase® (ranpimase), PS-341, Valcade® (bortezomib), 9-aminocamptothecin, belotecan, BN-80915, camptothecin, diflomotecan, edotecarin, exatecan, gimatecan, 10-hydroxycamptothecin, irinotecan HCl (Camptosar®), lurtotecan, Orathecin® (rubitecan, Supergen®), SN-38, topotecan, camptothecin, 10-hydroxycamptothecin, 9-aminocamptothecin, irinotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard® (dexrazoxane), nitrogen mustard N-oxide, cyclophosphamide, AMD-473, altretamine, Ap-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating agents such as cisplatin. Paraplatin (carboplatin), eptaplatin, lobaplatin, nedaplatin, Eloxatin® (oxaliplatin), streptozocin, satrplatin, and combinations thereof.

The invention also contemplates the use of a compound of the invention together with dihydrofolate reductase inhibitors (for example methotrexate and NeuTrexin® (trimetresate glucoronate)), purine antagonist (for example 6-mercaptopurine riboside, mercaptopurine, 6-thioguanine, cladribine, clofarabine (Clolar®), fludarabine, nelarabine, and raltitrexed), pyrimidine antagonists (for example, 5-fluorouracil (5-FU), Alimta® (premetrexed disodium), capecitabine (Xeloda®), cytosine, Arabinoside, Gemzar® (gemcitabine), Tegafur® (UFT Orzel® or UForal® and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza®), decitabine, and ethynyl-cytidine) and other antimetabolites such as eflomithine, hydroxyurea, leucovorin, nolatrexed, triapine, trimetrexate, ABT-472, Ino-1001, KU-0687 and GPI 18180 and combinations thereof.

Additional examples of antineoplastic agents used in combination therapy with a compound of the invention, optionally with one or more other agents include, but are not limited to, Advexin®, Genasense (oblimersen, Genta®), Combretastatin A4P (CA4P), Oxi4503, AVE-8062, ZD-6126, TZT 1027, atorvastatin (Lipitor®), pravastatin (Pravachol®) lovastatin (Mevacor®), simvastatin (Zocor®), fluvastatin (Lescol®), cerivastatin (Baycol®), rosuvastatin (Crestor®), niacin (Advicor®), caduet and combinations thereof.

The invention also contemplates the use of a compound of the invention together with agents that modulate the immune system include, but are not limited to, pembrolizumab (Keytruda®), nivolumab (Opdivo®), cemiplimab (Liptayo®), atezolizumab (Tecentrig®), avelumab (Bavencio®), durvalumab (Imfinzi®), ipilimumab (Yervoy®), rituximab (RITUXAN®, Thor-707, and dexamethazone.

The invention also contemplates the use of a compound of the invention together with agents that modulate the BCL-2 family of proteins include, but are not limited to, venetoclax, (Venelexta®, ABT-199) and AMG176.

The invention also contemplates the use of a compound of the invention together with agents that inhibit the androgen receptor include, but are not limited to, apalutamide (Erleada®), flutamide (Eulexin®), nilutamide (Nilandron®), dicalutamide (Casodex®) and enzalutamide (Xtandi®).

The invention also contemplates the use of a compound of the invention together with agents that modulate the PARP family of proteins include, but are not limited to, niraparib (Zejula®), olaparib (Lynparza®), rucaparib (Rubraca®) and talazoparib (Talzenna®).

Another embodiment of the present invention of particular interest relates to a method for the treatment of breast cancer in a human in need of such treatment, comprising administering to said human an amount of a compound of the invention, in combination with one or more (preferably one to three) anti-cancer agents selected from the group consisting of trastuzumab, tamoxifen, docetaxel, paclitaxel, capecitabine, gemcitabine, vinorelbine, exmestane, letrozole and anastrozole.

Another embodiment of the present invention relates to the method of treatment of neurodegenerative diseases in a human in need of such treatment, comprising administering to said human an amount of a compound of the present invention in combination with one or more agents selected from the group consisting of anti-tau mAb, anti-beta-amyloid mAb, BIIB067 (tofersen), BAN2401, BIIB054 (anti-alpha-synuclein), BIIB074, BIIB092, BIIB092 (gosuranemab), BIIB104, Natalizumab, BIIB076 (anti-tau mAb), BIIB078 (IONIS-C9RX), BIIB080 (IONIS-MAPTRX), BIIB095 (NAV 1.7), BIIB (XPO1 inhibitor), BIB110, cholinesterase inhibitors (Aricept®, Exelon®, Razadyne®), memantine (Namenda®), Levodopa, Lodosyn, dopamine agonists (pramipexole, ropinirole, rotigotine and apomorphine), MAO B Inhibitors (selegiline, rasagiline, safinamide), catechol O-methyltransferase (COMT) inhibitors (entacapone and tolcapone), anticholinergics (benztropine and trihexphenidyl), amantadine, riluzole, edavarone, xenazine, antipsychotics and benzodiazepines.

Therapeutic Methods and Uses

The invention further provides therapeutic methods and uses comprising administering a compound of the invention, or pharmaceutically acceptable salt thereof, alone or in combination with one or more other therapeutic agents or palliative agents. The compositions and methods described herein have utility in treating many disease conditions, including cancer.

Cancers treated using methods, compositions and/or agents described herein are characterized by abnormal cell proliferation including, but not limited to, pre-neoplastic hyper-proliferation, cancer in-situ, neoplasms and metastasis. Method and compositions described herein can be used for prophylaxis, and amelioration of signs and/or symptoms of cancer.

In one aspect, the compositions and methods described herein are used to treat diseases such as ocular melanoma, desmoplastic round cell tumor, chondrosarcoma, leptomengial disease, diffuse large B-cell lymphoma, Acute Lymphoblastic Leukemia, Acute Myeloid Leukemia, Adrenocortical Carcinoma, Aids-Related Cancers, Aids-Related Lymphoma, anal or rectal cancer, appendix cancer, Astrocytomas, and atypical Teratoid/Rhabdoid tumor.

In one aspect, the compositions and methods described herein are used to treat diseases such as basal cell carcinoma, basel cell nevus syndrome, Gorlin-Nevus Syndrome, Bile Duct Cancer, bladder cancer, bone cancer, osteosarcoma, and malignant fibrous histiocytoma, brain tumor, breast cancer, bronchial tumors, Burkitt lymphoma, and spinal cord tumors.

In one aspect, the compositions and methods described herein are used to treat diseases such as carcinoid tumor, carcinoma of unknown primary, central nervous system atypical Teratoid/Rhabdoid tumor, leptomeningeal disease, central nervous system embryonal tumors, central nervous system lymphoma, cervical cancer, chordoma, Chronic Lymphocytic Leukemia, Chronic Myelogenous Leukemia, Chronic Myeloproliferative disorders, Colon cancer, colorectal cancer, craniopharyngioma, cutaneous T-cell lymphoma, embryonal tumors of the central nervous system, endometrial cancer, ependymoblastoma, ependymoma, esophageal cancer, Ewing Sarcoma, extracranial germ cell tumor, extragonadal germ cell tumor, extrahepatic bile duct cancer, eye cancer, gallbladder cancer, gastric cancer, gastrointestinal cancer, gastrointestinal stromal tumor, germ cell tumor, gestational trophoblastic tumor, glioma, hairy cell leukemia, head and neck cancer, hepatocellular cancer, histiocytosis, Hodgkin lymphoma, hypopharyngeal cancer, Kaposi sarcoma, kidney cancer, Langerhans Cell Histiocytosis, laryngeal cancer, lip and oral cavity cancer, liver cancer, lung cancer, Non-Hodgkin Lymphoma, Waldenstrom's macroglobulinemia, malignant fibrous histiocytoma of bone and osteosarcoma, medulloblastoma, medulloepithelioma, melanoma, Merkel cell carcinoma, mesothelioma, metastatic squamous neck cancer with occult primary, multiple neoplasia syndrome, mouth cancer, multiple/plasma cell neoplasm, mycosis fungoides, myelodysplastic syndromes, neoplasms, multiple myeloma and myeloproliferative disorders.

In one aspect, the compositions and methods described herein are used to treat cancer.

The invention further provides therapeutic methods and uses comprising administering a compound of the invention, or pharmaceutically acceptable salt thereof, alone or in combination with one or more therapeutic agents or palliative agents.

In one aspect, the invention provides a method for the treatment of disease states where an abnormally high concentration of a protein that is a substrate for ClpP exists in a subject comprising administering to the subject a therapeutically effective amount of a compound of the invention, or a pharmaceutically acceptable salt thereof.

In one aspect, the invention provides a method for the treatment of disease states, including cancer where the reduction in the concentration of a protein that is a substrate for ClpP in a subject leads to an amelioration of disease comprising administering to the subject a therapeutically effective amount of a compound of the invention, or a pharmaceutically acceptable salt thereof.

In one aspect, the invention provides a method for the treatment of disease states, including cancer where an abnormally high concentration of the protein, ClpP exists in a subject comprising administering to the subject a therapeutically effective amount of a compound of the invention, or a pharmaceutically acceptable salt thereof.

In one aspect, the invention provides a method for the treatment of disease states where an abnormally low concentration of the protein, ClpP exists in a subject comprising administering to the subject a therapeutically effective amount of a compound of the invention, or a pharmaceutically acceptable salt thereof.

In one aspect, the invention provides a method for the treatment of abnormal cell growth in a subject comprising administering to the subject a therapeutically effective amount of a compound of the invention, or a pharmaceutically acceptable salt thereof.

In another aspect, the invention provides a method for the treatment of abnormal cell growth in a subject comprising administering to the subject an amount of a compound of the invention, or a pharmaceutically acceptable salt thereof, in combination with an amount of an anti-tumor agent, which amounts are together effective in treating said abnormal growth. In some embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones and anti-androgens.

In another aspect, the invention provides a method of inhibiting cancer cell proliferation in a subject, comprising administering to the subject a compound of the invention, or pharmaceutically acceptable salt thereof, in an amount effective to inhibit cell proliferation.

In another aspect, the invention provides a method for treatment for a cancer selected from the group consisting of solid tumors, liquid tumors, lymphomas, leukemias or myelomas. In some embodiments, treatment of cancer comprises prevention of tumor growth in a cancer subject, comprising administering to the subject a compound of the invention, or pharmaceutically acceptable salt thereof, in an amount effective to inhibit cell proliferation.

In another aspect, the invention provides a method of inhibiting cancer cell invasiveness in a subject, comprising administering to the subject a compound of the invention, or pharmaceutically acceptable salt thereof, in an amount effective to inhibit cell proliferation.

In another aspect, the invention provides a method of inducing apoptosis in cancer cells in a subject, comprising administering to the subject a compound of the invention, or pharmaceutically acceptable salt thereof, in an amount effective to inhibit cell proliferation.

In another aspect, the invention provides a method of inducing apoptosis in a subject, comprising administering to the subject a compound of the invention, or pharmaceutic acceptable salt thereof, in an amount effective to inhibit cell proliferation.

In frequent embodiments of the methods provided herein, the abnormal cell growth is cancer, wherein said cancer is selected from the group consisting of basal cell cancer, medulloblastoma cancer, liver cancer, rhabdomyosarcoma, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In some embodiments, the cells are in a tissue or tumor, and the tissue or tumor may be in a subject, including a human.

Cancers treated using methods and compositions described herein are characterized by abnormal cell proliferation including, but not limited to, metastasis, pre-neoplastic hyperproliferation, cancer in situ, and neoplasms. Compounds of this invention can be for prophylaxis in addition to amelioration of signs and/or symptoms of cancer. Examples of cancers treated by the compounds of the present invention include, but are not limited to, breast cancer, CNS cancers, colon cancer, prostate cancer, leukemia, lung cancer and lymphoma.

In another aspect, the invention provides a method for the treatment of a leukemia selected from the group consisting of: Acute Lymphoblastic Leukemia (ALL), Chronic Lymphocytic Leukemia (CLL), Chronic Myeloproliferative Disorders, Hair Cell Leukemia, Acute Myeloid Leukemia (AML), Chronic Myelogenous Leukemia (CML) and Langerhans Cell Histiocytosis.

In another aspect, the invention provides a method for the treatment of a lymphoma selected from the group consisting of: diffuse large B-cell lymphoma, AIDS-Related Lymphoma, Cutaneous T-Cell Lymphoma, Sezary syndrome, mycosis fungoides (MF), Histiocytosis, Burkitt Lymphoma, Central Nervous System Lymphoma, Non-Hodgkin Lymphoma, Primary Central System Nervous System Lymphoma, Hodgkin Lymphoma, Waldenstrom's macroglobulinemia, mycosis fungoides and lymphoplasmacytic lymphoma.

In another aspect, the invention provides a method for the treatment of a cancer in a subject comprising administering to the subject a therapeutically effective amount of a compound of the invention, or a pharmaceutically acceptable salt thereof.

In another aspect, the invention provides a method for the treatment of a cancer selected from the group consisting of: vaginal cancer, vulvar cancer, endometrial cancer, carcinoma of unknown primary site and cancer of unknown primary site.

In another aspect, the invention provides a method for the treatment of a bacterial infection in a subject comprising administering to the subject a therapeutically effective amount of a compound of the invention, or a pharmaceutically acceptable salt thereof.

In another aspect, the invention provides a method for the treatment of a *Staphylococcus aureus* infection in a subject comprising administering to the subject a therapeutically effective amount of a compound of the invention, or a pharmaceutically acceptable salt thereof.

In another aspect, the invention provides a method for the treatment of a neurodegenerative disease including by not limited to, Alzheimer's disease, Parkinson's disease, Huntington's disease, amyotrophic lateral sclerosis, spinocerebellar ataxia, spinal muscular atrophy and motor neurone diseases in a subject comprising administering to the subject a therapeutically effective amount of a compound of the invention, or a pharmaceutically acceptable salt thereof.

In another aspect, the invention provides a method for the treatment of erythropoietic protoporphyrin (EPP) in a subject comprising administering to the subject a therapeutically effective amount of a compound of the invention, or a pharmaceutically acceptable salt thereof.

In another aspect, the invention provides a method for the treatment of erythropoietic protoporphyrin (EPP) in a subject with the dominant mutant (ClpX: p.Gly298Asp) comprising administering to the subject a therapeutically effective amount of a compound of the invention, or a pharmaceutically acceptable salt thereof.

In another aspect, other conditions that may be suitable for the methods described herein include, but are not limited to, Attention Deficit Disorder; addiction; Epilepsy; viral infection; inflammation; neurodegenerative diseases such as Alzheimer's disease, Parkinson's disease, Huntington's disease, Amyotrophic lateral sclerosis; cardiovascular diseases such as coronary artery disease, cardiomyopathy, hypertensive heart disease, heart failure, pulmonary heart disease, cardiac dysrhythmias, inflammatory heart disease, endocarditis, inflammatory cardiomegaly, myocarditis, valvular heart disease, cerebrovascular disease, peripheral arterial disease, congenital heart disease, rheumatic heart disease; diabetes and light chain amyloidosis.

In another aspect, the invention provides a method for the treatment of cystic fibrosis.

In another aspect, the invention provides a method for the treatment of Perrault syndrome.

In another aspect, the invention provides a method for the treatment of Perrault syndrome type 3.

In another aspect, the invention provides a method for the treatment of autoimmune disease. Autoimmune diseases include, but are not limited to alopecia areata, antiphospholipid, autoimmune hepatitis, celiac disease, diabetes type 1, Graves' disease, Guillain-Barre syndrome, Hasimoto's disease, hemolytic anemia, idiopathic thrombocytopenic purpura, inflammatory bowl disease, inflammatory myopathies, multiple sclerosis, primary biliary cirrhosis, psoriasis, rheumatoid arthritis, scleroderma, Sjogren's syndrome, systemic lupus erythematosus, psoriatic arthritis, Crohn's disease and vitiligo.

In another aspect, the invention provides a method for the treatment of allograft rejection. In another aspect, the invention provides a method for the treatment of hereditary spastic paraplegia.

In another aspect, the invention provides a method for the treatment of the condition, acquired immunodeficiency syndrome (AIDS).

In another aspect, the invention provides a method for the treatment of HIV and the condition, acquired immunodeficiency syndrome (AIDS).

In another aspect, the invention provides a method for the treatment of the condition, pneumonia.

In another aspect, the invention provides a method for the treatment of the condition, sepsis.

In another aspect, the invention provides a method for the treatment of the condition, viral infection.

In another aspect, the invention provides a method for the treatment of hepatitis in a subject, comprising administering to the subject a therapeutically effective amount of a compound of the invention, or a pharmaceutically acceptable salt thereof.

In another aspect, the invention provides a method for the treatment of cryptogenic cirrhosis in a subject, comprising administering to the subject a therapeutically effective amount of a compound of the invention, or a pharmaceutically acceptable salt thereof.

In another aspect, the invention provides a method for the treatment of hepatocyte senescence in a subject, comprising administering to the subject a therapeutically effective amount of a compound of the invention, or a pharmaceutically acceptable salt thereof.

In another aspect, the invention provides a method for the treatment of nonalcoholic fatty liver disease (NAFLD) in a subject, comprising administering to the subject a therapeutically effective amount of a compound of the invention, or a pharmaceutically acceptable salt thereof.

In another aspect, the invention provides a method for the treatment of nonalcoholic steatohepatitis (NASH) in a subject, comprising administering to the subject a therapeutically effective amount of a compound of the invention, or a pharmaceutically acceptable salt thereof.

Methods of Preparation, Chemical Compounds

The compounds of this invention may be made by a variety of methods, including standard chemistry. Any previously defined variable will continue to have previously defined meaning unless otherwise noted. Illustrative general synthetic methods are set out below, specific compounds of Formula (I) are prepared in the Examples, and additional information on the synthesis of these compounds are described in the following citations: Sun H. et al ACS Med. Chem. Lett. 2019, 10, 191-195 and references cited therein, WO 2018 031990 and references cited therein, WO 2018 031987 and references cited therein, CN 1048600948 and references cited therein, and U.S. Pat. No. 8,318,751 and references cited therein.

There are currently many suppliers of chemical reagents. Examples of chemical suppliers: Sigma Aldrich, Saint Louis, MO; Alfa Aesar, Tewksbury, MA; TCI America. Portland, OR; BroadPharm, San Diego, CA and Cambridge BioSciences, Cambridge, UK, in no way is this list meant to be limiting. BroadPharm also provides custom services providing reagents for the synthesis of compounds of this invention. ONC201 (CAS 1616632-77-9) is commercially available from a number of suppliers including: MEDCHEM Express, 1 Deer Park Drive, Suite Q, Monmouth Junction, NJ, 08852. 2-(3-iodopropyl) isoindoline-1,3-dione is available from multiple vendors including Sigma-Aldrich (Aldrich CPR-R465674). In addition, 2-(4-iodobutyl) isoindoline-1,3-dione is also available from multiple vendors including Sigma-Aldrich (Aldrich CPR-R260312). Both ONC201 and ONC206 are available from commercial suppliers including SelleckChem, Houston, TX 77014, MedKoo BioSciences, Inc and Matrix Scientific, Columbia, SC 29224.

Compounds of general Formula (I) may be prepared by methods known in the art of organic synthesis as set forth in part by the following synthetic schemes. In all the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers. When a compound is desired as a single isomer it may be obtained by various methods of separation of the final product or key intermediate or alternatively may be made by a stereo specific synthesis using isomerically pure intermediates or methods to impart isomeric purity. These are known to those skilled in the art.

Compounds were analyzed by common methods known to those skilled in the art. NMR and HPLC and LCMS were used to evaluate isolated compounds and to evaluate reaction mixtures. LCMS conditions used water and MeCN as the two solvents using a Symmetry C18, 5 um, 4.6×50 mm column. A linear gradient was used from time 0 (90% $H_2O$, 10% MeCN, 0.1% TFA) to time 4.5 min (5% $H_2O$, 95% MeCN, 0.1% TFA). The flow rate was 1.7 ml/min. Evaluation was at 254 nm.

The following solvents, reagents, protecting groups, moieties, and other designations may be referred to by their abbreviations:

Me: methyl;
Et: ethyl;
Pr: propyl;
i-Pr: isopropyl;
Bu: butyl;
t-Bu: tert-butyl;
Ac: acetyl
ACN: acetonitrile
AcOH: acetic acid
Aq.: aqueous
AUC: area under a curve
BOC or Boc: tert-butyloxycarbonyl
Conc.: concentrated
DMF: dimethylformamide
DMSO: dimethylsulfoxide
EDCI or EDC: 1-Ethyl-3-(3-dimethylaminopropyl)carbodiimide
EtOAc: ethyl acetate
EtOH: ethyl alcohol
Ex.: Example
g: grams
h: hours
HPLC: high-performance liquid chromatography
LCMS: liquid chromatography mass spectrometry
MeOH: methyl alcohol
MeI: methyl iodide
MS: mass spectrometry
NA: not applicable ND: no data reported
NMR: nuclear magnetic resonance spectrometry
NT: not tested
Ph: phenyl,
Ret Time: retention time
RT or rt: room temperature
Satd, Sat'd, sat'd and satd.: saturated
TFA: trifluoroacetic acid
THF: tetrahydrofuran Of particulate note is the use of toluene analogs as reagents and synthetic intermediates. There are numerous commercial sources of toluene analogs which may be used directly or converted to useful reagents or intermediates used for the synthesis of compounds of this invention. Numerous methods are known to those skilled in the art for the interconversion of toluene analogs to provide reagents and intermediates useful for the synthesis of the compounds of this invention. Examples described herein include the bromination of the methyl residue (Ex. 64) and the conversion of a functionalized benzyl alcohol to the corresponding bromide (Ex. 79). In addition, benzyl alcohols may be converted to the corresponding benzyl amines via oxidation to the aldehyde followed by a reductive amination process. These examples are not to be limiting.

Aromatic residues with a single J substituent are meant to denote various J residues (one or more) as describe herein and at various positions on the aromatic residue to which it is shown to be attached.

Compounds described when Q is Q3 may be prepared as shown in Scheme 1. In addition, the scheme used to prepare Ex. 61 may be used to prepare compounds of this invention. Those skilled in the art may extrapolate this method of preparation with the information contained in the references cited herein and common synthetic chemical knowledge to fashion the agents. Of particular note is the information on the synthesis of chemically related matter in U.S. Pat. No. 8,318,751 and references cited therein.

In addition, further synthetic details for the preparation of compounds when Q is Q3 are found in WO 2008/130584 and references contained therein. Similarly compounds of the present invention where Q is Q10 may be prepared similarly to compounds where Q is Q3. The chemistry describe for the synthesis of compounds where Q is Q3 uses various functionalized piperidine compounds as synthetic intermediates in a similar fashion compounds where Q is Q10 may use the same or similar synthetic routes using various functionalized pyrrolidine compounds as synthetic intermediates.

Scheme 1

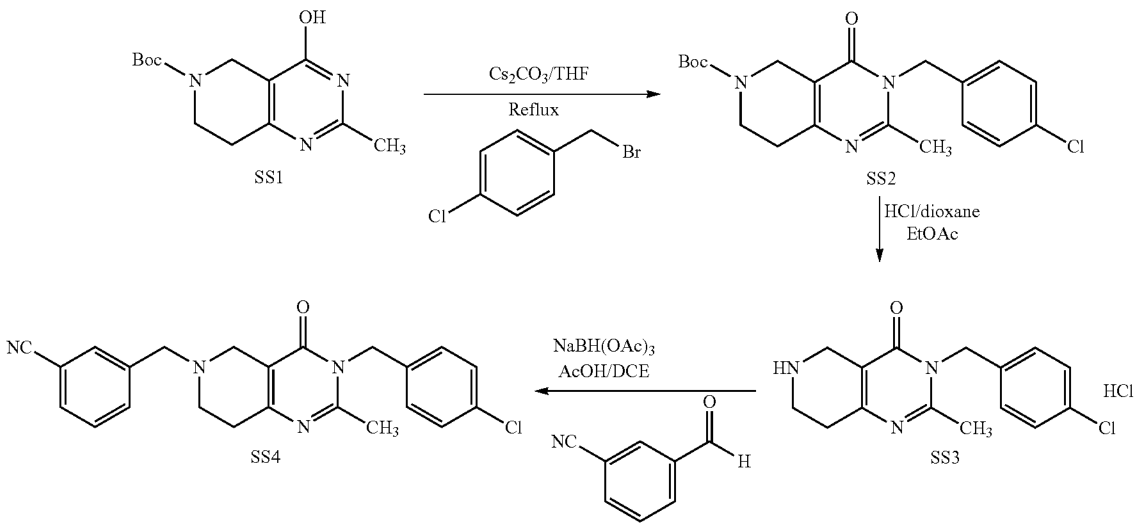

Compounds described when Q is Q4 may be prepared as shown in Scheme 2. Those skilled in the art may extrapolate this method of preparation with the information contained in the references cited herein (Stahl M., et al, Angew. Chem. Int. Ed. 2018, 57, 14,602-14,607 and references cited therein) and common synthetic chemical knowledge to fashion the agents.

Scheme 2

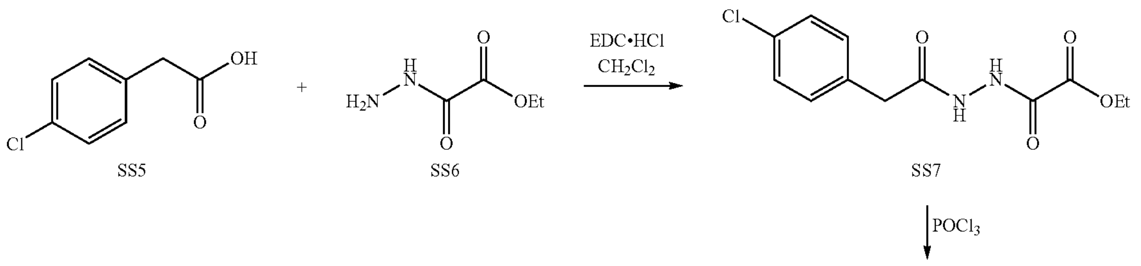

-continued

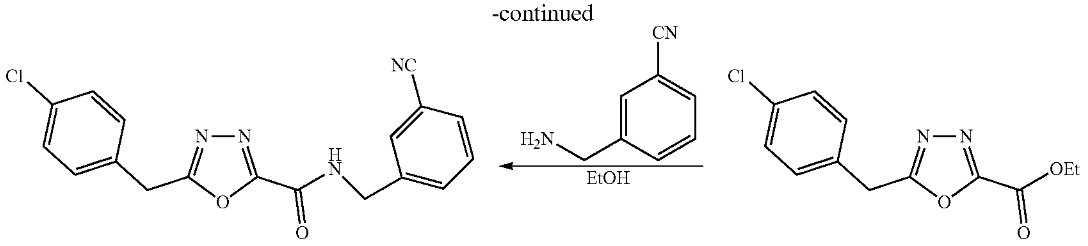

SS9 SS8

Compounds described when Q is Q2 may be prepared as described in WO 2018 031990 and references cited therein. In addition, synthetic methods and schemes described by Ma, Z (Ma, Z. et al, ACS Med. Chem. Lett. 2019, 10, 191-195 and references cited therein) and Furrer (U.S. Pat. No. 5,556,854 and references cited therein) are applicable to making agents of the present invention. Those skilled in the art may extrapolate this method of preparation with the information contained in the references cited herein and common synthetic chemical knowledge to fashion the agents.

Compounds described when Q is Q1 may be prepared as described in WO 2018 031987 and references cited therein. There are other many publications that describe the synthesis of these agents such as: El-Deiry, W. S. et al, Cell Cycle 2017, 16, 1790-1799 and references cited therein. Those skilled in the art may extrapolate this method of preparation with the information contained in the references cited herein and common synthetic chemical knowledge to fashion the agents.

Compounds described by when Q is Q2 and may be coupled with various infrared, fluorescent, phosphorescent, radioactive or infrared fluorescent as shown in Scheme 3. Compounds shown as SS10 are valuable intermediates for the fashioning compounds of this invention to other diagnostic agents. The length of the carbon linker determined by n can be 1-30 however n=1-5 is more optimal. These analogs are made as described above using an appropriate protecting group for the terminal functionality. The amine terminus of the alkyl chain has particular value as a reactive species and can easily fashion many common functional groups such as: amides, carbamates, secondary amines, etc., using acid chlorides, ketenes, carboxylic acids (with coupling agents) and alike. Other terminal residues in addition to the amine may be used to fashion linkers, such as —SH, —OH, —Cl, —Br and —I. These terminal residues may be linked to various dyes and imaging agents. Commercially available (BroadPharm, Inc, 6625 Top Gun Street, Suite 103, San Diego, CA 92121) fluorescent dyes containing a large variety of functional groups for easy of coupling and different length of PEG spacer for increased water solubility. Enable efficient biolabeling in imaging and diagnostic R&D. Classes of agents sold by BroadPharm, Inc include: BDP, Cyanine 3, Cyanine 5, Cyanine 5.5, Cyanine 7, fluorescein and pyrene. This example is not meant to be limiting.

Additional experimental information of the synthesis of coupled dyes can be found in the following references: Wang L. et al, Angew Chem Int Ed. 2019 Mar. 7. Doi: 10.1002/anie.201901061 and references cited therein, Gomes da Costa, S. et al, Morphologie 2019, March; 103 (341):11-16 and references cited therein, Wei H. et al, Future Med Chem 2018, Dec. 6. doi: 10.4155/fmc-2018-0198 and references cited therein, Alamudi, S. H. et al, Chem Commun 2018 Dec. 4; 54(97): 13641-13653 and references cited therein, Iliopoulos-Tsoutsouvas C. et al, Expert Opin Drug Discov 2018 October; 13(10):933-947 and references cited therein, VernalI A. J. et al, Br J Pharmacol 2014 March; 171(5):1073-84 and references cited therein, and Broyles C. N. et al, Cells 2018 May 31; 7(6) and references cited therein.

Scheme 3

SS10

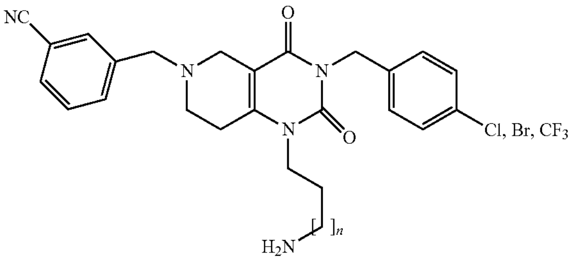

A general synthetic scheme shown as Scheme 4, is a series of reactions that one skilled in the art may use to prepare compounds of the invention. Substituents X and Y denote various substituents that may be used for this reaction sequence and their positions on their respective aromatic residues are not limited. In addition, more than one substituent may be present on a single aromatic residue. Central to this chemical synthetic route is the use of isocyanates here shown as SS15. In the case where J is a single chlorine atom and the remaining positions that may be substituted are hydrogen, the isocyanate required has the chemical formula of: $C_8H_6ClNO$. In addition, the last step (d) is envisioned to allow for the attachment of various residues here identified by R. Alternative methods for N-alkylation are known to those skilled in the arts. For example, SS13 may be prepared from SS11 using the corresponding benzaldehyde and a reducing agent. This example is not to be limiting with regard to the number and type of substituents that may be used therein. Alternative reaction conditions, known to those skilled in the art, may be employed for the various transformations in Scheme 4.

Scheme 4

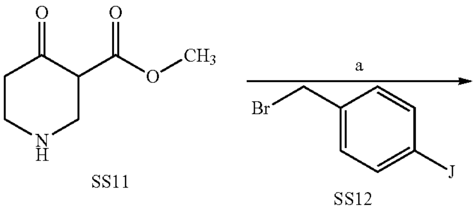

SS11 SS12

-continued

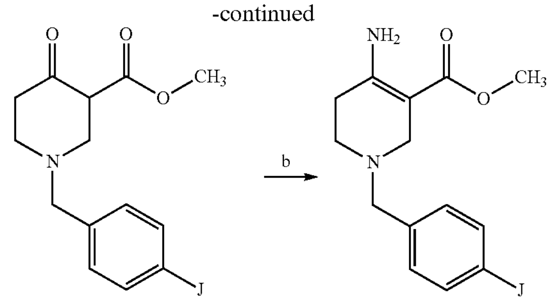

SS13 SS14

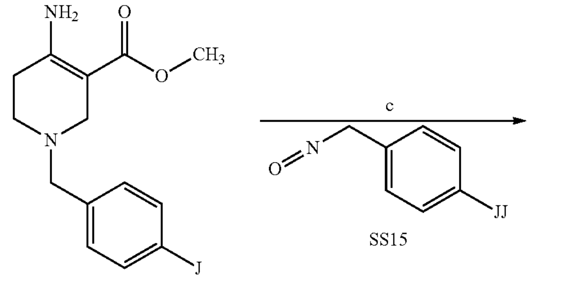

SS15

SS14

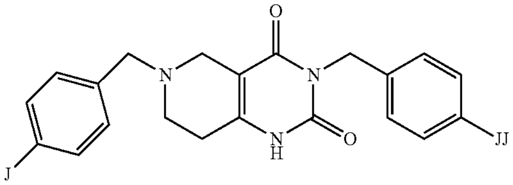

SS16

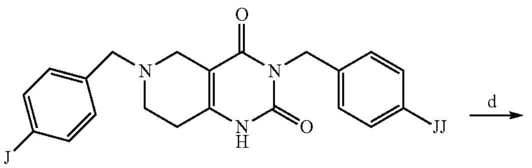

SS16

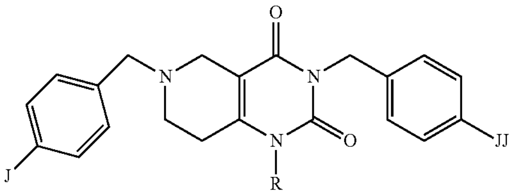

SS17

Synthesis of compounds of Scheme 4: (a) DMF, $Et_3N$; (b) sodium carbonate, $NH_3$, ethanol, 70° C. 5 h; (c) $Et_3N$, toluene, reflux, 80° C. 8 h; (d) RBr, $K_2CO_3$, DMF, 100° C., 12 h.

A general synthetic scheme shown as Scheme 5A, is a series of reactions that one skilled in the art may use to prepare compounds of the invention. Substituents J are independently selected Y and their positions on aromatic system are not limited. Central to this chemical synthetic route is the use of a two-step synthetic sequence to form a ring. A carbon nitrogen bond is formed on SS16 to give SS19. Of critical importance is the reagent SS18 which has a protected nucleophile (nitrogen) that once unprotected yielding SS21 is now poised to condense upon itself to form the ring in SS23. SS23 are examples when Q is Q5. These examples are not to be limiting with regard to the number and type of substituents that may be used therein. Alternative reaction conditions, known to those skilled in the art, may be employed for the various transformations in Scheme 5A.

Scheme 5A

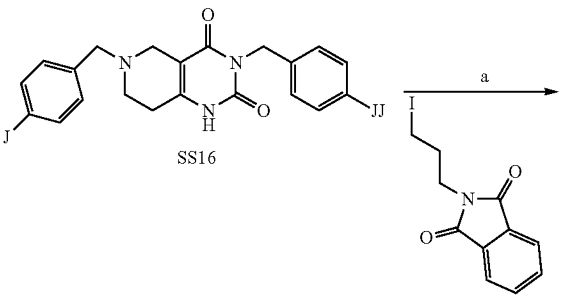

SS16

SS18

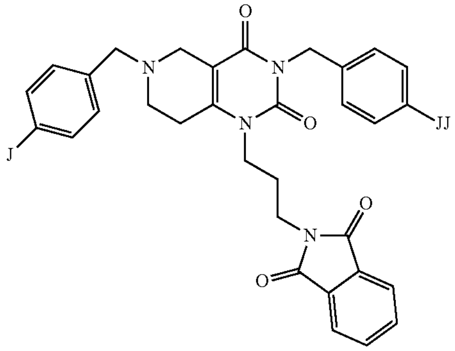

SS19

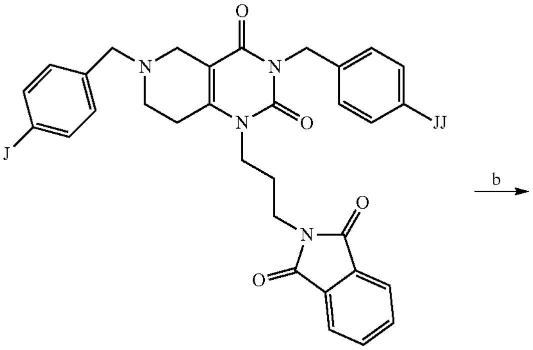

SS20

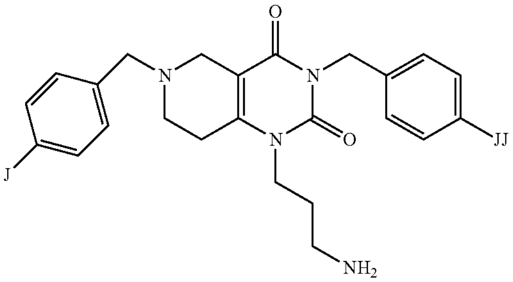

SS21

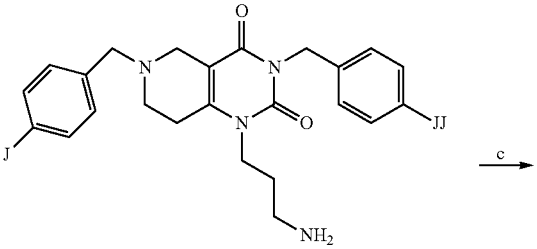

SS21

-continued

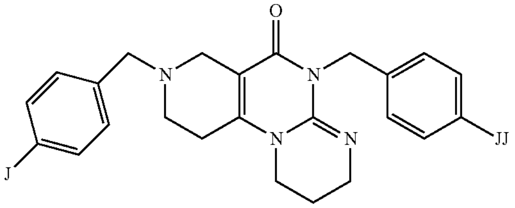

SS23

Synthesis of compounds by Scheme 5a: (a) sodium carbonate, DMF, 85° C. 5 h; (b) $CH_3NH_2$, EtOH, reflux, 80° C. 4 h; (c) pTSA, DMF, iPrOH, 80° C. 12 h.

Scheme 5B shows the preparation of compounds of the present invention as an alternative to the synthetic scheme shown in Scheme 5A.

Scheme 5B

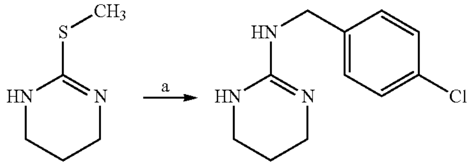

SS24 SS25

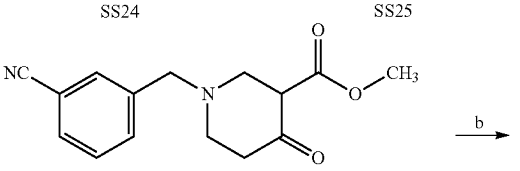

SS26

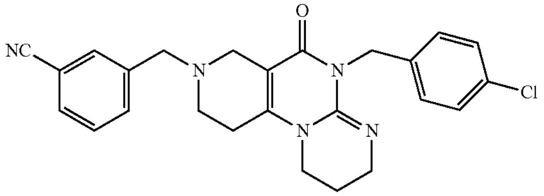

SS27

Synthesis of compounds by Scheme 5b: (a) 4-Cl-benzylamine, DMF, 85° C. 5 h; (b) SS25, cat p-TSA, EtOH, reflux, 80° C. 4 h.

Scheme 6 shows the preparation of amine protected alkylating agents. Alternative reaction conditions, known to those skilled in the art, may be employed for the various transformations in Scheme 6.

Scheme 6

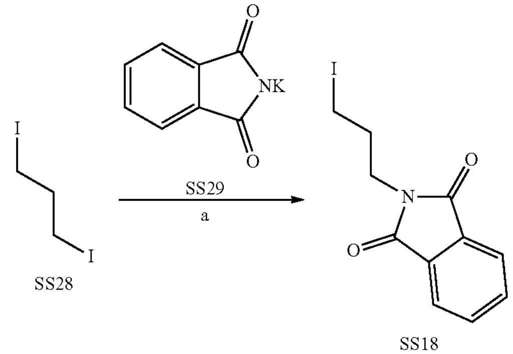

SS28 SS18

-continued

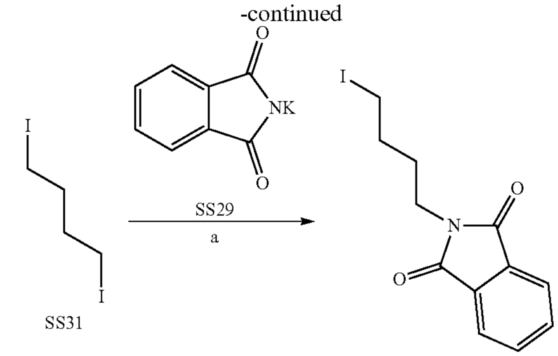

SS31 SS32

Synthesis of compounds by Scheme 6: (a) SS29, $K_2CO_3$, DMF.

Scheme 7 shows the preparation of various compounds of this invention using the following key reagents: SS33, SS35, SS37 and SS39. Using the chemistry disclosed herein, and in particular taking note of the conversion of shown as Schemes 5A, 5B and 6, shows a series of reactions that one skilled in the art may use to prepare compounds of the invention. Of particular note are the reaction conditions that facilitate alkylation reactions such as: sodium carbonate, DMF, 85° C. 12 h. J substituents denote various substituents that may be used for this reaction sequence and their positions on the molecule are not limited. This example is not to be limiting with regard to the number and type of substituents that may be used therein. Alternative reaction conditions, known to those skilled in the art, may be employed for the various transformations to prepare compounds in Scheme 7.

Scheme 7

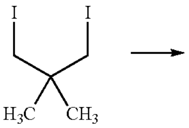

SS33

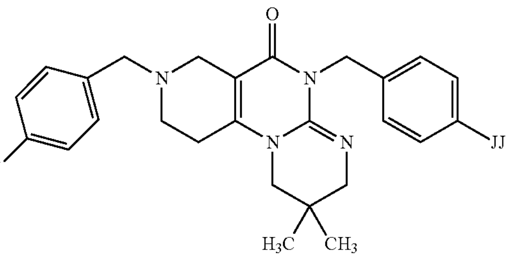

SS34

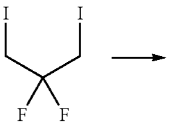

SS35

-continued

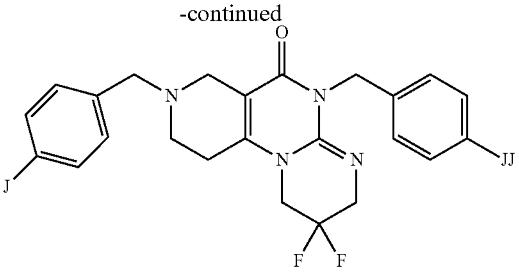

SS36

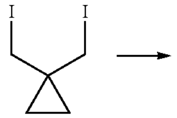

SS37

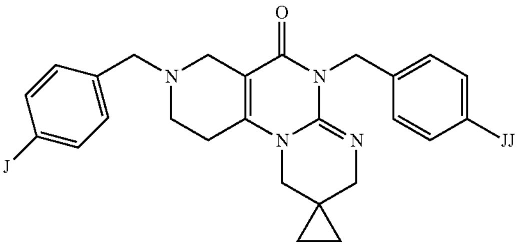

SS38

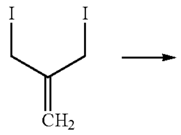

SS39

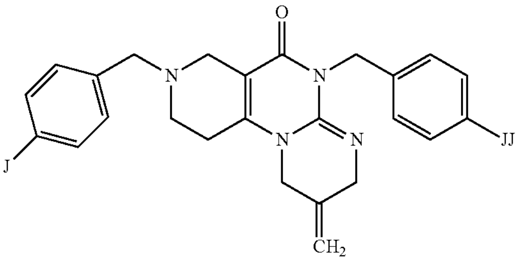

SS40

Scheme 8 shows the preparation of various compounds of this invention using the following key reagents: SS41, SS42, SS43, and SS44. Using the chemistry disclosed herein, and in particular taking note of the reaction sequence as shown in Scheme 5a and 5b, shows a series of reactions that one skilled in the art may use to prepare compounds of the invention. J substituents denote various substituents that may be used for this reaction sequence and their positions on their aromatic system are not limited. This example is not to be limiting with regard to the number and type of substituents that may be used therein. Alternative reaction conditions, known to those skilled in the art, may be employed for the various transformations to prepare compounds in Scheme 8.

Scheme 8

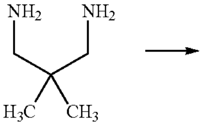

SS41

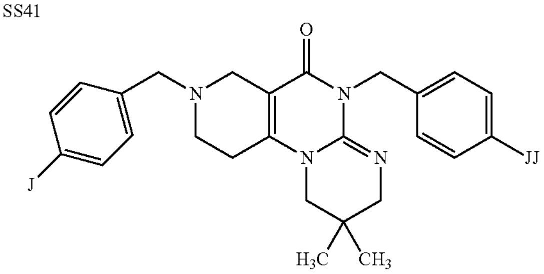

SS34

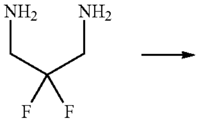

SS42

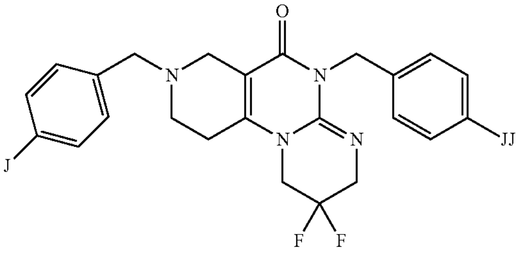

SS36

-continued

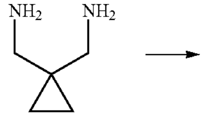

SS43

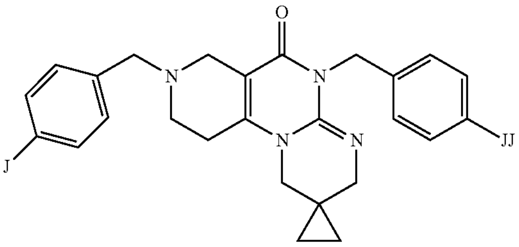

SS38

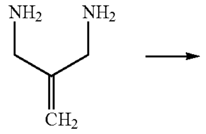

SS44

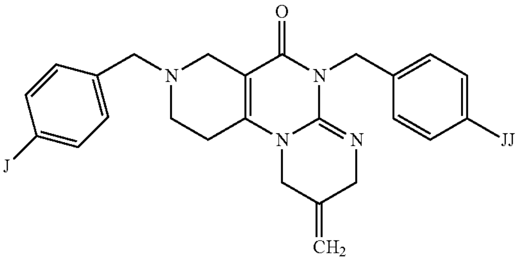

SS40

Scheme 9 shows the preparation of various compounds of this invention and in particular shows the uses of the key synthetic intermediates, SS40 and SS45. The terminal olefin of SS40 and the ketone residue of SS45 and be converted to many new analogs with reaction conditions known to those skilled in the art.

Scheme 9

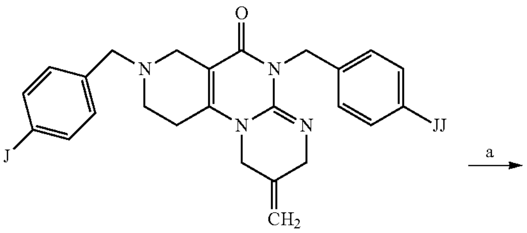

SS40

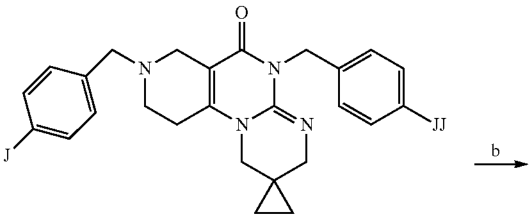

SS38

-continued

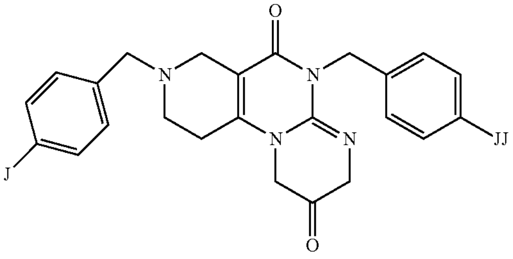

SS45

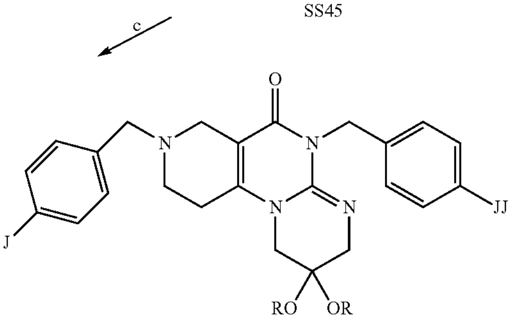

SS46

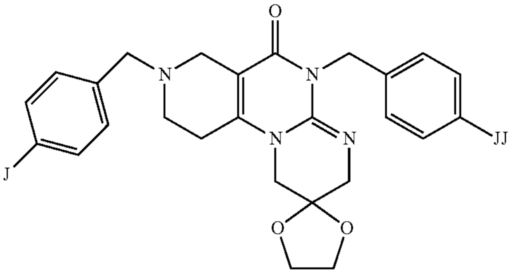

SS47

Synthesis of compounds by Scheme 9: (a) iodomethylzinc iodide, $Et_2O$ (Simmons-Smith reaction) or $(CH_3)_2S(O)CH_2$, DMSO, THF 50° C.; (b) $O_3$, $CH_2Cl_2$, -78° C. followed by $Me_2S$, AND (c) pTSA, DMF, ROH (or $HOCH_2CH_2OH$), 80° C. 12 h.

Scheme 10 is a general synthetic scheme to prepare compounds of this invention. This scheme together with other chemistry disclosed herein and that known to those skilled in the arts may be used to prepare compounds where Q is Q6. Especially chemistry of Schemes 4, 5a and 5b may be applied to this synthetic route.

Scheme 10

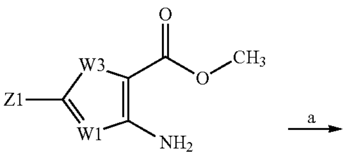

SS48

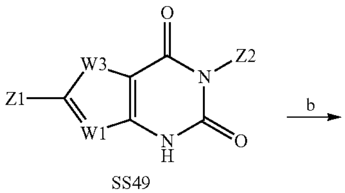

SS49

-continued

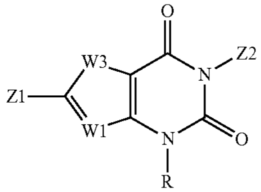

SS50

Synthesis of compounds by Scheme 10: (a) Z2—N=C=O, $Et_3N$, toluene, reflux, 80° C., 8 h and (b) RBr, $K_2CO_3$, DMF, 100° C., 12 h.

Scheme 11 is a general synthetic scheme to prepare compounds of this invention. This scheme together with other chemistry disclosed herein and that known to those skilled in the arts may be used to prepare compounds where Q is Q6. Note that SS51 is prepared as shown in Scheme 10 using chemistry described herein especially in Schemes 5a, 5b, 6, 7 and 8.

Scheme 11

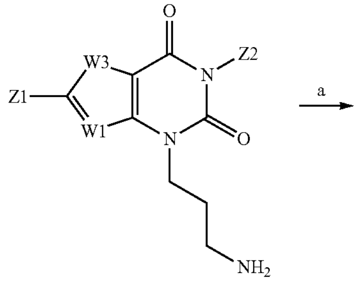

SS51

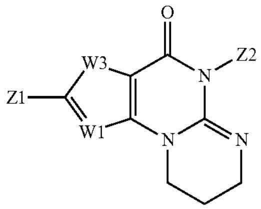

SS52

Synthesis of compounds by Scheme 11: (a) pTSA, DMF, iPrOH, 80° C. 12 h.

Scheme 12A and 12B are general synthetic schemes to prepare compounds of this invention. These schemes together with other chemistry disclosed herein and that known to those skilled in the arts may be used to prepare compounds where Q is Q8. Especially chemistry of Scheme 4 may be applied to this synthetic route. In addition, chemistry described in CN 104860948 and WO 2016/184437 may be used. SS53 may be prepared from the corresponding secondary amine through a reductive amination process using the corresponding aldehyde and a reducing agent to form the Z1 residue.

Scheme 12A

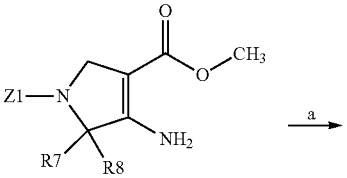

SS53

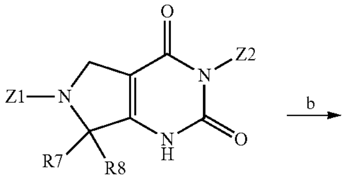

SS54

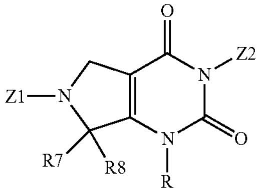

SS55

Synthesis of compounds by Scheme 12A: (a) Z2—NH(CO)Cl, $Et_3N$, toluene, reflux, 80° C., 8 h and (b) RBr, $K_2CO_3$, DMF, 100° C., 12 h.

Scheme 12B

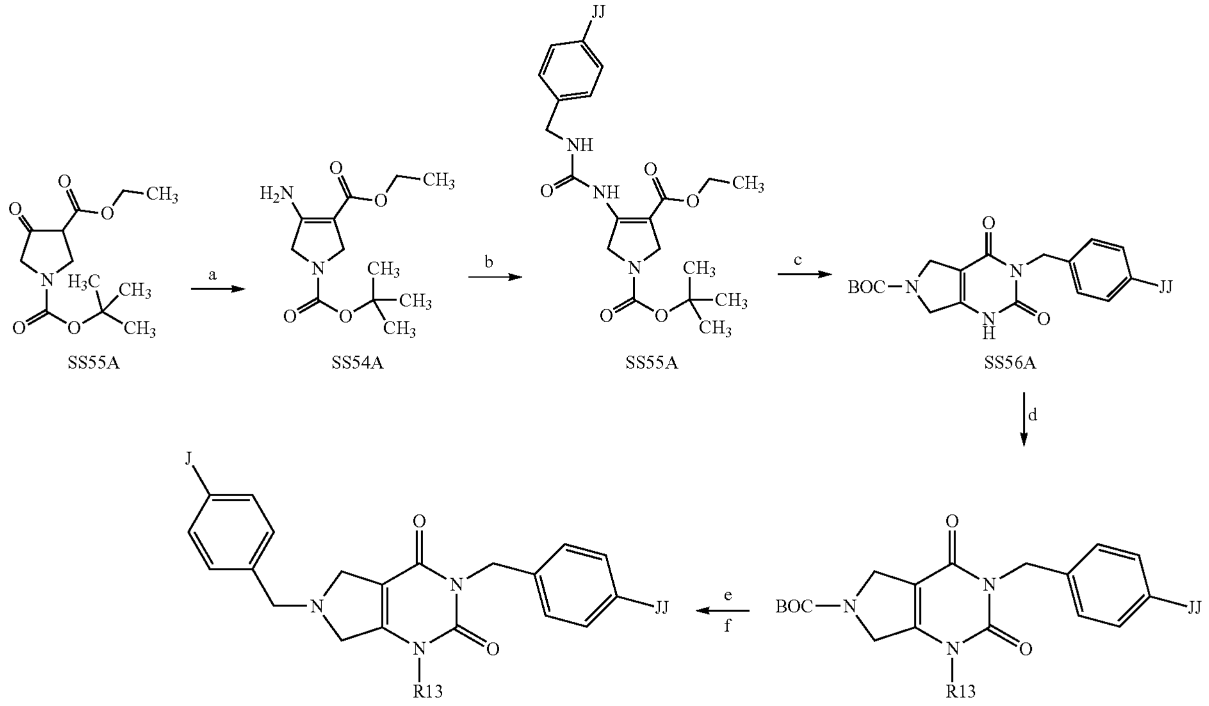

SS55A SS54A SS55A SS56A

SS58A SS57A

Synthesis of compounds by Scheme 12B: (a) $NH_3$, t-BuOH, (b) O═N═CH(Ph—JJ), TNF, (c) Toluene, $Et_3N$, 100° C. or toluene, cat p-TSA, 100° C. (d) R13—Br, $K_2CO_3$, DMF, 100° C., (e) TFA, $CH_2Cl_2$ and (f) $CH_3CN$, $BrCH_2Ph$—J, $Et_3N$.

Schemes 13A and 13B are general synthetic schemes to prepare compounds of this invention. These schemes together with other chemistry disclosed herein and that known to those skilled in the arts may be used to prepare compounds where Q is Q9. Note that SS56 is prepared as shown in Scheme 12 using chemistry described herein especially in Schemes 5a, 5b, 6, 7 and 8. Alternatively, SS57 may be prepared with the chemical sequence as given in Scheme 5b.

Scheme 13A

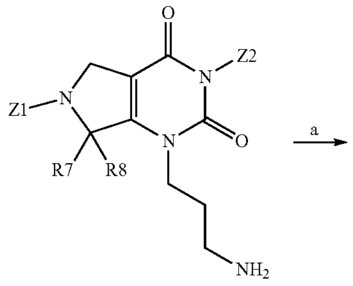

SS56

-continued

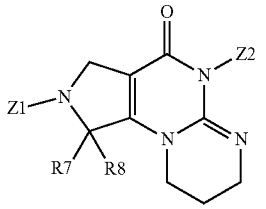

SS57

Synthesis of compounds by Scheme 13A: pTSA, DMF, iPrOH, 80° C. 12 h.

Scheme 13B

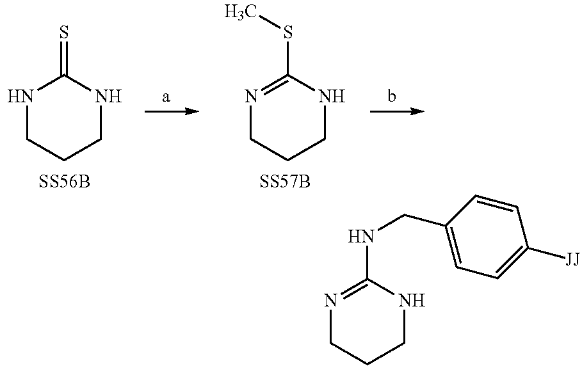

SS56B SS57B

SS58B

-continued

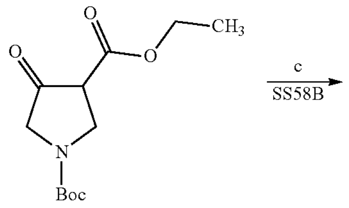

SS59B

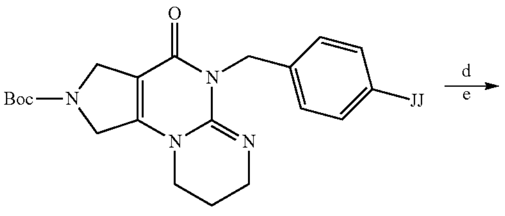

SS60B

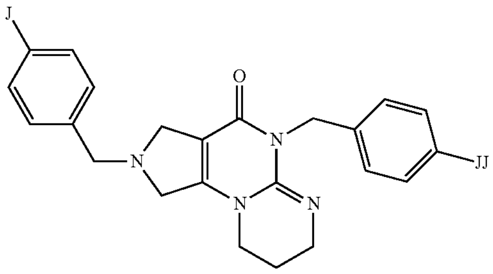

SS61B

Synthesis of compounds by Scheme 13B: a) MeI, $Et_3N$, THF, 50° C.; b) J-benzyl amine, THF reflux; c) $Et_3N$, toluene reflux; d) TFA, $CH_2Cl_2$; e) J-benzyl bromide, $Cs_2CO_3$.

Scheme 14 is a general synthetic scheme to prepare compounds of this invention. This scheme together with other chemistry disclosed herein and that known to those skilled in the arts may be used to prepare compounds of Formula 8A.

Scheme 14

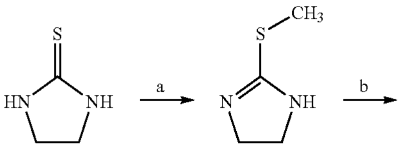

SS58 SS59

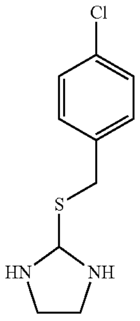

SS60

-continued

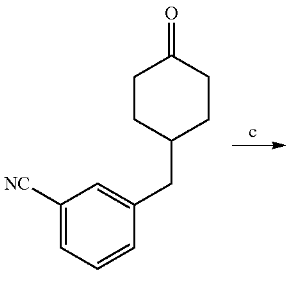

SS61

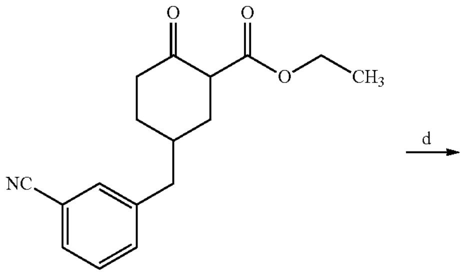

SS62

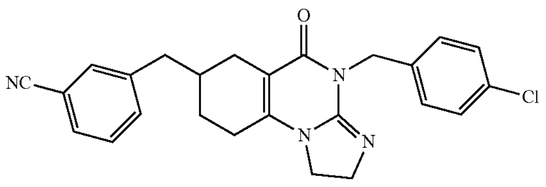

SS63

Synthesis of compounds by Scheme 14: (a) MeI, $Et_3N$, THF, 50° C.; (b) 4-Cl-benzyl amine, THF reflux; (c) Cl(CO)OEt, NaOEt, EtOH, 60° C.; (d) SS60, $Et_3N$, toluene reflux.

Scheme 15 is a general synthetic scheme to prepare compounds of this invention. This scheme together with other chemistry disclosed herein and that known to those skilled in the arts may be used to prepare compounds of Formula 9A.

Scheme 15

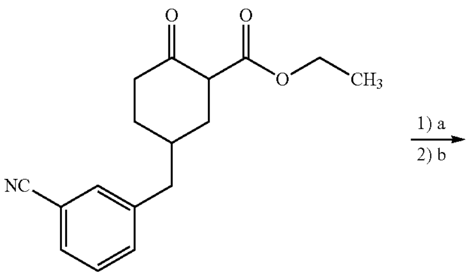

SS64

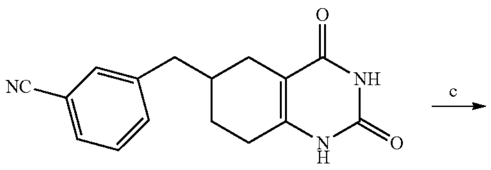

SS65

-continued

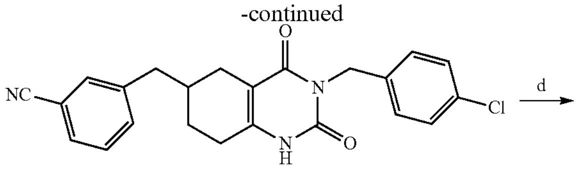

SS66

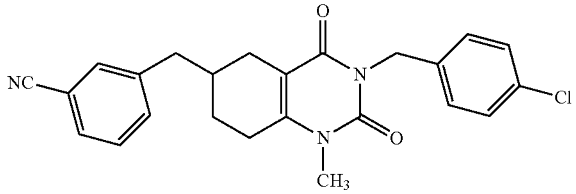

SS67

Synthesis of compounds by Scheme 15: (a) $NH_3$, cat. $NH_4Cl$, EtOH, reflux; (b) HN═C═O or equivalent, $Et_3N$, toluene reflux; (c) 4-Cl-benzyl bromide, $Et_3N$, DMF heat; (d) $K_2CO_3$, MeI, DMF heat.

A general synthetic scheme shown as Scheme 16, is a series of reactions that one skilled in the art may use to prepare compounds of the invention. The synthesis of S8 is shown however this is not meant to be limiting. This example is not to be limiting with regard to the number and type of substituents that may be used therein. Alternative reaction conditions, known to those skilled in the art, may be employed for the various transformations in Scheme 16. Additional information providing additional details for the synthesis of the compounds of the present invention are: 1) U.S. Pat. No. 10,597,380 and references cited therein, 2) WO 2008/109180 and references cited therein and 3) US 2019/0127349 and references cited therein, there are in no way meant to be limiting.

Scheme 16

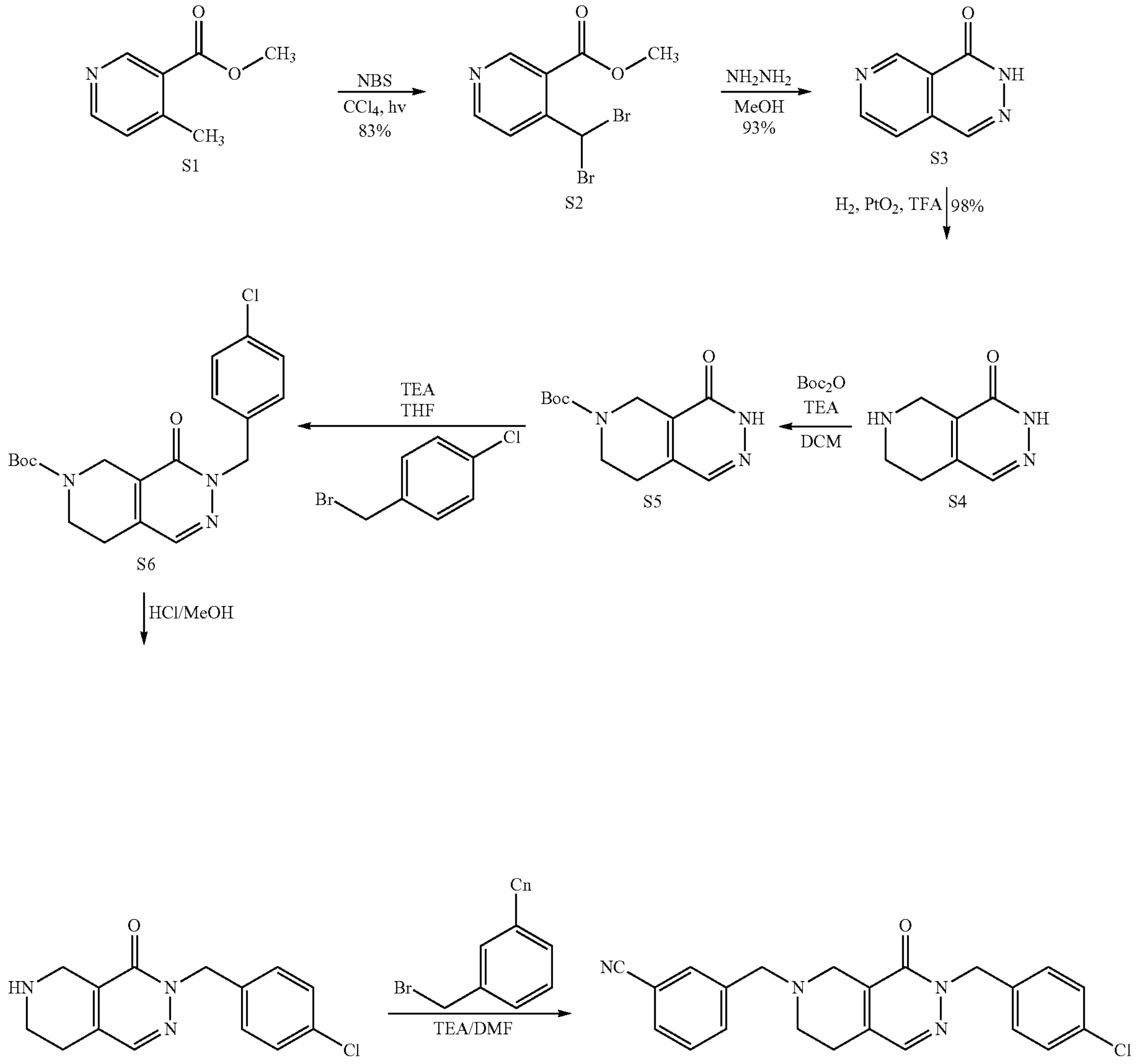

S1

S2

S3

S4

S5

S6

S7

S8

A general synthetic scheme as shown in Scheme 17, is a series of reactions that one skilled in the art may use to prepare compounds of the invention. Shown herein is the synthesis of S11. Central to this chemical synthetic route is the use of isocyanates here shown as S10. In the case the isocyanate required has the chemical formula of: $C_8H_6ClNO$. Alternative reaction conditions may be employed for the various transformations in Scheme 17. This example is not to be limiting with regard to the number and type of substituents that may be used therein.

Scheme 17

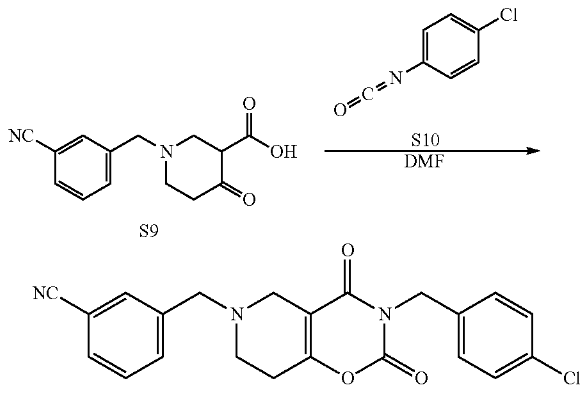

S9

S11

EXAMPLES

Chemistry Examples

The following show examples of the chemical compounds. In no way is this meant to be limiting.

Example 1

D9

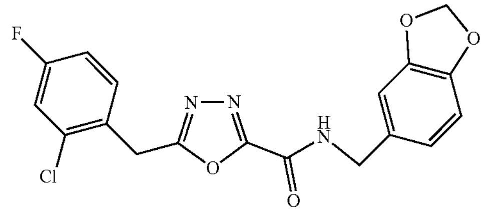

D9 was prepared as described in: Sieber S. A. et al, Angew. Chem. Int. Ed. 2008, 57, 14,602-14,607.

Examples 2-27

Examples 2-27 were prepared as described in: WO 2018 031987.

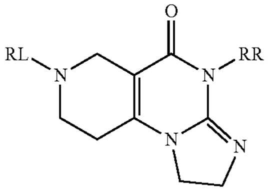

| Comp'd #/TR-# | RL | RR |
|---|---|---|
| 1 | 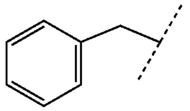 | 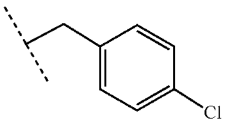 |
| 2/TR31 | 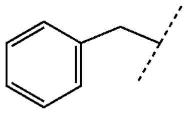 | 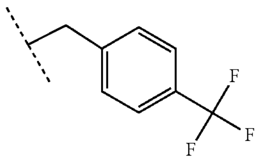 |
| 3 | 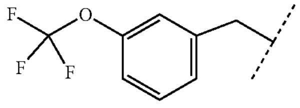 | 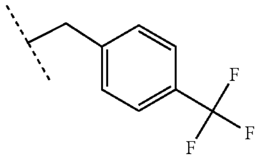 |
| 4 | 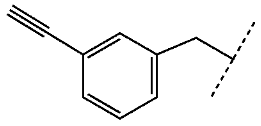 | 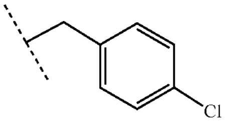 |

-continued
| Comp'd #/TR-# | RL | RR |
|---|---|---|
| 6 | 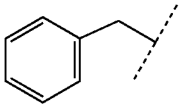 | 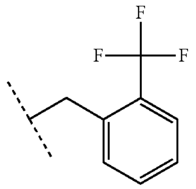 |
| 7 | 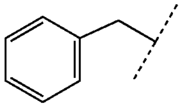 | 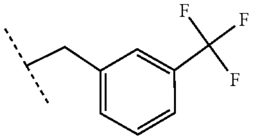 |
| 8 | 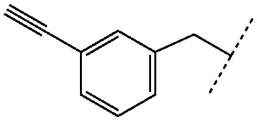 | 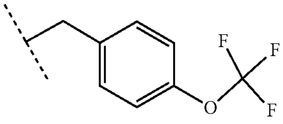 |
| 9 | 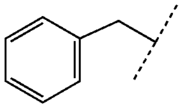 | 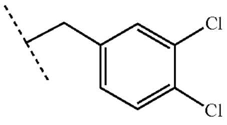 |
| 10 | 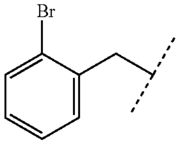 | 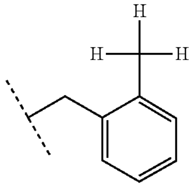 |
| 11 | 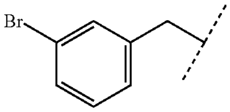 | 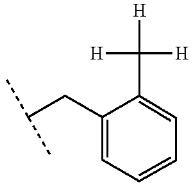 |
| 12 | 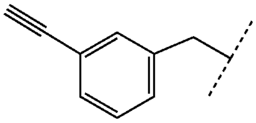 | 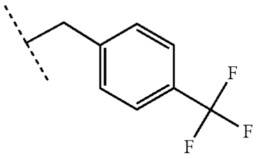 |
| 13 | 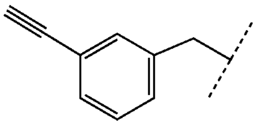 | 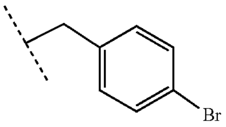 |
| 14/TR65 | 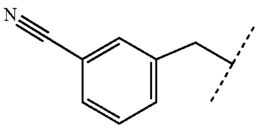 | 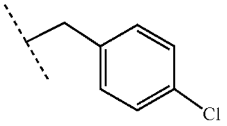 |

-continued
| Comp'd #/TR-# | RL | RR |
| --- | --- | --- |
| 15 | 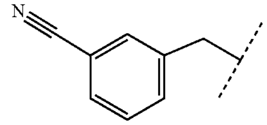 | 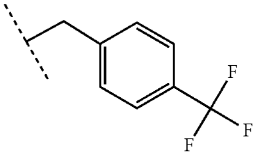 |
| 16 | 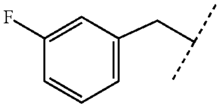 | 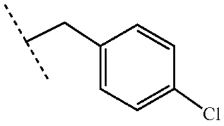 |
| 17 | 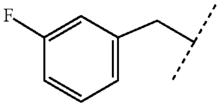 | 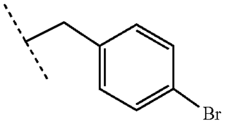 |
| 18 | 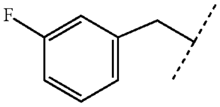 | 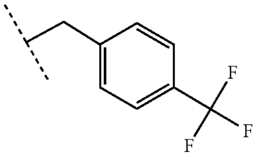 |
| 19 | 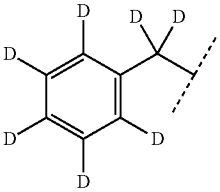 | 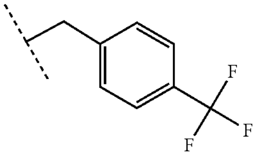 |
| 20 | 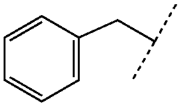 | 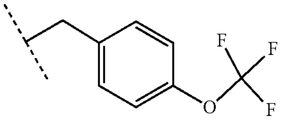 |
| 21 | 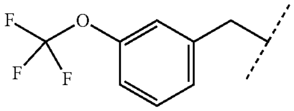 | 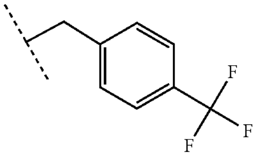 |
| 22 | 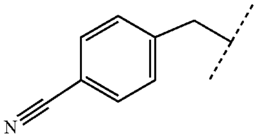 | 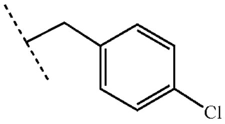 |
| 23 | 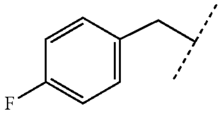 | 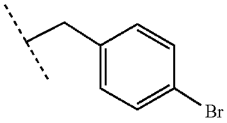 |
| 24 | 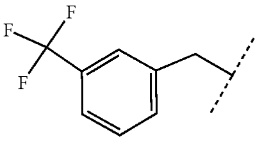 | 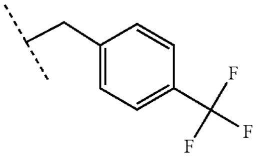 |

-continued
| Comp'd #/TR-# | RL | RR |
|---|---|---|
| 25 | 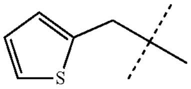 | 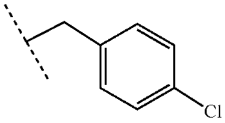 |
| 26 | 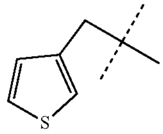 | 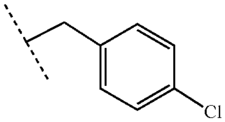 |
| 27 | 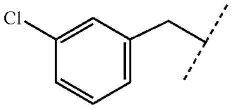 | 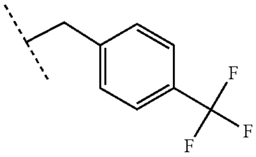 |
Example 5
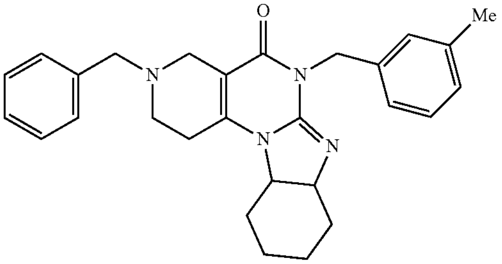
Examples 28-58
Examples 28-58 were prepared as described in: WO 2018 031990 and references cited therein.
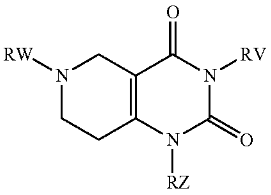
| Comp'd #/TR-# | RW | RV | RZ |
|---|---|---|---|
| 28 | 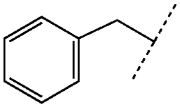 | 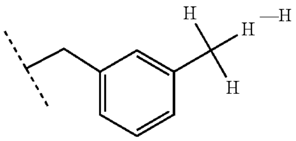 | |

-continued
| Comp'd #/TR-# | RW | RV | RZ |
| --- | --- | --- | --- |
| 29 | 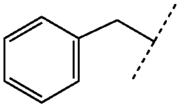 | 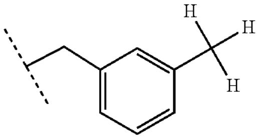 | —Me |
| 30 | 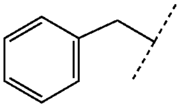 | 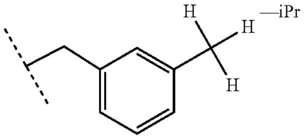 | —iPr |
| 31 | 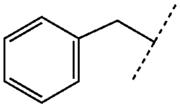 | 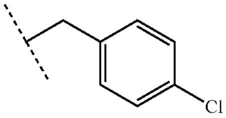 | —H |
| 32 | 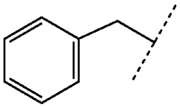 | 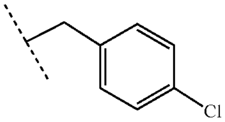 | —Me |
| 33 | 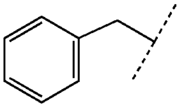 | 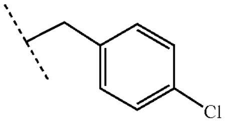 | —iPr |
| 34 | 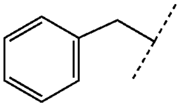 | 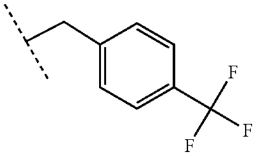 | —H |
| 35 | 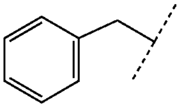 | 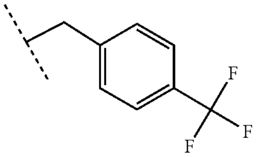 | —Me |
| 36 | 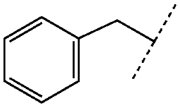 | 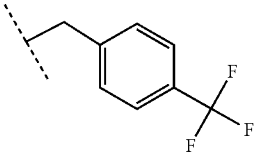 | —iPr |
| 37 | 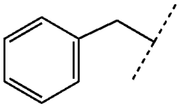 | 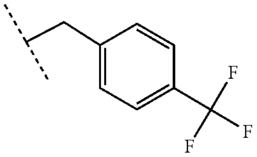 | —Et |
| 38 | 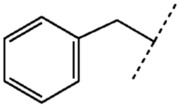 | 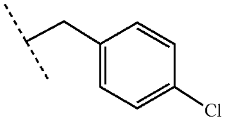 | —Et |

-continued
| Comp'd #/TR-# | RW | RV | RZ |
|---|---|---|---|
| 39 | 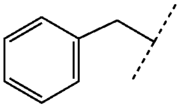 | 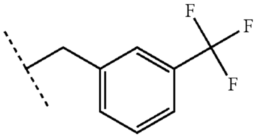 | —Me |
| 40 | 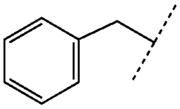 | 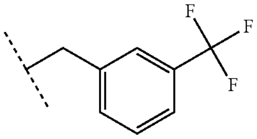 | —Et |
| 41 | 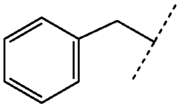 | 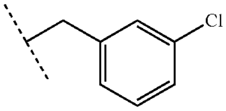 | —Me |
| 42 | 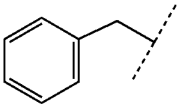 | 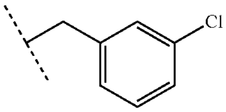 | —Et |
| 43 | 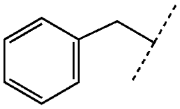 | 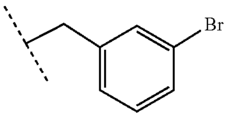 | —Me |
| 44 | 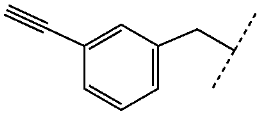 | 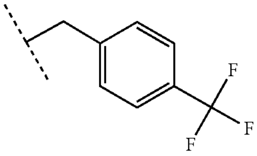 | —Me |
| 45 | 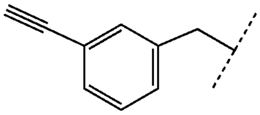 | 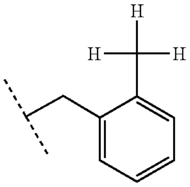 | —Me |
| 46 | 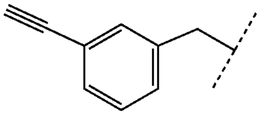 | 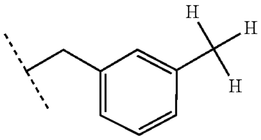 | —Me |
| 47 | 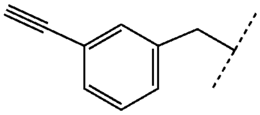 | 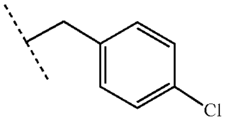 | —Me |
| 48 | 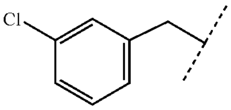 | 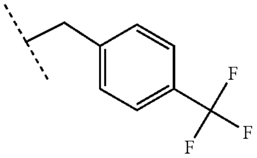 | —Me |

-continued
| Comp'd #/TR-# | RW | RV | RZ |
| --- | --- | --- | --- |
| 49 | 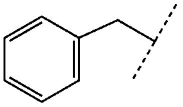 | 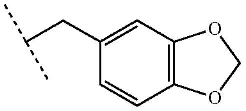 | —Me |
| 50 | 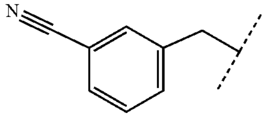 | 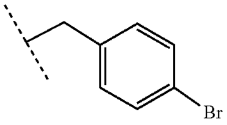 | —Me |
| 51/TR57 | 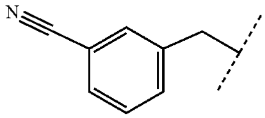 | 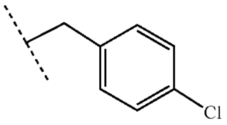 | —Me |
| 52 | 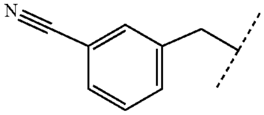 | 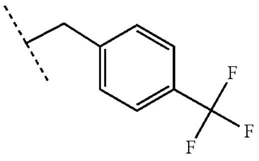 | —Me |
| 53 | 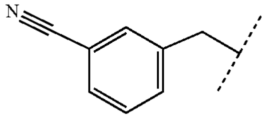 | 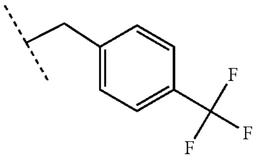 | —Et |
| 54 | 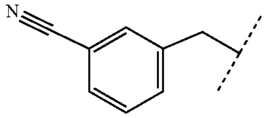 | 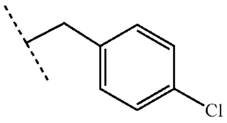 | —Et |
| 55 | 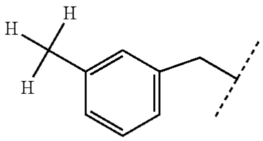 | 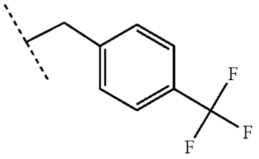 | —Me |
| 56 | 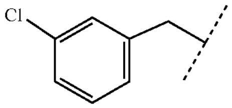 | 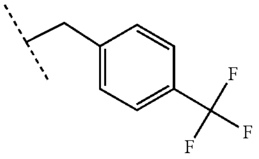 | —Me |
| 57 (TR79) | 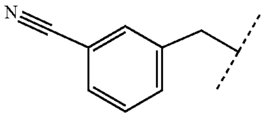 | 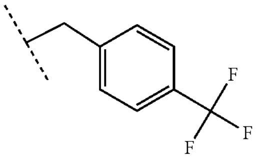 | $-(CH_2)_3NH_2$ |
| 58 (TR80) | 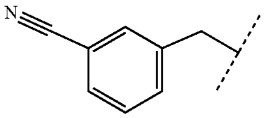 | 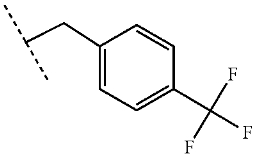 | $-(CH_2)_4NH_2$ |

-continued

| Comp'd #/TR-# | RW | RV | RZ |
|---|---|---|---|
| 59 (TR81) | 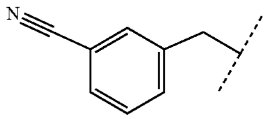 | 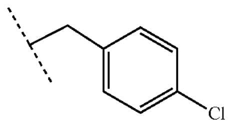 | —$(CH_2)_4NH_2$ |

Example 57

3-((1-(3-aminopropyl)-2,4-dioxo-3-(4-(trifluoromethyl)benzyl)-1,2,3,4,7,8-hexahydropyrido[4,3-d]pyrimidin-6(5H)-yl)methyl)benzonitrile

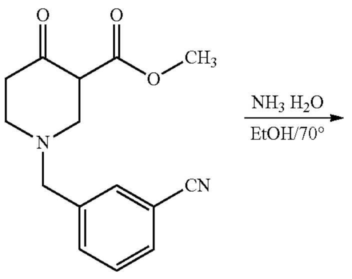

SS26

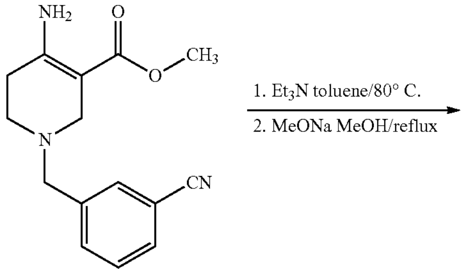

INT1

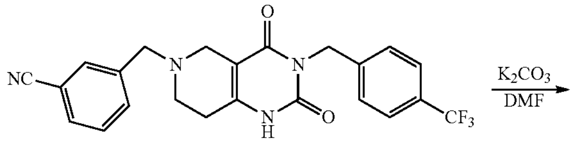

INT2

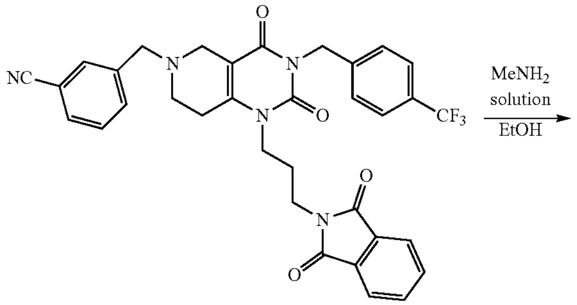

INT3

-continued

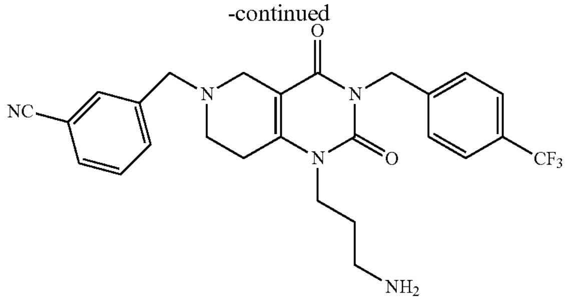

Example 57

Step 1: A mixture of methyl 1-(3-cyanobenzyl)-4-oxopiperidine-3-carboxylate SS26 (8.55 g, 31.4 mmol), and ammonia solution (7 ml, 25%) in ethanol (110 ml) was heated at 70° C. for 5 h. The solution was concentrated, extracted with DCM (2×300 ml) and washed with brine. The extracts were dried over $Na_2SO_4$ and evaporated under reduced pressure to give 8 g of 2-((4-amino-3-(methoxycarbonyl)-5, 6-dihydropyridin-1(2H)-yl) methyl)-4-cyanobenzen-1-ide INT2 (oil), which was directly used for next step.

Step 2: To a solution of INT2 (2 g, 7.4 mmol) in toluene 20 mL was added 1-(isocyanatomethyl)-4-(trifluoromethyl) benzene (1.6 g, 7.5 mmol) and triethylamine (1.1 g, 10.4 mmol). The solution was heated to 80° C. for 8 h. The reaction solution was cooled to rt and concentrated in vacuo. The formed white solid was filtered and dissolved in MeOH (20 ml). NaOMe (350 mg) was added and the mixture was refluxed overnight. Then ca 10-15 ml of methanol was removed and the precipitate was filtered. The desired product 3-((2,4-dioxo-3-(4-(trifluoromethyl)benzyl)-1,2,3,4,7,8-hexahydropyrido[4,3-d]pyrimidin-6(5H)-yl)methyl)benzonitrile, INT2 was obtained as a pale yellow solid (0.8 g, 25%).

Step 3: To a solution of INT2 (200 mg) in DMF (2 ml) was added potassium carbonate (150 mg) and 2-(3-iodopropyl) isoindoline-1,3-dione (150 mg). The mixture was heated at 100° C. for 12 h. Water (ca 3 ml) was added and the solution was extracted with EtOAc (3×5 ml). The combined extracts were washed with brine 3 times (ca 5 ml), dried over $Na_2SO_4$, filtered and concentrated in vacuo to yield the crude product. The purified product, INT3 was obtained by preparative TLC, 100 mg, Yield 35%.

Step 4: To a solution of product, INT3 (100 mg) in EtOH (3 ml) was added methylamine solution (0.25 ml, 30%). The mixture was heated at 80° C. for 4 h. The water was added and the solution was extracted with DCM (3×3 ml). The combined organic extracts were dried over $Na_2SO_4$, filtered and concentrated in vacuo to yield the crude product, Example 57. The final product Example 57 was obtained by preparative HPLC, 15 mg, Yield 19%.

$^1$HNMR (400 MHz, $CD_3OD$) δ 2.03 (t, J=7.2 Hz, 2H), 2.99 (t, J=6.8 Hz, 2H), 3.18 (s, 2H), 3.67 (s, 2H), 4.01 (t, J=6.8 Hz, 2H), 4.07 (s, 2H), 4.62 (s, 2H), 5.17 (s, 2H), 7.5-7.57 (m, 4H), 7.69 (t, J=8 Hz, 1H), 7.86-7.93 (m, 2H), 7.99 (s, 1H); LC-MS: m/z=498.1(M+1).

Example 58

3-((1-(4-aminobutyl)-2,4-dioxo-3-(4-(trifluoromethyl)benzyl)-1,2,3,4,7,8-hexahydropyrido[4,3-d]pyrimidin-6(5H)-yl)methyl)benzonitrile Example 58

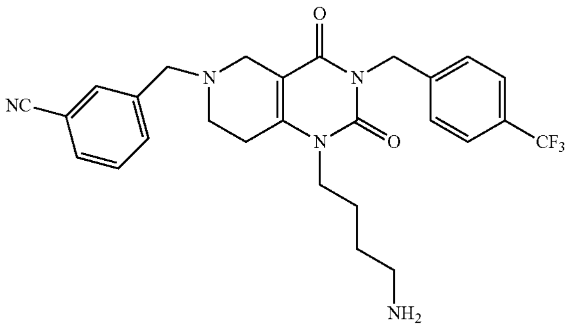

Example 58 is prepared in a similar fashion as Example 57.

$^1$HNMR (400 MHz, $CD_3OD$) δ 1.7 (s, 4H), 2.95 (s, 2H), 3.16 (s, 2H), 3.64 (s, 2H), 3.9 (s, 2H), 4.03 (s, 2H), 4.59 (s, 2H), 5.15 (s, 2H), 7.49-7.57 (m, 4H), 7.67-7.7 (m, 1H), 7.88 (t, J=8 Hz, 2H), 7.98 (s, 1H); LC-MS: m/z=512.2(M+1).

Example 59

3-((1-(4-aminobutyl)-3-(4-chlorobenzyl)-2,4-dioxo-1,2,3,4,7,8-hexahydropyrido[4,3-d]pyrimidin-6(5H)-yl)methyl)benzonitrile Example 59

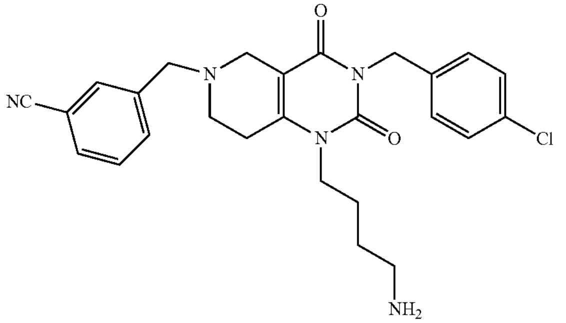

Example 59 is prepared in a similar fashion as Example 57.

$^1$HNMR (400 MHz, $CD_3OD$) δ 1.72 (s, 4H), 2.98-2.99 (d, 2H), 3.15-3.17 (d, 2H), 3.61 (t, J=5.6 Hz, 2H), 3.91-3.93 (d, 2H), 4.01 (s, 2H), 4.57 (s, 2H), 5.08 (s, 2H), 7.28-7.3 (d, 2H), 7.35-7.37 (d, 2H), 7.71 (t, J=7.6 Hz, 1H), 7.9-7.92 (d, 2H), 7.99 (s, 1H).

Example 60

11-benzyl-7-[(2,4-difluorophenyl)methyl]-2,5,7,11-tetraazatricyclo[7.4.0.0$^{2,6}$]trideca-1(9),5-dien-8-one Example 60

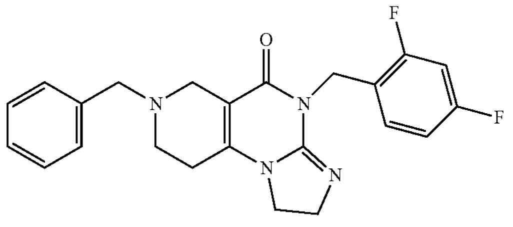

Example 60 was prepared as described in: WO 2018 031987.

Example 61

3-({3-[(4-chlorophenyl)methyl]-2-methyl-4-oxo-3H,4H,5H,6H,7H,8H-pyrimidin-6-yl}methyl)benzonitrile Example 61

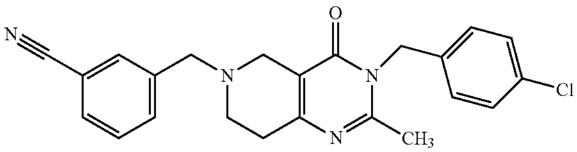

Synthesis of example 61 was carried out by the following scheme:

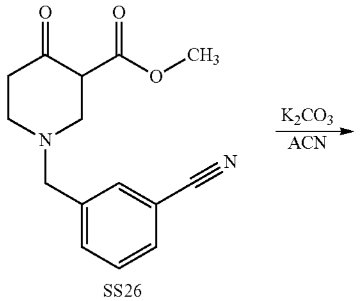

SS26

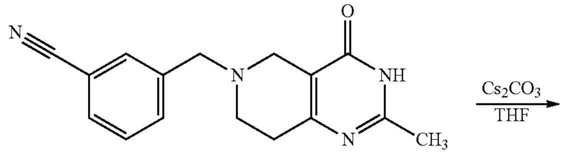

INT4

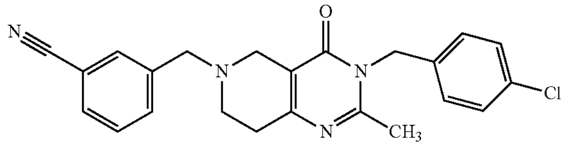

Compound 61

To a 10 mL three necked flask, was charged with SS26 (0.4 mmol), acetamidine hydrochloride (0.4 mmol), methanol (3 mL) and $K_2CO_3$ (1.2 mmol). The mixture was refluxed for 12~15 h hours. LC-MS confirmed that the reaction was complete. The reaction was cooled down to room temperature and half of the solvent was removed under vacuum. Water (2 mL) was added drop wise. White solid precipitated, was filtered and washed with water. The solid was dried under vacuum to afford INT4 (yield 72%).

To a 10 mL three necked flask, was charged with INT4 (0.4 mmol), 1-(0.4 mmol), THF (3 mL) and $Cs_2CO_3$ (1.2 mmol). The mixture was refluxed for 12~15 h hours. LC-MS confirmed that the reaction was complete. The solution was washed with water (100 mL×2), brine (100 mL×1). The combined organic layers dried over $Na_2SO_4$, purified by silica gel column to afford Example 61 (yield 30%).

$^1$HNMR (400 MHz, $CDOD_3$) δ 7.78 (s, 1H), 7.72-7.74 (d, J=8 Hz, 1H), 7.65-7.67 (d, J=8 Hz, 1H), 7.54 (t, J=8 Hz, 1H), 7.34-7.36 (d, J=8 Hz, 2H), 7.17-7.19 (d, J=8 Hz, 2H), 5.32 (s, 2H), 3.81 (s, 2H), 3.41 (s, 2H), 2.81 (t, J=6 Hz, 2H), 2.74 (t, J=5.2 Hz, 2H), 2.46 (s, 3H); LC-MS: m/z=404.9 (M).

Example 62 (TR98)

3-[(8-oxo-9-{[4-(trifluoromethyl)phenyl]methyl}-1,5,9,11-tetraazatricyclo[8.4.0.0$^{2,7}$]tetradeca-2(7),10-dien-5-yl)methyl]benzonitrile Example 62

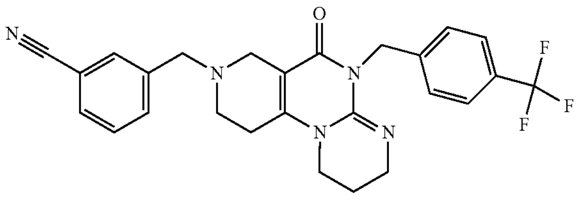

Example 62 was prepared with the following scheme:

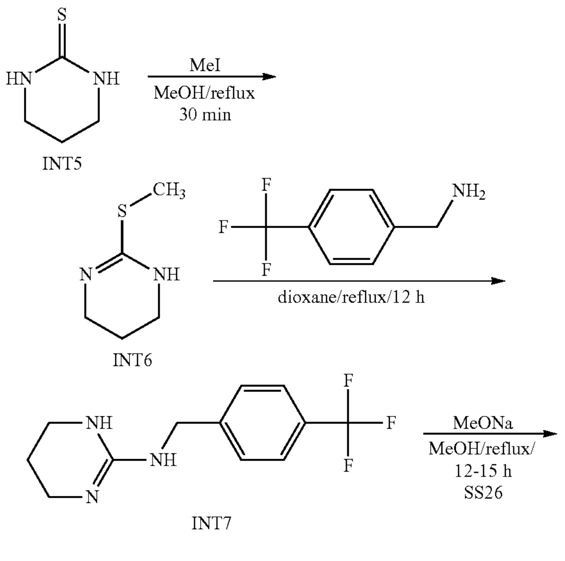

-continued

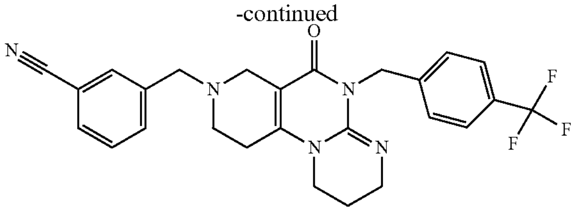

Example 62

Imidazolidine-2-thione (59.8 mmol) INT5, was dissolved in methanol (70 mL), $CH_3I$ (89.7 mmol) was added dropwise at 25° C. After refluxing for 30 minutes, the solvent was removed under vacuum. The residue was suspended in MTBE (50 mL), and filtered. The solid was dried under vacuum to afford INT6 (yield 83%) as white solid.

Compound INT6 (2 mmol), and ((4-trifluoromethyl)phenyl)methyl amine (4.2 mmol) was dissolved in dioxane (5 mL). The mixture was refluxed for 12 hours. The LC-MS confirmed that the reaction was completed. The solvent was removed, and the residue was suspended in toluene for 12 hours. The suspension was filtered and filtered cake was dried under vacuum to afford compound INT7.

To a 10 mL three necked flask, was charged with compound INT7 (0.4 mmol), SS26 (0.4 mmol), methanol (3 mL) and MeONa (1.2 mmol). The mixture was refluxed for 12~15h hours. LC-MS confirmed that the reaction was complete. The reaction was cooled down to room temperature. Half of the solvent was removed under vacuum. Water (2 mL) was added drop wise. White solid precipitated, was filtered and washed with water. The solid was dried under vacuum to afford Example 62 (yield 25%).

$^1$H-NMR (400 MHz, $CD_3OD$): δ 7.64-7.77 (m, 4H), 7.52-7.57 (m, 2H), 7.38-7.45 (m, 2H), 5.25 (s, 1H), 5.20 (s, 1H), 3.72-3.88 (m, 4H), 3.42 (s, 2H), 3.26 (s, 2H), 2.57-2.76 (m, 4H), 1.86-1.91 (m, 2H).

LCMS [mobile phase: from 20% water (0.05% $NH_3.H_2O$) and 80% $CH_3CN$ (0.05% $NH_3.H_2O$) to 5% water (0.05% $NH_3.H_2O$) and 95% $CH_3CN$ (0.05% $NH_3.H_2O$) in 6.0 min (linear gradient, C18 (50 mm, 5 micron, 1 micron injection) column), under these conditions for 0.5 ml/min.] purity is 97.5%, Rt=3.6 min; MS Calcd.:479.5. MS Found: 480.1[M+1]+).

Example 63

N-[(4-chlorophenyl)methyl]-5-[(3-cyanophenyl)methyl]-1,3,4-oxadiazole-2-carboxamide Example 63

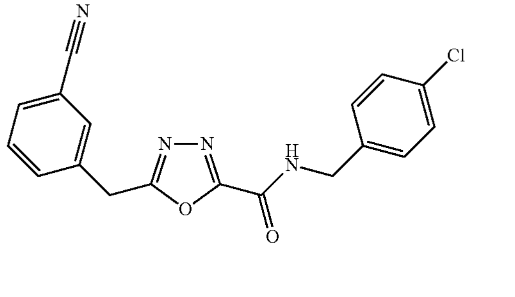

Example 63 is made by the following synthetic scheme:

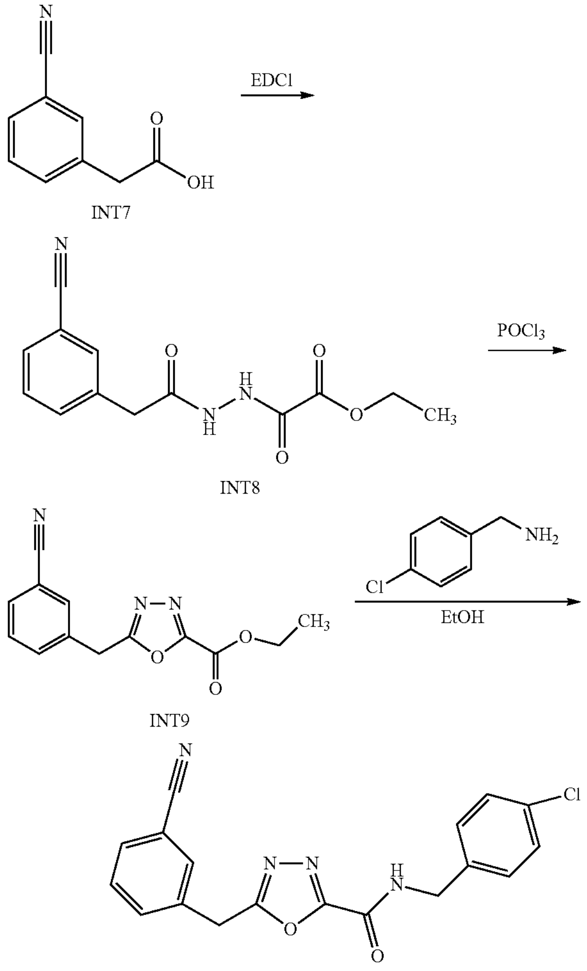

Example 63

$^1$HNMR (400 MHz, DMSO_d$_6$): δ 9.83 (s, 1H), 7.72-7.87 (m, 3H), 7.6 (t, J=8 Hz, 1H), 7.38 (t, J=7.2 Hz, 4H), 4.44 (t, J=4.8 Hz, 4H); LC-MS: m/z=352.9 (M+)

Example 64

7-[(4-chlorophenyl)methyl]-11-[(3-oxo-2,3-dihydro-1H-inden-5-yl)methyl]-2,5,7,11-tetraazatricyclo[7.4.0.0$^{2,6}$]trideca-1(9),5-dien-8-one Example 64

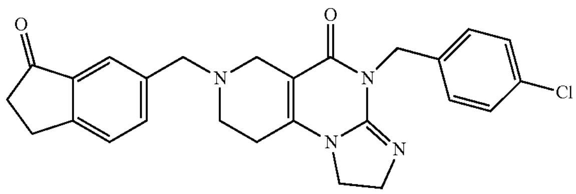

Example 64 is made by the following synthetic scheme:

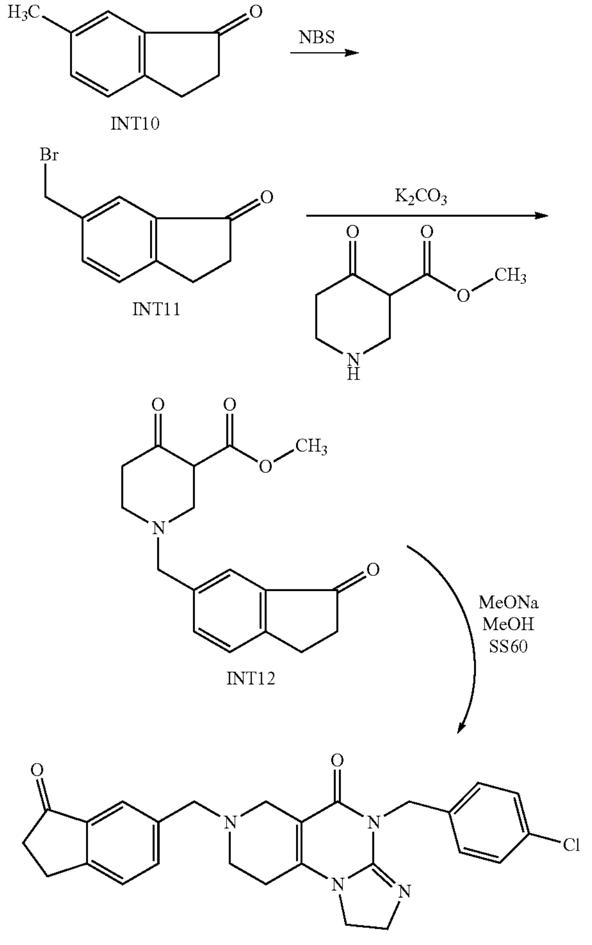

Example 64

$^1$HNMR (400 MHz, CDCl$_3$) δ 2.46 (s, 3H), 2.75-7.92 (m, 5H), 3.05 (s, 1H), 3.43-3.46 (d, J=12 Hz, 1H), 3.62-3.66 (d, J=16 Hz, 1H), 4.07 (s, 2H), 4.21 (s, 2H), 4.99 (s, 1H), 5.21 (s, 2H), 7.29 (s, 2H), 7.33-7.35 (d, J=8 Hz, 2H), 7.53-7.55 (d, J=8 Hz, 1H), 7.63-7.64 (d, J=8 Hz, 2H); LC-MS: m/z=460.9 (M+1).

Example 65

3-({3-[(4-chlorophenyl)methyl]-4-oxo-3H,4H,5H,6H,7H,8H-pyrido[4,3-d]pyrimidin-6-yl}methylbenzonitrile Example 65

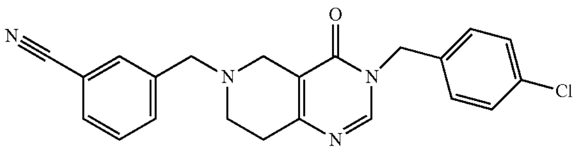

Example 65 is made by the following synthetic scheme:

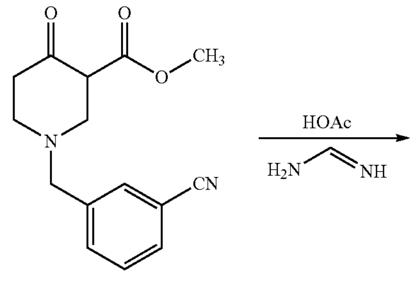

INT13

-continued

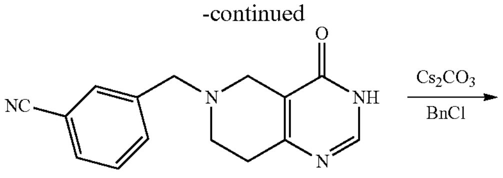

INT14

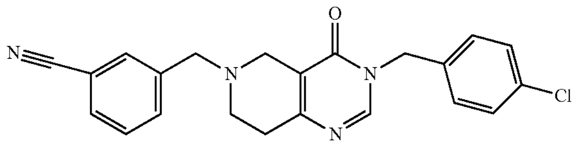

Example 65

$^1$HNMR (400 MHz, $CDCl_3$) δ 3.06 (s, 2H), 3.42 (s, 2H), 3.92 (s, 2H), 4.35 (s, 2H), 5.03 (s, 2H), 7.24 (s, 2H), 7.33-7.35 (d, J=8 Hz, 2H), 7.6 (t, J=8 Hz, 1H), 7.72-7.81 (m, 3H), 8.14 (s, 1H); LC-MS: m/z=390.9(M+1)

Example 66 (TR108)

3-({8-[(4-chlorophenyl)methyl]-7-oxo-1,4,8,10-tetraazatricyclo[7.3.0.0$^{2,6}$]dodeca-2(6),9-dien-4-yl}methylbenzonitrile Example 66

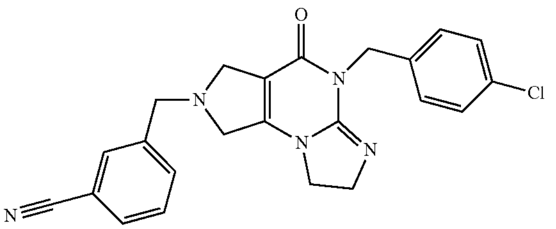

Example 66 is made by the following synthetic scheme:

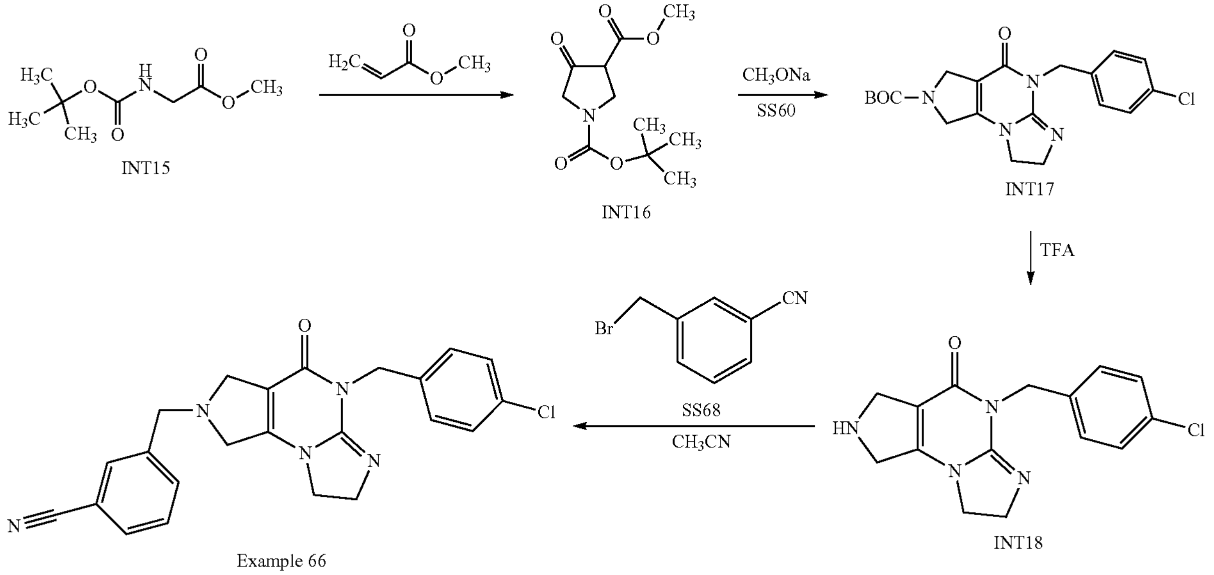

INT15 INT16 INT17 INT18 Example 66

$^1$HNMR (400 MHz, $CDCl_3$) δ 3.72-3.98 (m, 10H), 5.0 (s, 2H), 7.24 (s, 1H), 7.39-7.47 (m, 4H), 7.57-7.59 (d, J=8 Hz, 2H), 7.66 (s, 1H); LC-MS: m/z=418 (M+1).

Example 67 (TR109)

3-[(5-oxo-4-{[4-(trifluoromethyl)phenyl]methyl}-1H,2H,4H,5H,6H,7H,8H,9H-imidazo[1,2-a]quinazolin-7-yl)methyl]benzonitrile Example 67

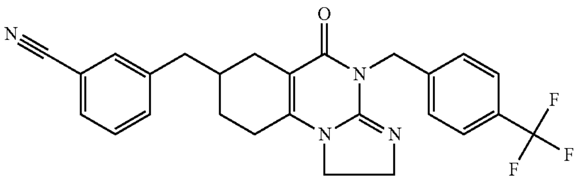

Example 67 is made by the following synthetic scheme:

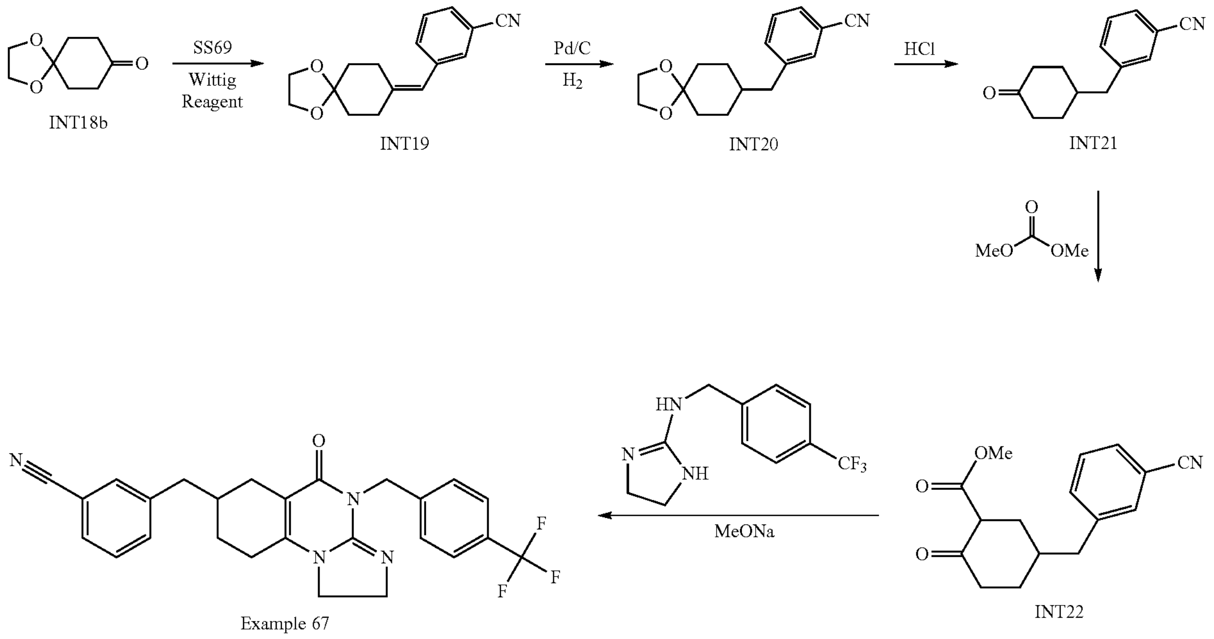

$^1$HNMR (400 MHz, $CDCl_3$) δ 1.36-1.4 (m, 1H), 1.8-1.95 (m, 3H), 2.37-2.75 (m, 5H), 3.87-3.97 (m, 4H), 5.1 (s, 2H), 7.39-7.57 (m, 8H); LC-MS: m/z=465 (M+1).

Example 68 (TR122)

3-({4-[(4-chlorophenyl)methyl]-5-oxo-1H,2H,4H,5H,6H,7H,8H,9H-imidazo[1,2-a]quinazolin-7-yl}methyl)benzonitrile Example 68

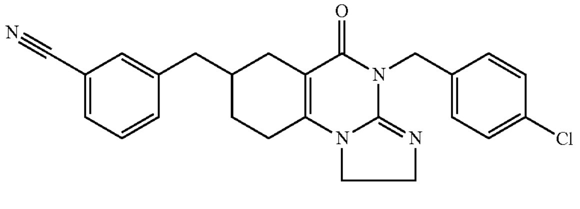

Example 68 is made by the synthetic sequence described for Example 67.

$^1$HNMR (400 MHz, $CDCl_3$) δ 1.32-1.42 (m, 1H), 1.81-1.94 (m, 3H), 2.31-2.74 (m, 5H), 3.86-3.96 (m, 4H), 5.01 (s, 2H), 7.25 (t, J=5.6 Hz, 2H), 7.37-7.45 (m, 5H), 7.51 (t, J=4 Hz, 1H); LC-MS: m/z=431 (M+1).

Example 69

3-({3-[(4-chlorophenyl)methyl]-2-methyl-4-oxo-3H,4H,5H,6H,7H-pyrrolo[3,4-d]pyrimidin-6-yl}methyl)benzonitrile Example 69

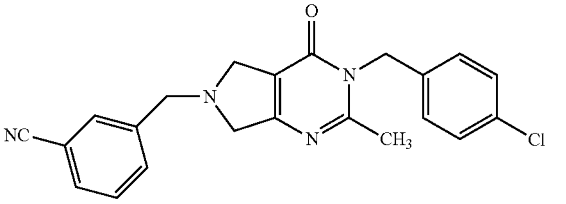

Example 69 is made by the following synthetic scheme:

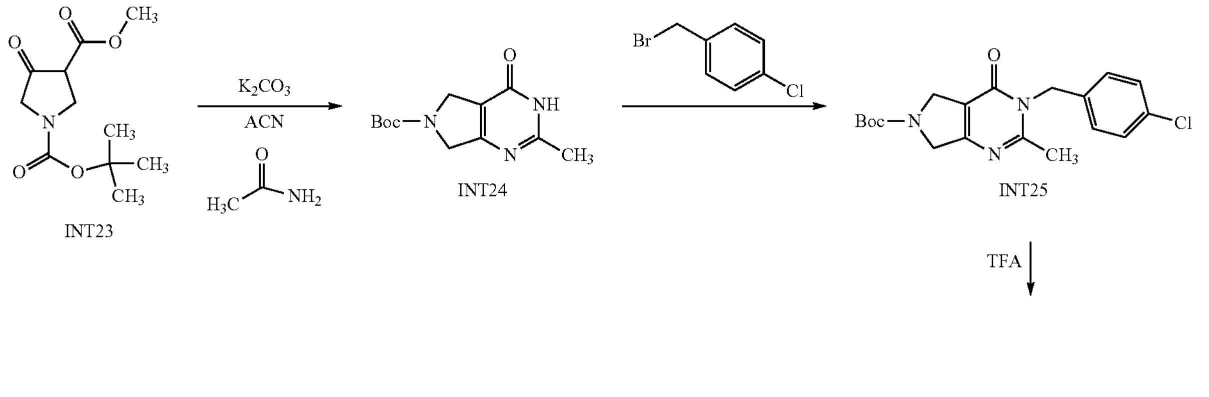

-continued
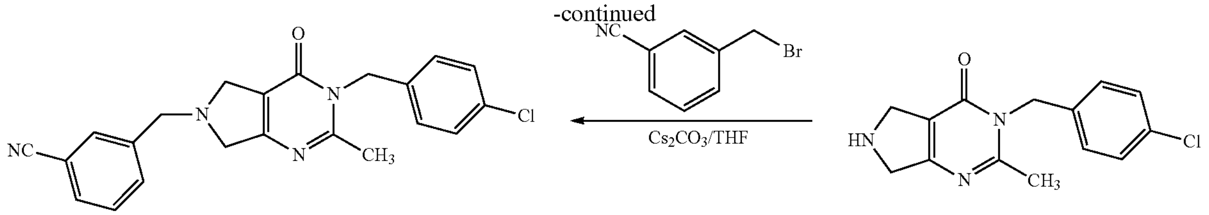
Example 69
$^1$HNMR (400 MHz, $CDCl_3$) δ 2.51 (s, 3H), 4.46-4.48 (ss, 6H), 5.26 (s, 2H), 7.11-7.13 (d, J=8 Hz, 2H), 7.33-7.35 (d, J=8 Hz, 2H), 7.63 (t, J=8 Hz, 1H), 7.74-7.79 (m, 2H), 7.85-7.87 (d, J=8 Hz, 1H); LC-MS: m/z=390.9 (M+1).
Example 70
3-({9-[(4-chlorophenyl)methyl]-13,13-dimethyl-8-oxo-1,5,9,11-tetraazatricyclo[8.4.0.0$^{2,7}$]tetradeca-2(7),10-dien-5-yl}methyl)benzonitrile
Example 70
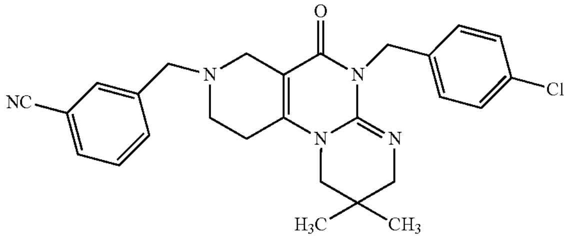
Example 70 is made by the following synthetic scheme:
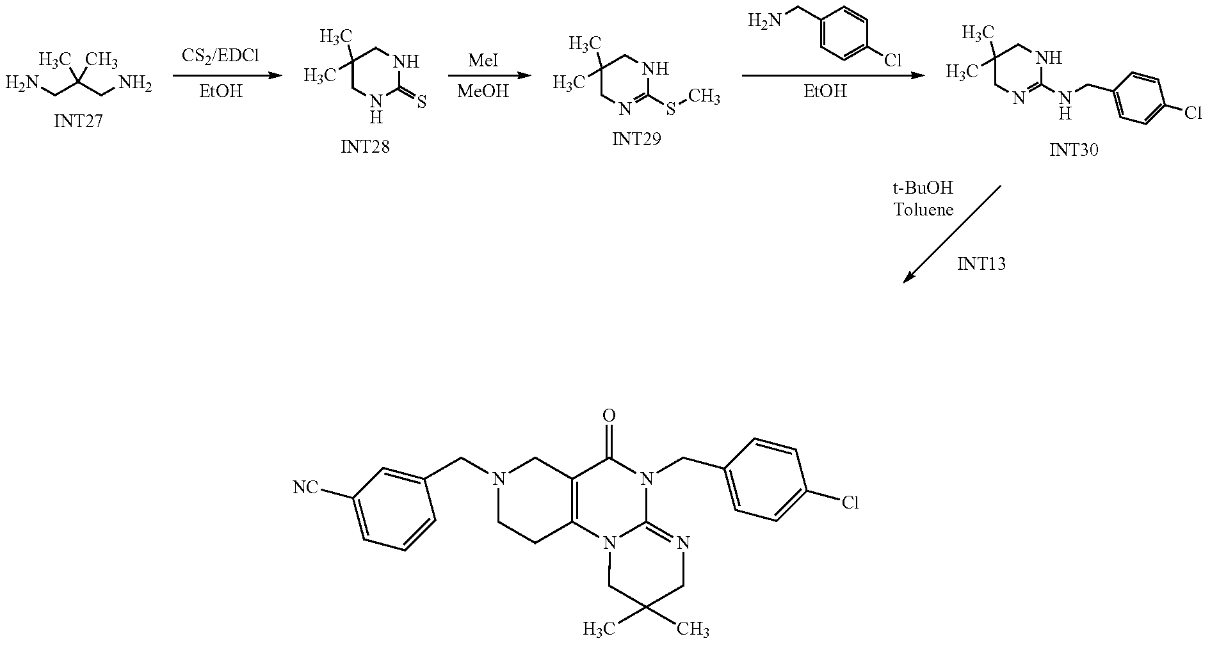
Example 70

$^1$HNMR (400 MHz, $CDCl_3$) δ 1.03 (s, 6H), 2.98 (s, 2H), 3.1-3.17 (m, 4H), 3.59-3.68 (m, 4H), 3.75 (s, 2H), 4.15 (s, 2H), 5.25 (s, 2H), 7.28-7.3 (d, J=8 Hz, 2H), 7.40-7.42 (d, J=8 Hz, 2H), 7.65 (t, J=8 Hz, 1H), 7.8-7.82 (d, J=8 Hz, 1H), 7.86-7.88 (d, J=8 Hz, 1H), 7.93 (s 1H); LC-MS: m/z=473.9 (M+1).

Example 71

3-({9-[(4-chlorophenyl)methyl]-13,13-difluoro-8-oxo-1,5,9,11-tetraazatricyclo[8.4.0.0$^{2,7}$]tetradeca-2(7),10-dien-5-yl}methyl)benzonitrile Example 71

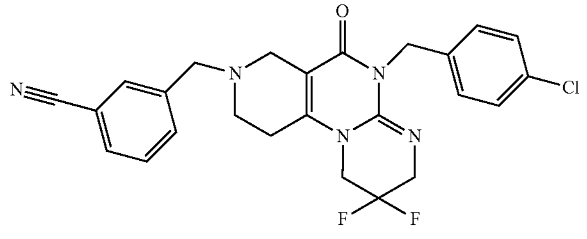

Example 72 is made by the following synthetic scheme:

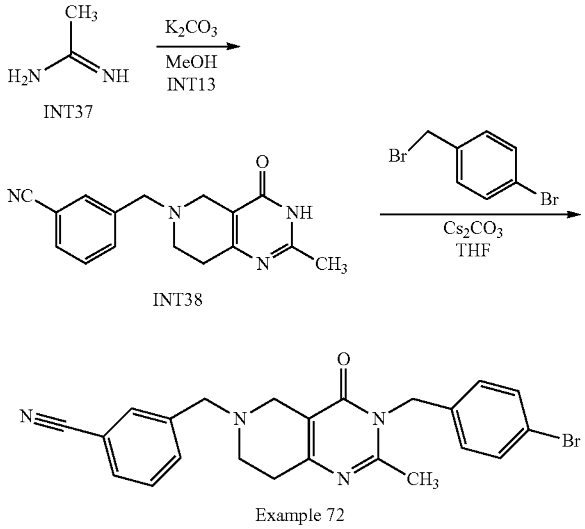

Example 71 is made by the following synthetic scheme:

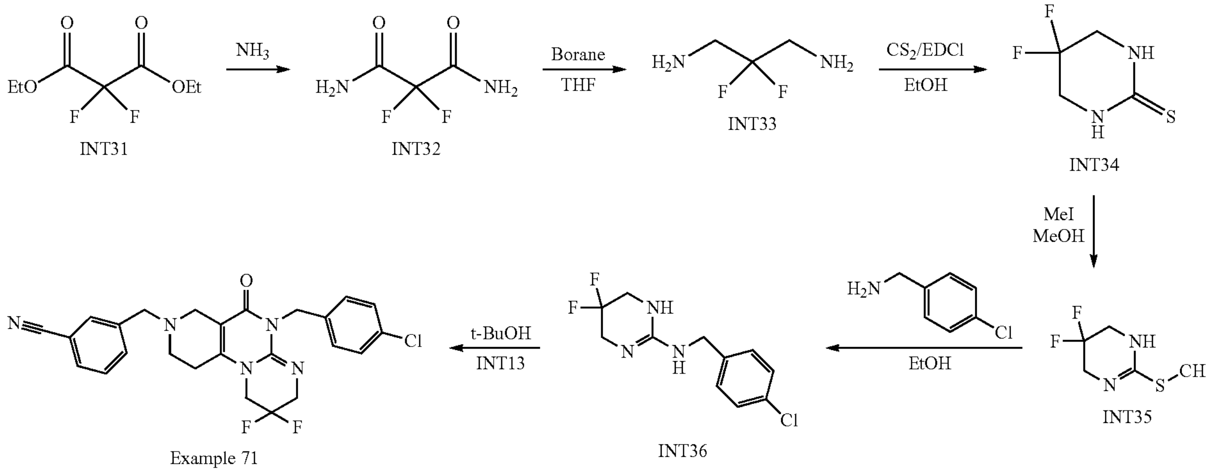

$^1$HNMR (400 MHz, $CDCl_3$) δ 2.94 (s, 2H), 3.58-3.75 (m, 8H), 4.31 (s, 2H), 5.17 (s, 2H), 7.05-7.07 (d, J=8 Hz, 1H), 7.26-7.33 (m, 3H), 7.59-7.79 (m, 4H); LC-MS: m/z=481.9 (M+1).

Example 72

3-({3-[(4-bromophenyl)methyl]-2-methyl-4-oxo-3H,4H,5H,6H,7H,8H-pyrido[4,3-d]pyrimidin-6-yl}methyl)benzonitrile Example 72

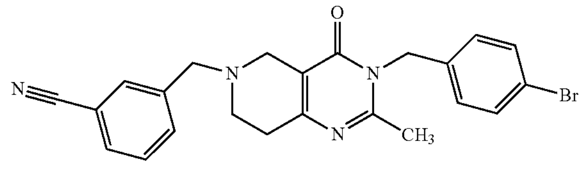

$^1$HNMR (400 MHz, $CDCl_3$) δ 2.04 (s, 3H), 2.43 (s, 4H), 3.46 (s, 2H), 3.75 (s, 2H), 5.21 (s, 2H), 7.05-7.07 (d, J=8 Hz, 2H), 7.42-7.47 (m, 3H), 7.56-7.61 (m, 2H), 7.7 (s, 1H); LC-MS: m/z=450.9 (M+1).

Example 73

3-[(2-methyl-4-oxo-3-{[4-(trifluoromethyl)phenyl]methyl}-3H,4H,5H,6H,7H,8H-pyrido[4,3-d]pyrimidin-6-yl)methyl]benzonitrile Example 73

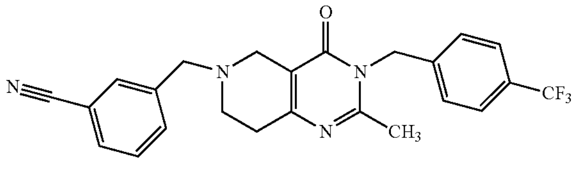

Example 73 is made by the same synthetic route as described in Example 72.

LC-MS: m/z=439.0 (M+1) and ret time 1.743 min.

Example 74

3-({3-[(4-bromophenyl)methyl]-4-oxo-3H,4H,5H,6H,7H,8H-pyrido[4,3-d]pyrimidin-6-yl}methyl)benzonitrile Example 74

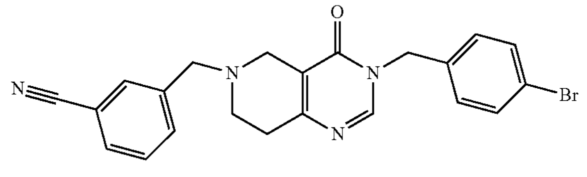

Example 74 is made by the scheme as described for Example 65.

$^1$HNMR (400 MHz, $CDCl_3$) δ 2.73-2.79 (m, 4H), 3.46 (s, 2H), 3.75 (s, 2H), 5.03 (s, 2H), 7.21-7.23 (d, 2H), 7.43-7.5 (m, 3H), 7.59 (t, J=8.8 Hz, 2H), 7.7 (s, 1H), 8.06 (s, 1H); LC-MS: m/z=434.1(M+2).

Example 75

3-[(4-oxo-3-{[4-(trifluoromethyl)phenyl]methyl}-3H,4H,5H,6H,7H,8H-pyrido[4,3-d]pyrimidin-6-yl)methyl]benzonitrile Example 75

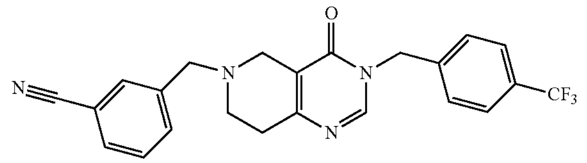

Example 75 is made by the scheme as described for Example 65.

$^1$HNMR (400 MHz, $CDCl_3$) δ 3.09 (s, 2H), 3.45 (s, 2H), 3.95 (s, 2H), 4.37 (s, 2H), 5.13 (s, 2H), 7.43-7.75 (d, 2H), 7.59-7.65 (m, 3H), 7.75-7.82 (m, 3H), 8.18 (s, 1H); LC-MS: m/z=424.2(M).

Example 76

3-({8-[(4-bromophenyl)methyl]-7-oxo-1,4,8,10-tetraazatricyclo[7.3.0.0$^{2,6}$]dodeca-2(6),9-dien-4-yl}methyl)benzonitrile Example 76

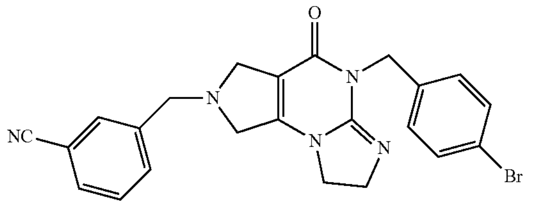

Example 76 is made by the following synthetic scheme:

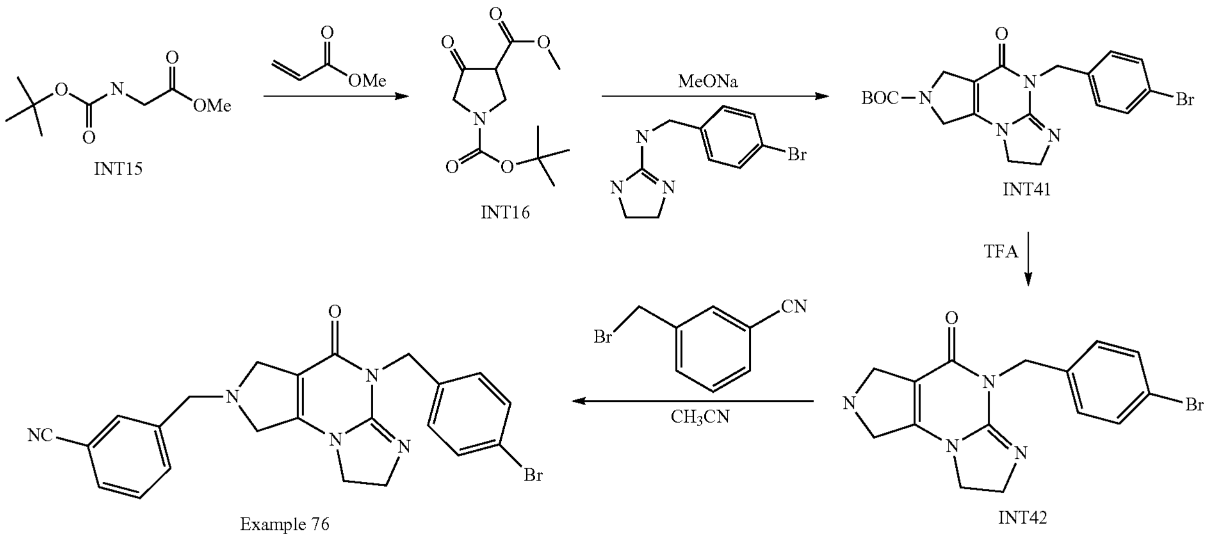

Example 76

$^1$HNMR (400 MHz, $CDCl_3$) δ 4.1-4.3 (m, 10H), 5.19 (s, 2H), 7.25 (s, 1H), 7.27 (s, 1H), 7.43-7.45 (d, 2H), 7.53 (t, J=7.6 Hz, 1H), 7.66-7.72 (m, 3H); LC-MS: m/z=463.8 (M+2).

Example 77

3-[(7-oxo-8-{[4-(trifluoromethyl)phenyl]methyl}-1,4,8,10-tetraazatricyclo[7.3.0.0$^{2,6}$]dodeca-2(6),9-dien-4-yl)methyl]benzonitrile Example 77

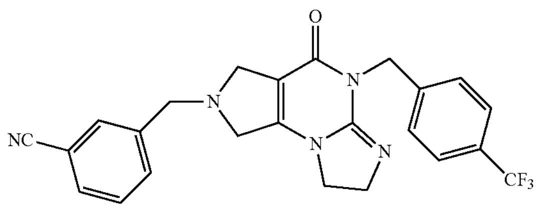

Example 77 is made by the synthetic scheme as described for Example 76.

$^1$HNMR (400 MHz, $CDCl_3$) δ 4.06-4.15 (m, 8H), 4.28 (t, J=8.4 Hz, 2H), 5.33 (s, 2H), 7.52-7.61 (m, 5H), 7.66-7.68 (d, 2H), 7.72 (s, 1H); LC-MS: m/z=451.9(M).

Example 78

2-[(4-(bromophenyl)methyl]-7-{[3-(prop-1-yn-1-yl)phenyl]methyl}-1,2,5,6,7,8-hexahydro-2,7-naphthyridin-1-one Example 78

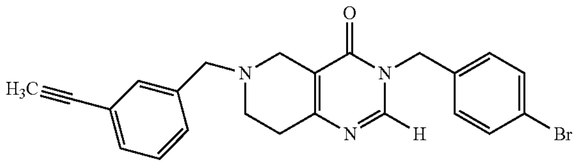

Example 78 is made by the following synthetic scheme:

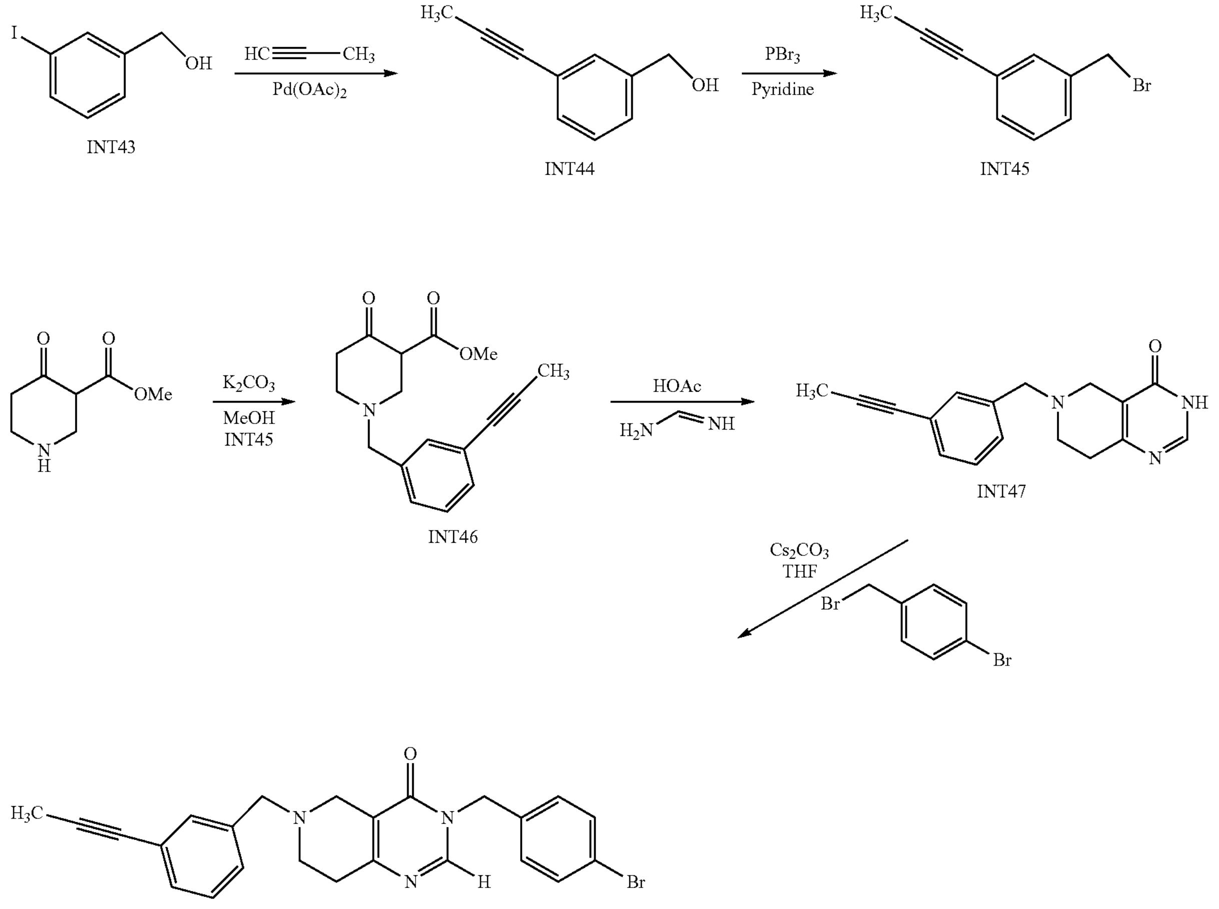

INT43 INT44 INT45 INT46 INT47

Example 78

$^1$HNMR (400 MHz, DMSO_d$_6$) δ 1.97 (s, 3H), 2.91 (s, 2H), 3.32-3.36 (m, 1H), 3.62-3.65 (m, 1H), 3.91 (s, 2H), 4.46 (s, 2H), 5.08 (s, 2H), 7.29-7.6 (m, 8H), 8.71 (s, 1H); LC-MS: m/z=449.8 (M+2).

Example 79

7-{[3-(prop-1-yn-1-yl)phenyl]methyl}-2-{[4-(trifluoromethyl)phenyl]methyl}-1,2,5,6,7,8-hexahydro-2,7-naphthyridin-1-one Example 79

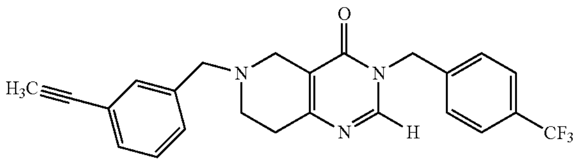

Example 79 is made by using the synthetic scheme described for Example 78.

$^1$HNMR (400 MHz, DMSO_d$_6$) 6 2.06 (s, 3H), 2.92 (s, 2H), 3.29-3.36 (m, 1H), 3.62-3.65 (m, 1H), 3.93 (s, 2H), 4.46 (s, 2H), 5.2 (s, 2H), 7.44-7.81 (m, 8H), 8.75 (s, 1H); LC-MS: m/z=437.9 (M).

Example 80

4-benzyl-8-[(4-chlorophenyl)methyl]1,4,8,10-tetraazatricyclo[7.3.0.0$^{2,6}$]dodeca-2(6),9-diene-7-one Example 80

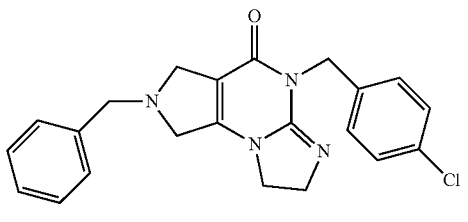

Figure 8:
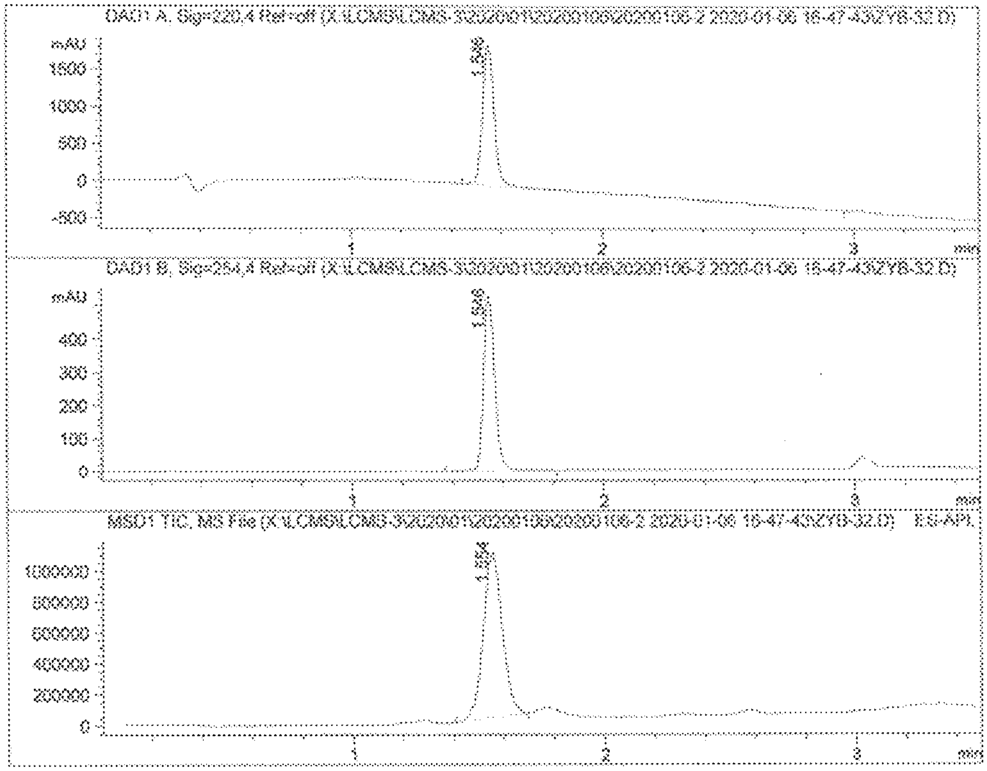
FIG. 8: LC-MS of Example 80.
Figure 9:
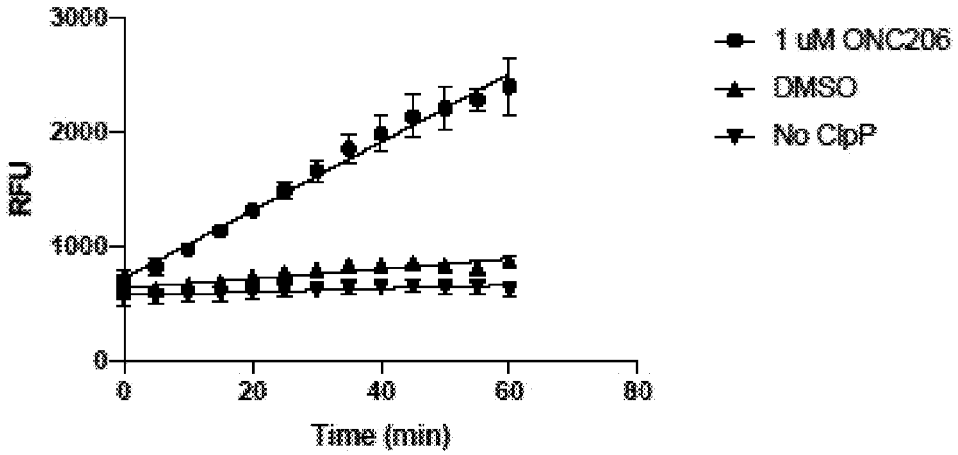
FIG. 9: Time course of ClpP activation by Ex. 60 (ONC206) at 1 uM. Purified hClpP was incubated with Ex. 60 (ONC206) using the conditions described in FIG. 2 (protocol 2). Shown are the time-dependent increase in coumarin fluorescence release from Ac-WLA-AMC by the enzymatic activity of purified hClpP.
Figure 10:
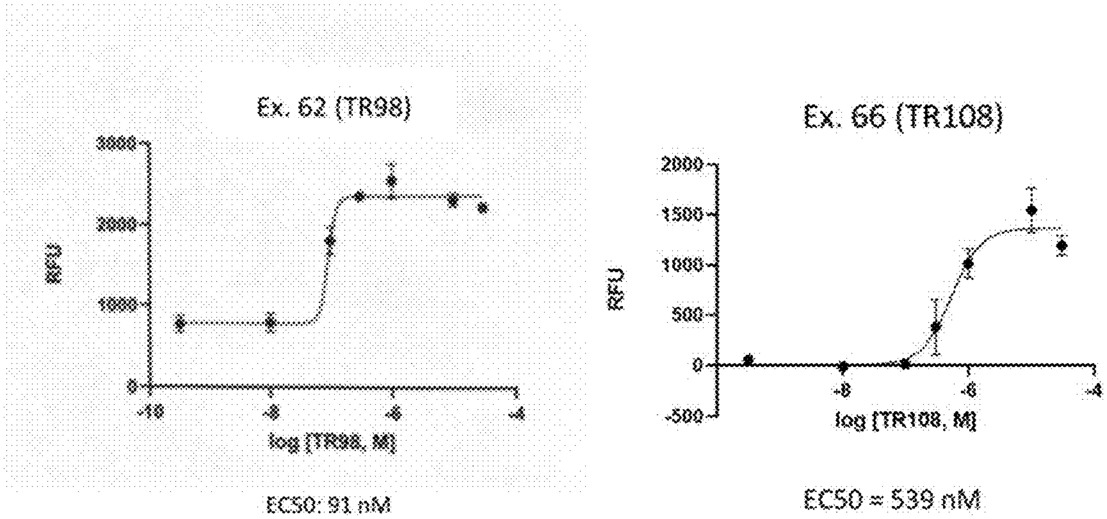
FIG. 10: Dose-dependency of ClpP activation with Ex. 62 (TR98), Ex. 66 (TR108), Ex. 67 (TR109) and Ex. 68 (TR122). Time-dependent increase of hClpP activity by TR129, TR130, TR145, TR146 and TR147. Dose-dependent increases in hClpP activity were measured in response to incubation of purified HClpP with individual compounds. HClpP activity was measured as an increase in coumarin fluorescence released from Ac-WLA-AMC by the enzymatic activity of purified hClpP as described above (protocol 2). Also shown are time-dependent increase in hClpP activity measure at 1 uM: Ex. 83 (TR129); Ex. 84 (TR130); Ex. 80 (TR145); Ex. 81 (TR146) and Ex. 82 (TR147). HClpP activity measured as increase in relative fluorescence units from hydrolysis of substrate Ac-WLA-AMC as described above (protocol 2).
Figure 11:
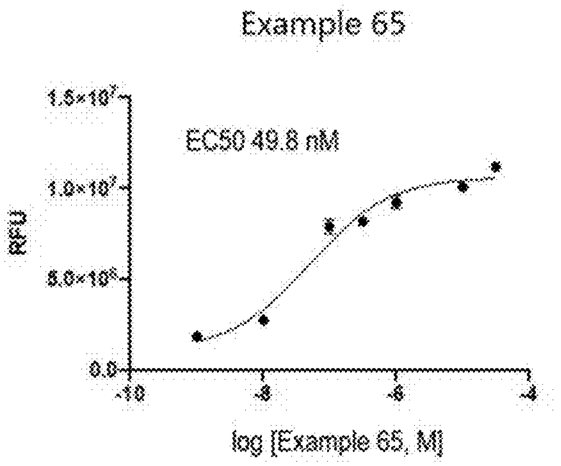
FIG. 11; Dose-dependency of ClpP activation with Example 65 (Ex. 65). Dose-dependent increases in hClpP activity were measured in response to incubation of purified hClpP with Ex. 65. HClpP activity was measured as an increase in coumarin fluorescence release from Ac-WLA-AMC by enzymatic activity of the purified hClpP as described in herein. Biology Examples and Experimental section also contains detailed information.
Figure 12:
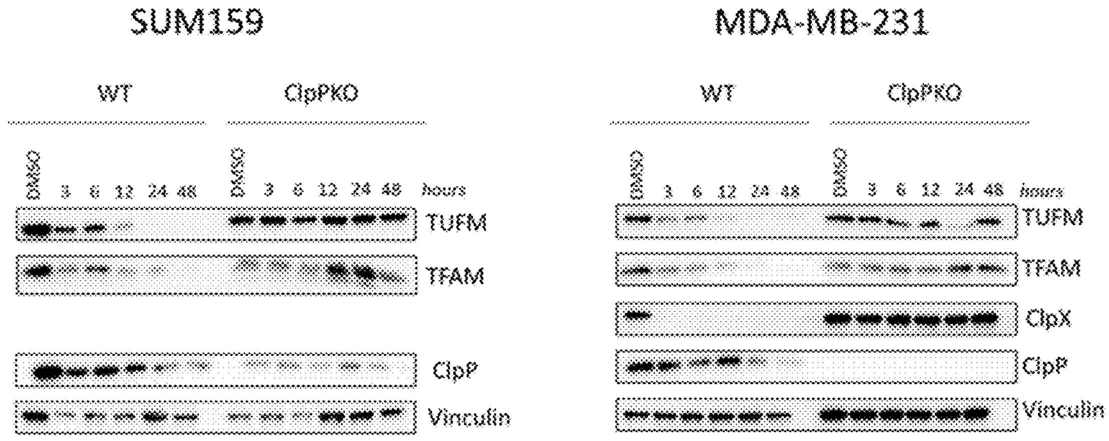
FIG. 12: Ex. 65 induces degradation of mitochondrial proteins in a time dependent manner in SUM159 and MDA-MB-231 triple negative breast cancer cells. Immunoblot of SUM159 or MDA-MB-231 cells following 0.1% DMSO (48 hrs) or 100 nM Ex. 65 for indicated timepoints (3-48 hrs) for indicated proteins. WT (wild type) with intact ClpP and ClpPKO (knockout) cells that do significantly express ClpP.

Example 80 is made by the following synthetic scheme:

LC-MS: ret time: 1.546 min, m/z=393.1(M+1). See FIG. 8 and example 62 for conditions.

Example 81

4-benzyl-8-[(4-bromophenyl)methyl]1,4,8,10-tetraazatricyclo[7.3.0.0$^{2,6}$]dodeca-2(6),9-diene-7-one Example 81

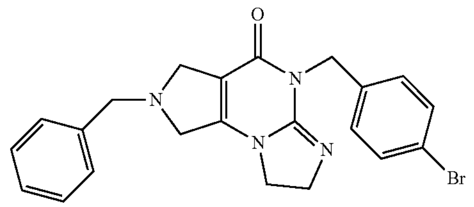

Example 81 is made by using the synthetic scheme described for Example 80.

$^1$HNMR (400 MHz, $CDCl_3$) δ 4.0 (s, 2H), 4.2-4.24 (d, 6H), 4.4 (s, 2H), 5.15 (s, 2H), 7.23-7.24 (d, 2H), 7.42 (s, 7H); LC-MS: m/z=439.1(M+2).

Example 82

4-benzyl-8-{[4-(trifluoromethyl)phenyl]methyl}1,4,8,10-tetraazatricyclo[7.3.0.0$^{2,6}$]dodeca-2(6),9-diene-7-one Example 82

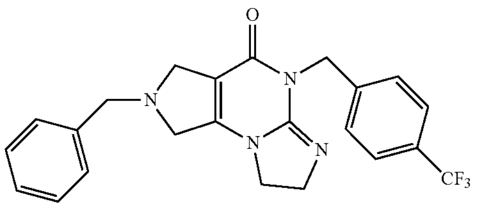

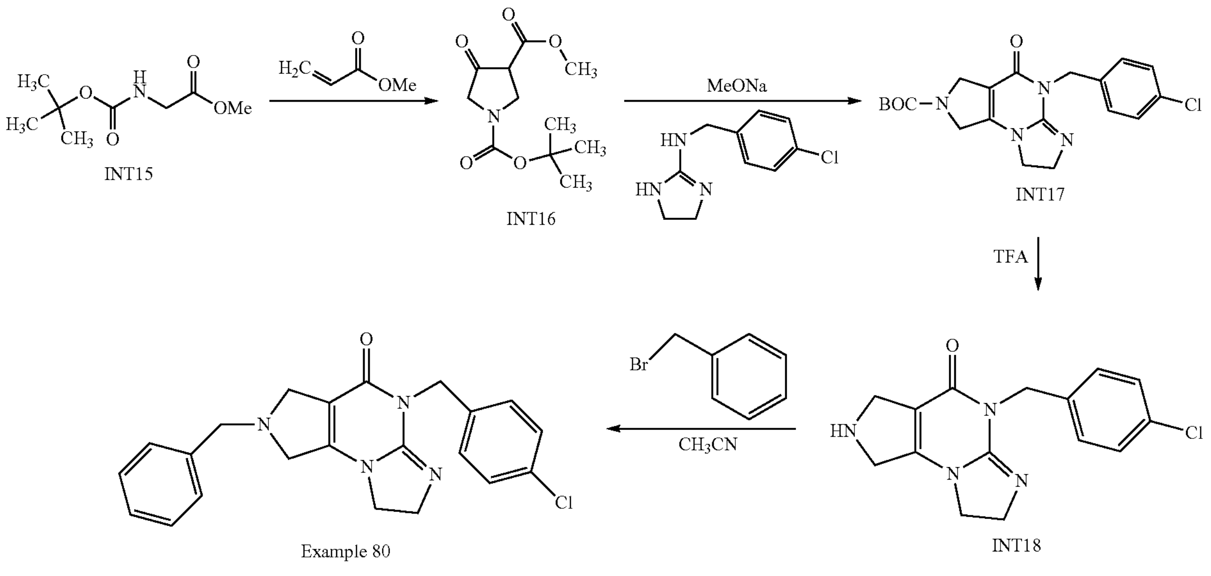

Example 82 is made by using the synthetic scheme described for Example 80.

$^1$HNMR (400 MHz, $CDCl_3$) δ 4.01 (s, 2H), 4.21-4.25 (d, 6H), 4.41 (s, 2H), 5.26 (s, 2H), 7.37-7.46 (m, 7H), 7.54-7.56 (d, 2H); LC-MS: m/z=426.9(M).

Example 83

3-({9-[(4-chlorophenyl)methyl]-8-oxo-1,5,9,11-tetraazatricyclo[8.4.0.0$^{2,7}$]tetradeca-2(7),10-dien-5yl}methyl)benzonitrile Example 83

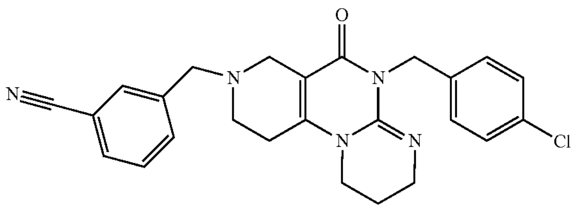

Example 83 is made by using the synthetic scheme described for Example 62.

$^1$HNMR (400 MHz, DMSO & CDCl3) 2.13 (s, 2H), 2.86 (s, 4H), 3.38 (s, 2H), 3.5 (s, 2H), 3.84 (s, 2H), 4.05 (s, 2H), 5.28 (s, 2H), 7.27-7.34 (m, 3H), 7.53 (t, J=8 Hz, 1H), 7.65-7.67 (d, 2H), 7.74 (s, 1H), 8.0 (s, 1H); LC-MS: m/z=446.1(M+1).

Example 84

3-({9-[(4-bromophenyl)methyl]-8-oxo-1,5,9,11-tetraazatricyclo[8.4.0.0$^{2,7}$]tetradeca-2(7),10-dien-5yl}methyl)benzonitrile Example 84

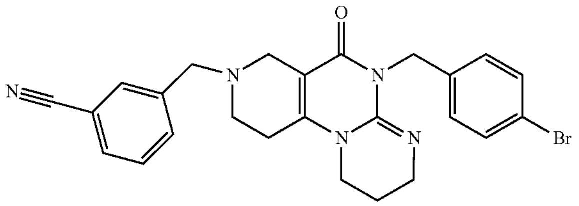

Example 84 is made by using the synthetic scheme described for Example 62.

$^1$HNMR (400 MHz, DMSO) 2.05 (s, 2H), 2.87 (s, 4H), 3.36-3.43 (m, 4H), 3.89 (s, 2H), 3.99 (t, J=5.6 Hz, 2H), 5.16 (s, 2H), 7.22-7.24 (d, 2H), 7.54-7.62 (m, 3H), 7.71-7.73 (d, 1H), 7.8-7.83 (d, 2H); LC-MS: m/z=492.1(M+2).

Biology Examples and Experimental

The following examples are put forth so as to provide those of ordinary skill in the art with a complete disclosure and description of how to make and use the present invention, and are not intended to limit the scope of this invention. Efforts have been made to ensure accuracy with respect to numbers used (e.g. amount, temperature, etc.) but some experimental errors and deviations should be accounted for.

a) Experimental Procedure/Materials and Methods

Measurement of human ClpP activity. Measurement of in vitro activity of recombinant human caseinolytic peptidase hClpP (Cat #MBS204060, MyBioSource, Boston USA) based on monitoring the release of fluorescent coumarin from fluorogenic substrate Ac-WLA-AMC (Cat #S330, Boston Biochem, Inc., Cambridge, MA) as described previously (Maurizi, M. R. et al, Methods Enzymol. 1994, 244, 314-331 and references cited therein and Woo, K. M. et al, Biol. Chem. 1989, 264, 2088-2091 and references cited therein) with minor modifications. Briefly, the activity of recombinant hClpP proteolytic subunit (1 μg/mL) was measured in the assay buffer composed of 50 mM Tris, 10 mM $MgCl_2$, 100 mM KCl, 1 mM DTT, 4 mM ATP, 0.02% Triton X-100 and 5% Glycerol, pH 8.0 (HCl) using 10 μM of fluorogenic Ac-WLA-AMC substrate as described in references above. Two different protocols were used to investigate the effects of ONC201 and the compounds of this invention on ClpP activity. Using the first protocol (Protocol 1), the reaction was initiated by immediately mixing enzyme and substrate in the presence of indicated doses of compounds. Applying a second protocol (Protocol 2), the enzyme and compounds were mixed and incubated in assay buffer for 60 min before initiating the reaction by adding Ac-WLA-ACM substrate. The kinetics of the free coumarin fluorescence was monitored using black, μ-CLEAR 96-well flat bottom plates (Cat #655090, Greiner Germany) and the fluorescence of released coumarin recorded at 350 nm excitation & 460 nm emission using BMR PHERAstar plate reader equipped with appropriate Fl module (BMG LABTECH, Durham NC). The slope of the linear portion of the fluorescence signal over the time, was a measure of the activity of hClpP. Measurements were carried out in triplicate and presented as the rate of fluorescence change at given concentrations of hClpP and substrate in the presence or absence of ONC201 or compounds of this invention. Dose-dependence of hClpP activation with different compounds was used for determination (relative $IC_{50}$) of the substance, and the activity of samples treated with DMSO (vehicle) measured as background, was subtracted from experimental data and the activity of ClpP expressed as RFU/μg of ClpP/h. See also Greer, Y. E. et al, Oncotarget, 2018, 9, 18,454-18479 and references cited therein.

Cancer cell lines. Cell data described in Tables 1 and 2 was determined as described in CN104860948 and U.S. Pat. No. 10,526,332. Additional information for cell testing is as follows: HCT116 (human colon cancer) or MDA-MB-231 (MDA 231, human breast adenocarcinoma) were dispensed in 100 ul of cell suspension in a 96-well plate. The plate was incubated for 24 hours in a humidified incubator (37° C., 5% $CO_2$). The compound from the present invention, at the appropriate test concentrations, are added to the culture media of the plate. The plate is incubated for 48 hours. CCK-8 (10 ul, see below) is added to each well. The plate is incubated from 1-4 h under conditions as described above, and the absorbance at 450 nm and 650 nm is measured with a plate reader.

Cell Counting Kit-8 (CCK-8) allows sensitive colorimetric assays for the determination of the number of viable cells in the proliferation and cytotoxicity assays. Cell Counting was by CCK-8 using WST-8 (2-(2-methoxy-4-nitrophenyl)-3-(4-nitrophenyl)-5-(2,4-disulfophenyl)-2H-tetrazolium, monosodium salt), which produces a water-soluble formazan dye upon bioreduction in the presence of an electron carrier, 1-Methoxy PMS. CCK-8 solution is added directly to the cells. WST-8 is bioreduced by cellular dehydrogenases to an orange formazan product that is soluble in tissue culture medium. The amount of formazan produced is directly proportional to the number of living cells.

For cancer cell lines, AN3CA (human uterine/endometrial cancer, Van Nyen, T. et al Int. J. Mol. Sci. 2018, 19, 2348 and referenced cited therein) cell line and Capan-2 (human pancreatic adenocarcinoma) cell line additional details for testing are as follows. Using 96 well cell culture plate (Corning Costar, Cat #3599), after addition of the test compound (Example 65, or other) the plate is incubated at 37° C., 5% $CO_2$ for 72 hours. Cell viability was determined using CCK8 assay by adding 10 uM of CCK8 into the assay well, incubate the plate for 2 hours and record luminescence using a SpectraMax i3X reader. Other 72 hour incubation studies can also using these details in addition to other experimental details described herein.

Measurement of anti-bacterial activity. Several publications describe the testing of ClpP modulators for anti-bacterial activity (Kao, Y. T. et al, PNAS 2018, 115, 8003-8008 and references contained therein and Quellette S. P. et al, J. Bacteriol 2018, 201(2) pii: e00635-18, doi:10.1128/JB.00635-18 and references cited therein. The experimental conditions described by Kao, Y. T. et al, and Quellette S. P et al, may be used to measure antibacterial effects of the compounds of this invention, include activity against *Staphylococcus aureus*.

b) Results

Figure 2:
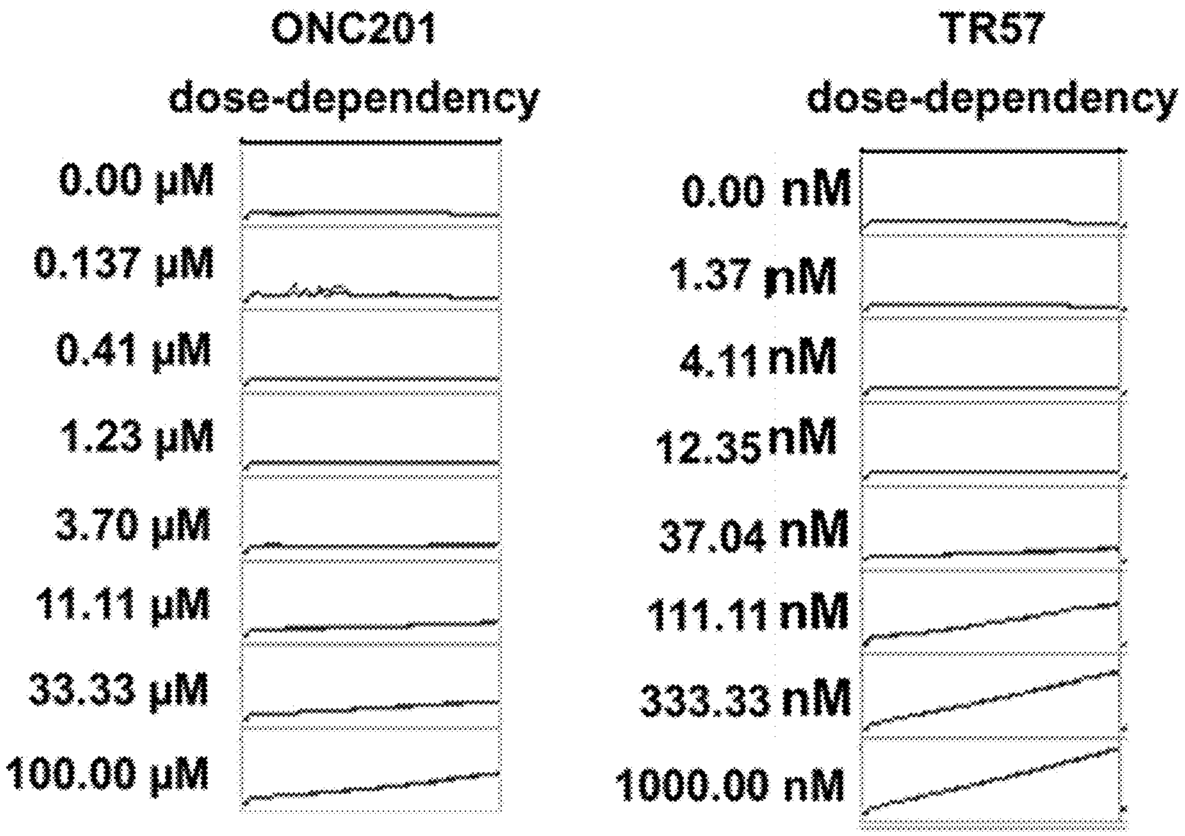
FIG. 2: Kinetics of hClpP activity after 60 min pre-incubation with ONC201 and Ex. 51 (TR57) hClpP Peptide Hydrolysis Assays in the Presence of ONC201 and TR57 after Compound Preincubation. Shown are the time-dependent increase in coumarin fluorescence release from Ac-WLA-AMC by the enzymatic activity of purified hClpP, following a 60 min pre-incubation with ONC201 or Ex. 51 (TR57). Protocol 2.
Figure 3:
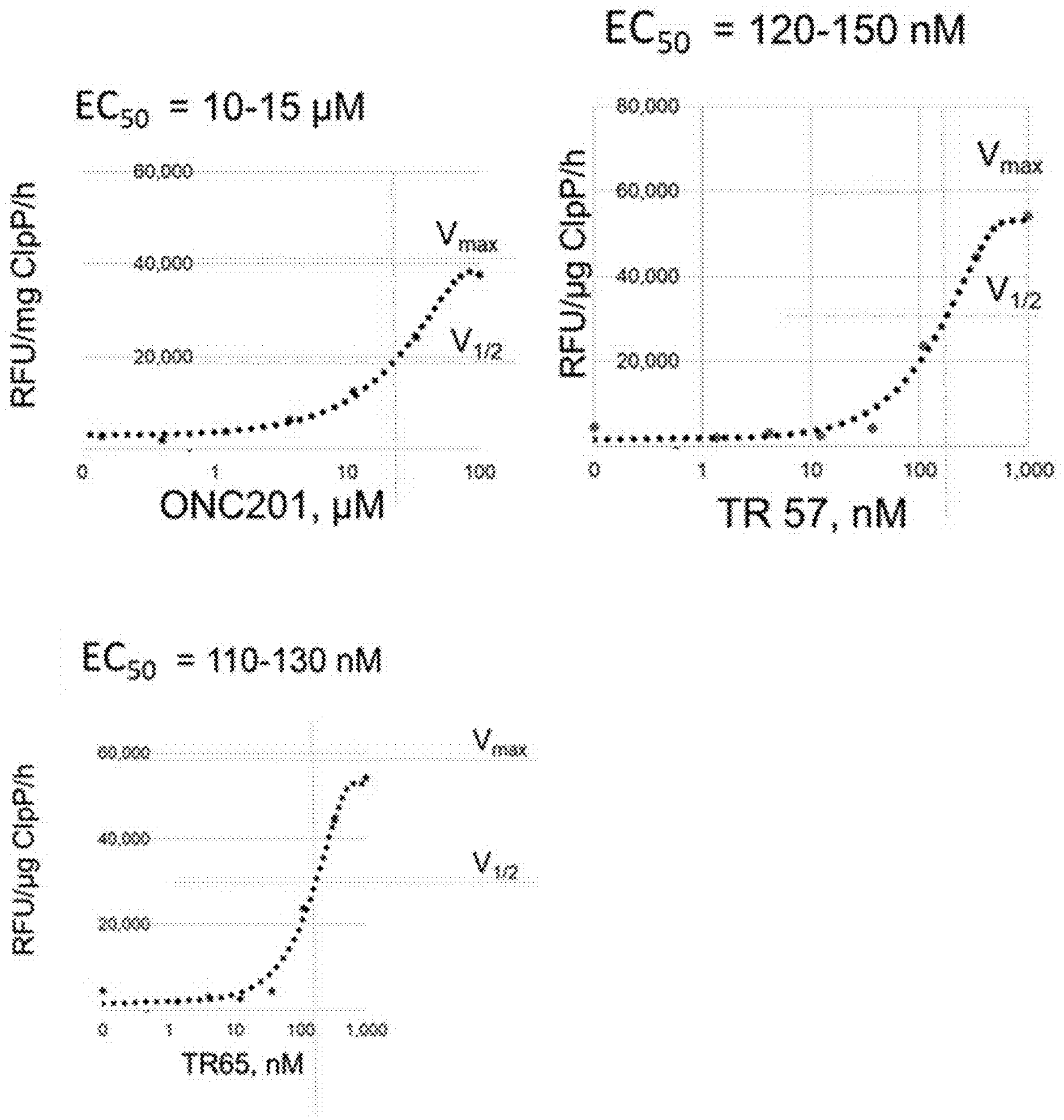
FIG. 3: Dose-dependency of hClpP activation with ONC201, Ex. 51 (TR57), Ex. 14 (TR65), Ex. 57(TR79) and Ex. 1 (D9). Shown are the dose-dependent increases in hClpP activity in response to incubation with individual compounds. HClpP activity was measured as an increase in coumarin fluorescence released from Ac-WLA-AMC by the enzymatic activity of purified hClpP as described above. For comparison, the published hClpP activator D9 is included. Activity is plotted as relative fluorescence units (RFU/ug of hClpP/hour (H)). $EC_{50}$ values represent the dose-dependent activation measured by this method.

ONC201 and TR compounds Activate CLPP Peptidase Activity. To investigate the effects of ONC201 and compounds of this invention on ClpP activity, we tested their effects on the enzymatic activity of isolated human hClpP. Using purified recombinant human mitochondrial ClpP proteolytic subunit (Cat #MBS204060, MyBioSource, Cambridge, MA) and a selective fluorogenic 7-aminomethyl coumarin-conjugated tripeptide Ac-WLA-AMC (Cat #S330, MyBioSource, Cambridge, MA) we measured the hClpP peptidase activity in the presence or absence of ONC201 and TR-compounds. Enzymatic activity of hClpP was measured in assay buffer (as described in Experimental Procedure/Materials and Methods) and the level of fluorescence of liberated coumarin monitored continuously. As shown in FIG. 1, we observed that incubation of hClpP with ONC201 or a select TR compound (TR-57) resulted in time-dependent and exponential increase in the fluorescence of coumarin AMC released due to hClpP peptidase activity. However, pre-incubation of recombinant hClpP proteolytic subunit with selected compounds for 60 min in the standard assay buffer resulted in permanent increase in the activity of enzyme and linearization of the rate of coumarin release with time and examples of the changes in kinetics and dose-dependent activity of hClpP for ONC201 and TR57 shown in FIG. 2. Plotting dose-dependences of the activity of hClpP versus the concentration of compound in semi-logarithmic scale, allows determination of $IC_{50}$, the concentration of the agent causing 50% increase in the activity of pre-incubated hClpP (FIG. 3).

Biological activity on human cancer cells for selected examples is provided in Tables 1 and 2.

TABLE 1

Biological activity data on human cancer cells for select analogs

| Compound # | $IC_{50}$ (uM, HCT116) | $IC_{50}$ (uM, MDA 231) |
|---|---|---|
| TIC10/ONC201 | 2.8 | 3.0 |
| 2 | 0.03 | 0.05 |
| 3 | 0.36 | 0.27 |

TABLE 1-continued

Biological activity data on human cancer cells for select analogs

| Compound # | $IC_{50}$ (uM, HCT116) | $IC_{50}$ (uM, MDA 231) |
|---|---|---|
| 4 | 0.082 | 0.069 |
| 5 | 1.3 | 0.069 |
| 6 | 1.4 | 1.2 |
| 7 | 0.24 | 0.40 |
| 8 | 1.8 | 0.88 |
| 9 | 0.080 | 0.120 |
| 10 | >25 | >25 |
| 11 | 0.72 | 0.74 |
| 12 | 0.22 | 0.22 |
| 13 | 0.28 | 0.28 |
| 14 | 0.011 | 0.024 |
| 15 | 0.007 | 0.024 |
| 16 | 0.028 | 0.070 |
| 17 | 0.023 | 0.064 |
| 18 | 0.022 | 0.078 |
| 19 | 0.089 | ND |
| 20 | 0.37 | 0.82 |
| 21 | 0.37 | 0.27 |
| 22 | 1.8 | 3.4 |
| 23 | 0.36 | 0.61 |
| 24 | 0.087 | 0.22 |
| 25 | 1.7 | 0.71 |
| 26 | 0.57 | 0.31 |
| 27 | 0.016 | 0.016 |

TABLE 2

Biological activity data on human cancer cells for select analogs

| Compound/Example # | $EC_{50}$ (uM, HCT116) | $EC_{50}$ (uM, MDA 231) |
|---|---|---|
| TIC10/ONC201 | 2.8 | 3.0 |
| 28 | 3.0 | 3.6 |
| 29 | 0.18 | 0.24 |
| 30 | 2.0 | 4.1 |
| 31 | 2.7 | 10 |
| 32 | 0.26 | 0.29 |
| 33 | 6.6 | 14 |
| 34 | 2.6 | 1.3 |
| 35 | 0.31 | 1.1 |
| 36 | 7.1 | 4.0 |
| 37 | 0.75 | 0.23 |
| 38 | 0.81 | 1.1 |
| 39 | 1.4 | 1.1 |
| 40 | 2.5 | 1.0 |
| 41 | 3.0 | 2.1 |
| 42 | 1.8 | 3.3 |
| 43 | 1.1 | 0.86 |
| 44 | 1.4 | 0.68 |
| 45 | 1.5 | 1.1 |
| 46 | 1.0 | 0.55 |
| 47 | 1.4 | 0.63 |
| 48 | 0.1 | 0.29 |
| 49 | 2.5 | 2.6 |
| 50 | 0.022 | 0.11 |
| 51 | 0.74 | 0.19 |
| 52 | 0.50 | 0.085 |
| 53 | 1.9 | 0.22 |
| 54 | 0.21 | 0.022 |
| 55 | ND | 1.4 |
| 56 | 0.098 | 0.29 |
| 57 | 0.057 | NT |
| 58 | 0.23 | NT |
| 59 | NT | NT |
| 60 (ONC206) | NT | NT |
| 61 | 0.097 | 0.096 |
| 62 | 0.022 | 0.021 |
| 63 | 4.0 | 5.0 |
| 64 | 10.5 | NT |
| 65 | 0.021 | NT |
| 66 | 0.0055 | NT |
| 67 | 1.2 | NT |

TABLE 2-continued

| Biological activity data on human cancer cells for select analogs | | |
|---|---|---|
| Compound/Example # | $EC_{50}$ (uM, HCT116) | $EC_{50}$ (uM, MDA 231) |
| 68 | 1.5 | NT |
| 69 | 0.097 | NT |
| 70 | 1.4 | NT |
| 71 | 0.244 | NT |
| 72 | 0.077 | NT |
| 73 | 0.069 | NT |
| 74 | 0.020 | NT |
| 75 | 0.098 | NT |
| 76 | 0.0030 | NT |
| 77 | 0.0021 | NT |
| 78 | 5.2 | NT |
| 79 | 5.7 | NT |
| 80 | 0.011 | NT |
| 81 | 0.039 | NT |
| 82 | 0.010 | NT |
| 83 | 0.280 | NT |
| 84 | 0.013 | NT |

Example 65 was examined in AN3CA (human uterine cancer) and Capan-2 (human pancreatic adenocarcinoma) cancer cell lines. After 72 hours of drug incubation, $IC_{50}$ on AN3CA is determined to be 0.001 uM and for Capan-2 the $IC_{50}$ is determined to be <0.050 uM.

List of Abbreviations

A549: human non-small cell lung cancer cell line
BSA: bovine serum albumin
ClpP: caseinolytic protease P
DMSO: dimethylsulphoxide
DNA: deoxyribonucleic acid
EDTA: ethylenediaminetetraacetic acid
ELISA: enzyme-linked immunosorbent assay
FACS: fluorescence activated cell scan/sorting
HEPES: 4-(2-Hydroxyethyl)piperazine-1-ethanesulphonic acid
HsClpP: human mitochondrial ClpP
HsClpX: AAA+ protein unfoldase
HsClpXP: an ATP-dependent protease complex found in the mitochondrial matrix
IHC: immunohistochemistry
MAB: monoclonal antibody
mRNA: messenger ribonucleic acid
PBS: phosphate buffered saline
RPMI-1640: cell culture medium used for culturing transformed and non-transformed eukaryotic cells and cell lines
siRNA: small inhibitory ribonucleic acid TR compound or TR compounds: any compound or set of compounds described herein with nomenclature beginning with TR. For example: TR57.

Amino Acid Sequence

Protein: ClpP

Organism: *Homo sapiens* (sp|Q16740|CLPP_HUMAN ATP-dependent Clp protease proteolytic subunit, mitochondrial OS=*Homo sapiens* OX=9606 GN=CLPP PE=1 SV=1) (SEQ ID NO: 1)

MWPGILVGGARVASCRYPALGPRLAAHFPA
QRPPQRTLQNGLALQRCLHATATRALPLIP
IVVEQTGRGERAYDIYSRLLRERIVCVMGP
IDDSVASLVIAQLLFLQSESNKKPIHMYIN
SPGGVVTAGLAIYDTMQYILNPICTWCVGQ
AASMGSLLLAAGTPGMRHSLPNSRIMIHQP
SGGARGQATDIAIQAEEIMKLKKQLYNIYA
KHTKQSLQVIESAMERDRYMSPMEAQEFGI
LDKVLVHPPQDGEDEPTLVQKEPVEAAPAA
EPVPAST

The invention claimed is:

1. A compound of the general Formula I:

Z1-Q Formula I or a pharmaceutically acceptable salt thereof, wherein:

Z1 is:

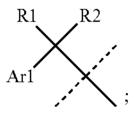

Z2 is:

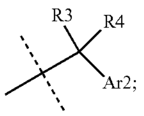

Q is

Q3

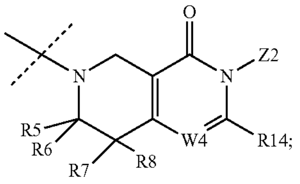

Ar1 and Ar2 are independently selected from aryl, heteroaryl, thiophenyl and phenyl;

Ar1 may be optionally substituted with from 1 to 3 J groups;

Ar2 is substituted with from 1 to 3 JJ groups;

J is independently selected from halogen, —CN, (C1-C6) optionally substituted alkyl, (C3-C9) optionally substituted cycloalkyl, (C3-C9)cycloalkyl (C1-C6)alkyl, (C1-C6)haloalkyl, —$CF_3$, —$NH_2$, —$NO_2$, —SH, —SR15, —OH, (C1-C6) optionally substituted alkoxy, —NR17R18, substituted (C3-C9)cycloalkyl (C1-C6) alkyl, (C3-C9)cycloalkyl (C2-C6)alkynyl, (C4-C8)cycloalkenyl, (C4-C8)cycloalkenyl (C1-C6)alkyl, aryl, heteroaryl, heterocyclyl, optionally substituted aryl, optionally substituted heteroaryl, optionally substituted heterocyclyl, —C(O)OH, —C(O)OR15, —OC(O)OR15, (C2-C6)alkynyl, (C2-C8)alkenyl, (C1-C6)haloalkyoxy, —$S(O)_2$OR15, —$SO_2$NR17R18, —$S(O)_2$R15, —NR15$S(O)_2$R16, —C(O)NR17R18, —C(O)R15, and —NR15C(O)R16;

JJ is independently selected from halogen, —CN, (C1-C6)haloalkyl, (C1-C6) optionally substituted alkyl, —$CF_3$, —$NH_2$, —$NO_2$, —SH, —SR15, —OH, (C1-C6) optionally substituted alkoxy, —NR17R18, heteroaryl, —C(O)OH, —C(O)OR15, —OC(O)OR15, (C2-C6)alkynyl, (C2-C8)alkenyl, (C1-C6)haloalkyoxy, —$S(O)_2$OR15, —$SO_2$NR17R18, —$S(O)_2$R15, —NR15$S(O)_2$R16, —C(O)NR17R18, —C(O)R15, and —NR15C(O)R16;

R1, R2, R3, R4, R5, R6, R7 and R8 are each independently selected from hydrogen, halogen, —OH and (C1-C3) optionally substituted alkyl;

R5 and R6 may be taken together to form ═O;

R7 and R8 may be taken together to form ═O;

R14 is independently selected from hydrogen, halogen, (C1-C6) optionally substituted alkyl, (C3-C6)cycloalkyl, (C1-C6)haloalkyl, (C2-C6) optionally substituted alkenyl, (C2-C6) optionally substituted alkynyl, —CN, —$S(O)_2$R15, —NR17R18, —$S(O)_2$R15, —C(NH)$NH_2$, —C(O)R15, and —C(O)OR15;

R15, R16, R17, and R18 are independently selected from hydrogen and (C1-C6) optionally substituted alkyl;

R17 and R18 together with nitrogen to which they are attached may form a ring of 3 to 6 atoms; and W4 is independently selected from the group consisting of =C (R14)- and nitrogen.

2. The compound of claim 1 or pharmaceutically acceptable salt thereof, wherein:

R1, R2, R3 and R4 are each hydrogen;

Ar1 is phenyl;

Ar2 is phenyl; and

R5, R6, R7 and R8 are hydrogen.

3. The compound of claim 2 or pharmaceutically acceptable salt thereof, wherein:

W4 is nitrogen;

J is independently selected from halogen, —CN, (C1-C6) optionally substituted alkyl, (C3-C9) optionally substituted cycloalkyl, (C1-C6) haloalkyl, —$CF_3$, (C1-C6) optionally substituted alkoxy, —NR17R18, optionally substituted heterocyclyl, (C2-C6)alkynyl, (C2-C8)alkenyl and (C1-C6) haloalkyoxy;

JJ is independently selected from halogen, —CN, (C1-C6) haloalkyl, (C1-C6) optionally substituted alkyl, —$CF_3$, (C1-C6) optionally substituted alkoxy, (C2-C6) alkynyl, (C2-C8)alkenyl and (C1-C6) haloalkyoxy;

R14 is independently selected from hydrogen, halogen, (C1-C6) optionally substituted alkyl and —CN.

4. The compound of claim 3 or a pharmaceutically acceptable salt thereof, wherein:

J is independently selected from hydrogen, halogen, —CN and (C2-C6) alkynyl;

JJ is independently selected from halogen, —$CF_3$, and (C1-C6) haloalkyl.

5. The compound of claim 4 or pharmaceutically acceptable salt thereof, wherein the compound is represented by formula (C10)

C10

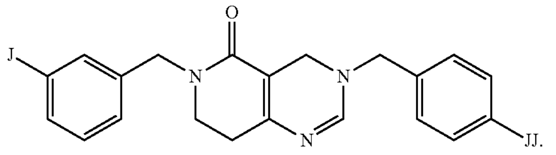

6. A compound or a pharmaceutically acceptable salt thereof, which is selected from the group consisting of:

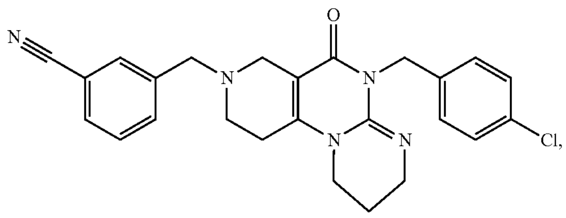

-continued

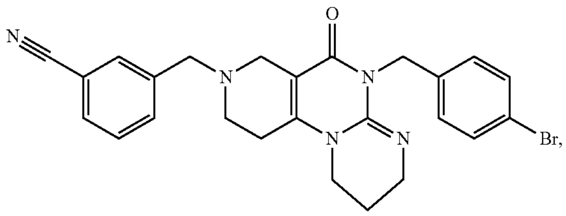

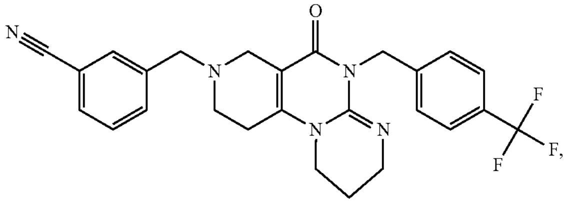

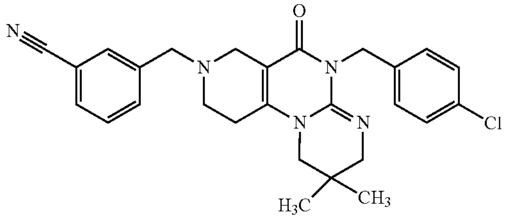

and

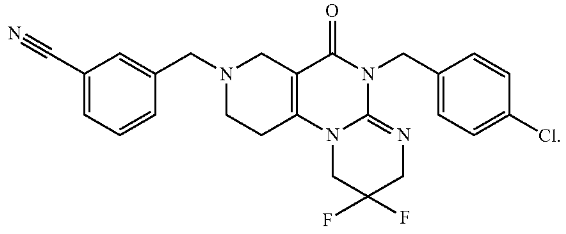

7. The compound of claim 1 or a pharmaceutically acceptable salt thereof, which is a member selected from the group consisting of:

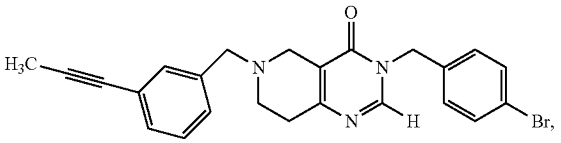

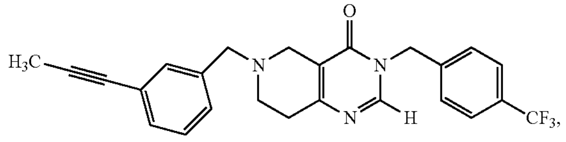

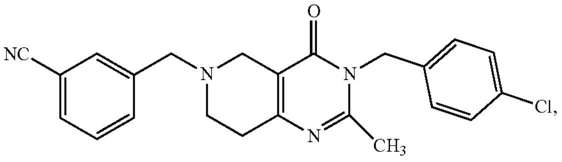

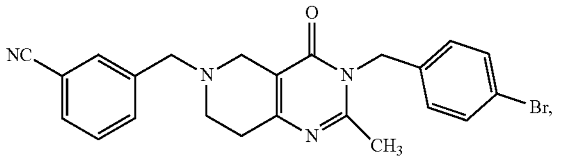

-continued

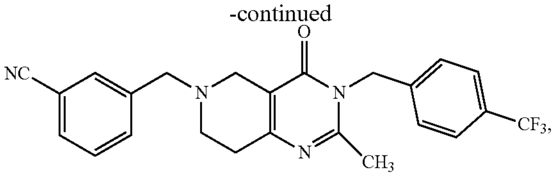

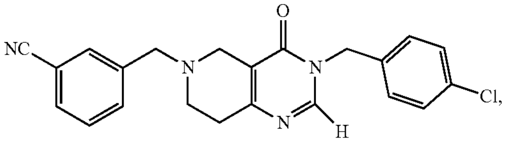

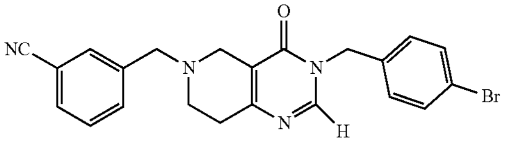

and

-continued

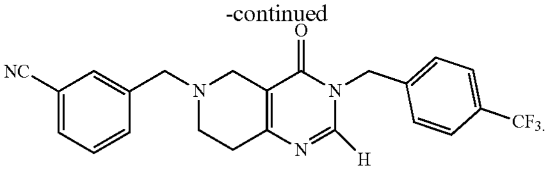

8. A method for the treatment of breast cancer or colon cancer in a subject, comprising administering an effective amount of a compound of claim 3, 6, or 7 or a pharmaceutically acceptable salt thereof.

9. A pharmaceutical composition, comprising a compound of claim 1, 3, or 7 or a pharmaceutically acceptable salt thereof, and a pharmaceutically acceptable carrier or excipient.

* * * * *